(12) United States Patent
Farzan

(10) Patent No.: US 12,082,933 B2
(45) Date of Patent: *Sep. 10, 2024

(54) METHODS OF USING BRAIN TEMPORAL DYNAMICS

(71) Applicant: Faranak Farzan, Port Moody (CA)

(72) Inventor: Faranak Farzan, Port Moody (CA)

( * ) Notice: Subject to any disclaimer, the term of this patent is extended or adjusted under 35 U.S.C. 154(b) by 551 days.

This patent is subject to a terminal disclaimer.

(21) Appl. No.: 17/039,848

(22) Filed: Sep. 30, 2020

(65) Prior Publication Data

US 2021/0177326 A1    Jun. 17, 2021

Related U.S. Application Data

(63) Continuation of application No. 15/832,105, filed on Dec. 5, 2017, now Pat. No. 10,888,264.

(30) Foreign Application Priority Data

Dec. 5, 2016   (CA) ................................ CA 2950616

(51) Int. Cl.
   *A61B 5/16*     (2006.01)
   *A61B 5/00*     (2006.01)
   *A61B 5/369*    (2021.01)
   *A61N 2/00*     (2006.01)

(52) U.S. Cl.
   CPC .............. *A61B 5/165* (2013.01); *A61B 5/16* (2013.01); *A61B 5/369* (2021.01); *A61B 5/4836* (2013.01); *A61B 5/4848* (2013.01); *A61N 2/006* (2013.01)

(58) Field of Classification Search
   CPC ......... A61B 5/16; A61B 5/165; A61B 5/0476; A61B 5/4836; A61B 5/4848; A61N 1/32; A61N 2/006
   See application file for complete search history.

(56) References Cited

U.S. PATENT DOCUMENTS 10,888,264 B2 *  1/2021  Farzan ................. A61B 5/4848

OTHER PUBLICATIONS

Andrew D. Krystal, M.D., M.S., * Mike West, Ph.D., Raquel Prado, Ph.D., Henry Greenside, Ph.D., Scott Zoldi, Ph.D., and Richard D. Weiner, M.D., Ph. D. EEG Effects of ECT: Implications for rTMS. 2000. Depression and Anxiety 12:157-165. (Year: 2000).*

* cited by examiner

*Primary Examiner* — Thaddeus B Cox
*Assistant Examiner* — Joshua Daryl D Lannu
(74) *Attorney, Agent, or Firm* — McMillan LLP

(57) ABSTRACT

A method for treating depression in a subject is provided. The method includes treating the subject by providing therapy such as administered through electroconvulsive therapy (ECT) or magnetic seizure therapy (MST). The method further includes evaluating the resulting change in the brain of the subject by measuring complexity of temporal dynamics in the brain of the subject, following treatment, to identify whether complexity of fine time scale temporal dynamics in the fronto-central and/or parieto-occipital region is reduced following treatment. The reduced complexity of fine time scale temporal dynamics in the fronto-central and/or parieto-occipital region following treatment is used to identify the subject as a responder to the therapy for treating depression. The step of evaluating further comprises identifying change in complexity of coarse scale temporal dynamics in a parieto-central region following treatment.

5 Claims, 38 Drawing Sheets

METHODS OF USING BRAIN TEMPORAL DYNAMICS

CROSS-REFERENCE TO RELATED APPLICATIONS

This application claims priority to and the benefit of Canadian patent application No. 2,950,616, filed Dec. 5, 2016.

FIELD OF INVENTION

The present invention relates generally to brain temporal dynamics. More specifically, the present invention relates to modulating the complexity of temporal dynamics in the brain for the treatment of depression.

BACKGROUND

Major depression is a leading cause of disability affecting over 350 million people globally (Murray and Lopez, 1996). Over a third of these patients fail responding to medications. Dating back to 1700s, the induction of seizures has been used to treat severe psychiatric conditions such as depression. Introduced in 1930s, seizure therapy administered through electroconvulsive therapy (ECT) still remains the most effective treatment for depression (The UK ECT Review Group, 2003) even when many other antidepressant treatments have failed. However, the cognitive side effects of ECT (Lisanhy et al., 2000, McClintock et al., 2014) limit its widespread use. Magnetic seizure therapy (MST) is an emerging antidepressant treatment that involves the induction of seizure through the administration of transcranial magnetic stimulation (TMS) (Moscrip et al., 2006; Hoy and Fitzergerald, 2010; McClintock et al., 2013). This approach to seizure induction causes less memory impairment than ECT (McClintock et al., 2013) and early treatment studies report efficacy in depression (Kayser et al., 2015). Despite decades of research, the biological targets of seizure therapy for depression remain unclear. This has hindered the progress in development of new antidepressant interventions that have comparable efficacy to ECT without the cognitive side effects. Here, we propose a novel approach in examining the biological target of seizure therapy by assessing the impact of seizure on the temporal fluctuations (i.e., dynamics) of brain signals.

Seizure is a biological phenomenon that significantly impacts brain dynamicity visualized through electroencephalography (EEG). It is increasingly evident that temporal fluctuations and variability observed in biological systems such as brain signals have a fundamental role in shaping the brain's capacity for information processing (Tononi et al., 1994; Tononi and Edelman, 1998; Spores et al., 2000; Costa et al., 2005). This temporal fluctuation, occasionally referred to as biological "noise", is distinct from random noise and structurally rich (Costa et al., 2005) exhibiting varying degree of recurring patterns (Costa et al., 2005). The less recurring temporal patterns, the more complex and unpredictable the signal is. In the brain, the complexity of signals at fine (smaller time increment) and coarse (larger time increments) time-scales is proposed to arise from transient increases and decreases in correlated activity among local and distributed brain regions, subserving, integration and segregation of information at different spatiotemporal scales (Spores et al., 2000; McIntosh et al., 2014). While majority of existing experiments have quantified the strength of functional coupling between brain regions and its disturbance in disorders of mood and consciousness (Fox et al., 2012; Kaiser et al., 2015; Sale et al.; 2015), emerging evidence points to the abnormalities in the temporal complexity of brain signals in disorders of affect and cognition (McIntosh et al., 2014).

SUMMARY OF INVENTION

In an embodiment, there is provided herein a use of a seizure or non-seizure modality for modulating the complexity of temporal dynamics in the brain for the treatment of depression as described substantially herein.

In another embodiment, there is provided herein a use of the complexity of temporal dynamics in the brain to monitor the efficacy of anti-depression treatments as described substantially herein.

In another embodiment, there is provided herein a use of the complexity of temporal dynamics in the brain to monitor the specificity of anti-depression treatments as described substantially herein.

In another embodiment, there is provided herein a use of the complexity of temporal dynamics of the brain to enhance cognition in a subject during anti-depression treatments as described substantially herein.

In another embodiment, there is provided herein a use of a seizure or non-seizure modality for modulating the complexity of temporal dynamics in the brain for the treatment of depression, wherein:
  a) a subject with symptoms of depression is treated with a seizure therapy modality, for example ECT or MST, or a non-seizure modality such as rTMS, in order to decrease the complexity of temporal dynamics of the brain as determined against the individual's baseline, for example through EEG,
  b) the modality is specifically targeted to at least one area of the brain, such as the occipital and parieto-central regions of the brain, and
  c) the complexity of the temporal dynamics of the brain s evaluated; and
  d) following the treatment the symptoms of depression are decreased while the deleterious cognitive effects of seizure therapy are limited or reduced,
  wherein, specifically, the significant reduction of the complexity of fine time scale temporal dynamics in the occipital region is indicative of a successful therapeutic outcome and the significant reduction of the complexity of coarse scale temporal dynamics in the parieto-central region is indicative of the successful limitation of the deleterious cognitive side-effects of the seizure therapy.

In another embodiment there is provided herein a use of the measurement of complexity of temporal dynamics in the brain to monitor the efficacy of anti-depression treatments, wherein
  a) a baseline EEG is made of a subject exhibiting the symptoms of depression before and following a given treatment, such as a seizure treatment like ECT or MST, or non-seizure modality such as rTMS or pharmacological means
  b) and the complexity of fine scale temporal dynamics in the occipital areas of the brain is evaluated wherein a significant reduction of the fine scale (less than 30 factors, preferably less than 20 factors) temporal dynamics in the occipital areas of the brain this is indicative of a successful depression treatment outcome, wherein the occipital regions encompass at least the right occipital pole.

In another embodiment, there is provided herein a use of the measurement of complexity of temporal dynamics in the brain to monitor the specificity of anti-depression treatments, wherein the post-treatment coarse time scale complexity is indicative of a treatment-induced cognitive decline, wherein:
 a) a baseline EEG measurement is made of a subject exhibiting the symptoms of depression before and following a given treatment, such as a seizure treatment like ECT or MST or a non-seizure treatment such as rTMS or a pharmaceutical treatment, and
 b) the complexity of coarse scale temporal dynamics of greater than 50 factors (scales determined by setting the appropriate EEG sampling rate data processing), preferably less than 70 factors, in the parieto-central areas of the brain is evaluated,
 wherein the lack of a significant change of the coarse scale temporal dynamics in the parieto-central areas of the brain post-treatment is indicative of the specificity of the intervention, in that the anti-depression treatment does not affect cognition and is indicative of a specific treatment, and conversely a significant increase in the coarse scale temporal dynamics in the parieto-central areas of the brain is indicative of a cognitive deterioration, and decreased specificity of treatment.

In another embodiment, there is provided herein a use of the measurement of complexity of temporal dynamics in the brain to enhance cognition in a subject during anti-depression treatments, wherein the coarse time scale complexity is indicative of a negative treatment induced impact on cognition, wherein:
 a) a baseline EEG measurement is made of a subject exhibiting the symptoms of depression before and following a given treatment, such as a seizure treatment like ECT or MST or a non-seizure treatment such as rTMS or a pharmaceutical treatment, and
 the complexity of coarse scale temporal dynamics of greater than 50 factors (scales are to be determined by setting the appropriate EEG sampling rate data processing), preferably less than 70 factors, in the parieto-central areas of the brain is evaluated,
 wherein a significant reduction of the coarse scale temporal dynamics in the parieto-central areas of the brain is indicative of the positive impact of the intervention on cognition and is indicative of a successful cognition-enhancing treatment.

DETAILED DESCRIPTION

Figure 1:
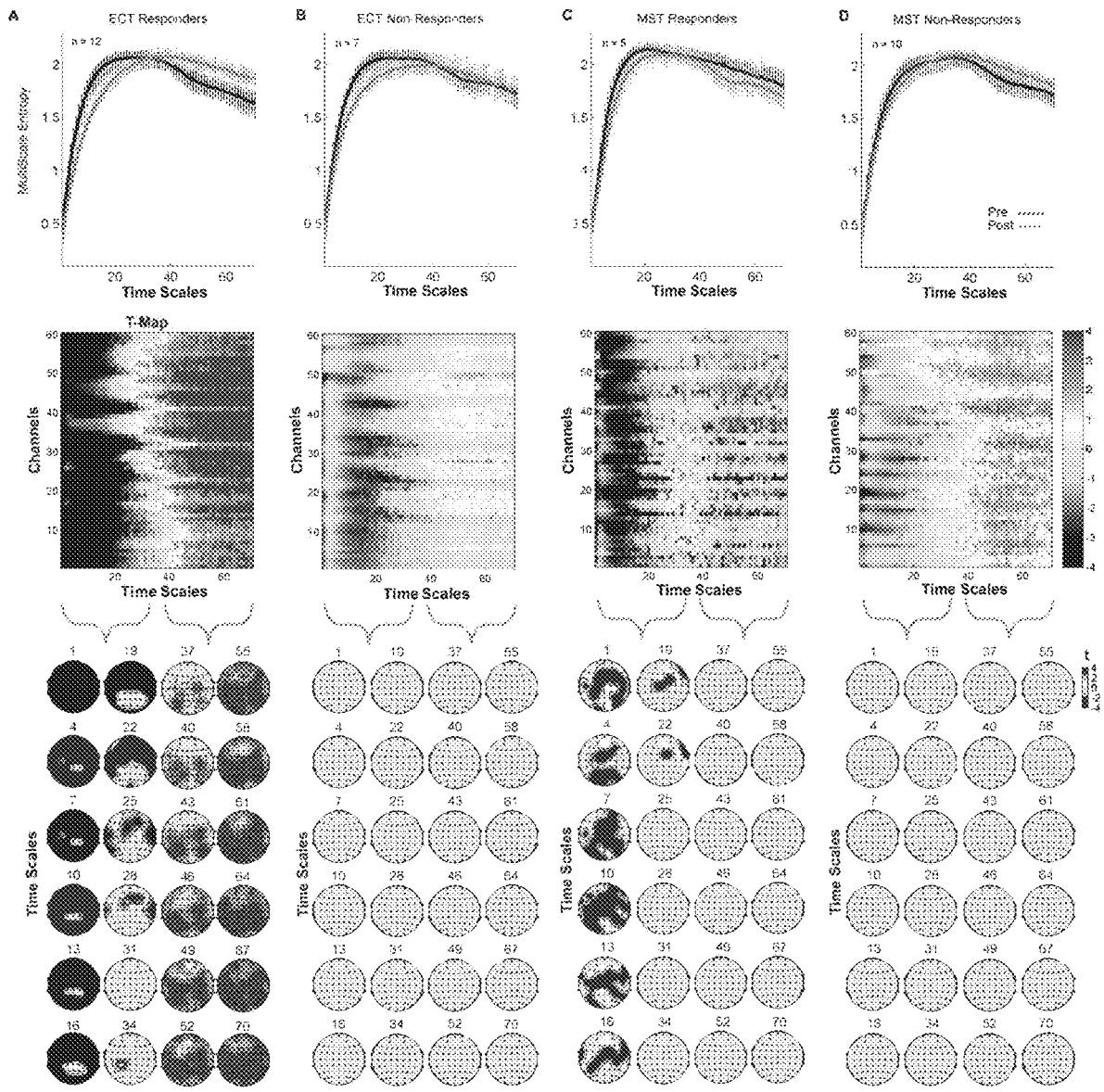
FIG. 1 shows the Effect of Seizure Therapy on Complexity of Temporal Dynamics.

We hypothesized that seizures impact both mood and cognition by modifying the temporal complexity of brain signals in a time-scale dependent manner. We obtained resting-state EEC from two independent cohorts of patients undergoing either MST (n=15) or ECT (n=19). Depressive symptoms were rated through the Hamilton Rating Scale for Depression (HAMD). General cognition and autobiographical memory were obtained through the Montreal cognitive assessment scale (MoCA) and autobiographical memory interview (AMI) (Table 1).

MATERIAL AND METHODS

Patients. A total of 34 subjects (age=46.0±14.0, 21 females) diagnosed with treatment-resistant MDD participated in either of two parallel open-label seizure therapy research protocols at Centre for Addition and Mental Health (19 ECT and 15 MST). The demographic and clinical characteristics are in Table 1.

TABLE 1

Demographics and Clinical Characteristics

|  | ECT Responders [n = 12] | ECT Non-responders [n = 7] | MST Responders [n = 5] | MST Non-responders [n = 10] |
|---|---|---|---|---|
| Age (years) | 43.3 ± 16.3 | 57.7 ± 9.2 | 45.8 ± 8.01 | 40.1 ± 15.5 |
| Sex, M/F | 4/8 | 2/5 | 2/3 | 5/5 |
| Illness Duration, Years [n] | 19.9 ± 11.5 [11] | 19.3 ± 13.6 | 25.4 ± 14.6 | 18.3 ± 14.2 |
| Number of Treatments | 12.5 ± 4.0 | 14.4 ± 3.2 | 18.6 ± 7.5 | 21.5 ± 5.8 |
| Site of Treatment, [n] | right unilateral ultra brief pulse [12] | Right unilateral ultra brief pulse [4] bitemporal standard pulse (2) unilateral followed by bitemporal (1) | Midline Frontal [5] | Midline Frontal [10] |
| Stimulation Frequency, [n] | NA | NA | 100 Hz [4] 50 Hz [0] 25 Hz [1] | 100 Hz [8] 50 Hz [2] 25 Hz [0] |
| % Change in HAMD | 65.20 ± 7.8 | 13.5 ± 23.4 | 70.5 ± 16.0 | 13.6 ± 21.4 |
| % Change in MoCA, [n] | −13.0 ± 11.9 [4] | −7.69 ± 10.9 [2] | 12.3 ± 24.2 [5] | 0.9 ± 11.8 [8] | plateaued (refer to Table 1 for number of treatments). Finally methohexital was administered for sedation and succinylcholine as neuromuscular blocker. In general, the target dosage was 0.75 mg/kg of methohexital and 0.5 mg/kg of succinylcholine. MST was administered with Magpro MST using a Twin Coil (Magventure, Denmark). The centre of each circular coil was placed over F3 and F4 respectively, using the EEG international 10-20 system. This induces the Seizure Therapy. ECT was administered with MECTA spECTrum 5000Q (Corporation, Lake Oswego, OR) according to standards of practice (Sackeim et al., 2008). Sixteen patients received right unilateral ultra brief (RUL-UB) pulse width ECT, one received bitemporal (BT) brief pulse width ECT, and two started on RUL-UB and were switched to BT due to lack of efficacy (Table 1). Treatment sessions occurred twice or three times per week. Seizure threshold titration was used to determine stimulus intensity: RUL-UB was delivered at 6×threshold with a pulse width of 0.3 to 0.37 msec and BT was delivered at 1.5× threshold with a pulse width of 1.0 msec. ECT treatments were continued until depressive symptoms was in remission or improvement had highest electric field strength between the two coils corresponding to Fz (Deng et al., 2013) The orientation of the magnetic fields was posterior-anterior. Subjects underwent a dose titration procedure to establish convulsive stimulation threshold. At 100 Hz and 50 Hz an initial train of 200 pulses was used followed by increments of 200 pulses with a maximum train of 1000 pulses. At 25 Hz an initial train of 100 pulses was used with increments of 100 pulses up to a maximum of 500 pulses. Twelve subjects received 100 Hz, two subjects received 50 Hz and one subject received 25 Hz (Table 1). All stimulations occurred at the maximum stimulator output of 100%. Threshold seizure was defined as a generalized tonic-clonic activity≥20s of visual motor activity or ≥25s of EEG seizure activity. Subsequent treatments occurred three times per week, and were initially delivered with a train 400 pulses longer in the 100 Hz and 50 Hz group and 200 pulses longer in the 25 Hz group. In subjects that had not achieved a 50% reduction in HAMD after three treatments, the dose was increased by 100 pulses (25 Hz), or 200 pulses (50 Hz, 100 Hz) up to a maximum of 500 or 1000 pulses, respectively. A maximum of 24 sessions were allowed in the acute course. Methohexital (n=9), methohexital with remifentanil (n=5), and ketamine (n=1) were administered for sedation and succinylcholine was used as the neuromuscular blocker.

EEG. Ten minutes of resting-state eyes closed EEG data were recorded within one week prior to the start and within 48 hours after the completion of a course of seizure therapy in both ECT and MST protocols. Subjects were instructed to sit in an armchair with eyes closed. EEG recording was through a 64-channel NeuroScan EEG system. The reference electrode was behind CZ electrode, and ground was behind FZ. The sampling rate was 10 kHz. The online filer setting was 0.05 to 1 kHz. The skin/electrode impedance was kept below 5 kOhm.

Mood. Changes in depressive symptoms were assessed by HAMD within one week prior to the start and within 48 hours after the completion of a course of seizure therapy in both ECT and MST protocols. Response to treatment was defined as 50% change in HAMD from baseline.

Cognition. 19 patients (6 ECT and 13 MST) completed the MoCA within 48 hours prior to and within a week after a course of seizure therapy in both protocols. In addition, the autobiographical memory interview short form (AMI-SF) was completed in 12 MST patients before and after a course of seizure therapy.

EEG Preprocessing. Data were imported into MATLAB (The MathWorks, Inc. Natick, MA, USA) for preprocessing. The open source signal processing functions in EEGLAB toolbox version 12.0 (Delorme and Makeig, 2004) were used for data import and preprocessing. The EEG signals were epoched into segments of two seconds duration and down sampled to 1 kHz. A notch filter (band-stop: 55-65 Hz) was used to remove the 60 Hz noise. EEG signals were band passed filtered 1-50 Hz to further minimize contamination by high frequency artifact. The infinite impulse response (IIR) Butterworth filter of second order and forward and backward filtering were applied to maintain a zero phase shift. All epochs were manually reviewed and trials and channels containing eye movements, muscle or any other non-physiological artifact were discarded. The data was average re-referenced.

Power. The EEGLAB function spectopo was used to obtain the power spectrum for each electrode. The relative power was obtained for 1 to 50 Hz frequencies. Relative power was calculated as the ratio in the power of each frequency relative to the sum of power across all frequencies.

Multi-Scale Entropy. MSE was examined across all electrodes using two steps (Costa et al., 2005): The coarse-graining process and the calculation of the sample entropy (SampEn) for each coarse-grained time series. First, for a given time series $\{x_1, x_2, \ldots x_8\}$, the multiple coarse-grained time series $\{y_1^{(r)}, y_2^{(r)}, \ldots, y_N^{(r)}\}$ at scale factor $\tau$ (in this paper referred to as time scale) were calculated by averaging the data points within non-overlapping windows of increasing length $\tau$. Each element of the coarse-grained time series $y_1^{(r)}$ was calculated according to the equation:

$$y_1^{(\tau)} = \frac{1}{r} \sum_{1=(j-1)x-1}^{jx} x_1 \quad (1)$$

where $\tau$ represents the scale factor (i.e., time scale) and ?

$$\left(1 \le j \le \frac{N}{x}\right)$$

represents the time index of the element. The length of each coarse-grained time series was M, where $$M = \text{floor}\left(\frac{N}{x}\right).$$

At scale factor (or time scale) $r=1$, the coarse-grained time series was the original time series. Second, the degree of predictability was measured for each of the multiple coarse-grained time series $\{y_1^{(r)}, y_2^{(r)}, \ldots, y_N^{(r)}\}$ using SampleEn. SampleEn was calculated according to the equation:

SampleEn$(r,m,M)=-ln(C(m+1)/C(m))$ (2)

where C(m) is the total number of pairs of m consecutive similar data points, C(m+1) is the total number of pairs of m+1 consecutive similar data points in the multiple coarse-grained time series. SampleEn quantifies the variability of time series by estimating the predictability of amplitude patterns across a time series. In our experiments, two consecutive data points were used for data matching (i.e., m=2) and data points were considered to match if their absolute amplitude difference was less than 15% (i.e., r=0.15) of standard deviation of time series. MSE was calculated for a 30 second continuous epoch.

EEG Source Localization. EEG source localization was performed using an open-source application, Brainstorm (Tadel et al., 2011). First, the electrode locations of our 68-channel Neuroscan Quik Cap EEG electrode sites were co-registered to the ICBM152 MRI template in Brainstorm. The forward solution was then calculated using the Open-MEEG BEM head model (Gramfort et al., 2010) and the inverse solution was derived using sLORETA (Pascual-Marqui, 2002), with the solution space constrained to the cortex surface. To localize the dynamics of neural activity, we used the Destrieux Atlas, which provides 148 regions of interest (ROIs) in the MNI co-ordinate space (Destrieux et al., 2010). After the EEG data was mapped to the 148 ROIs, MSE and power spectrum measures were calculated for all subjects at these sources.

Statistics

In addition to two intervention groups of ECT and MST, subjects were grouped into two groups of antidepressant responders and non-responders: subjects were grouped as responders if there was a 50% or higher change in HAMD relative to baseline, and non-responders otherwise. Analysis of variance was used to 1) examine the effect of seizure therapy on MSE (1-70 time-scales) and relative power (1-50 Hz frequencies) for the main effect of Seizure Therapy Intervention (ECT, MST) and Time (Pre, Post), as well as 2) Antidepressant Response (Responder, Non-Responder) and Time (Pre, Post) across 60 electrodes in sensor space and 148 ROIs in source space. Bootstrapping was used to correct for multiple comparisons in the analysis of variance. For the post-hoc t-test comparisons, cluster-based non-parametric permutation test (Maris and Oostenveld, 2007) was used to correct for the multiple comparisons in the multi-dimensional dataset (60 channels (or 148 ROIs)×50 Frequencies, 60 channels (or 148 ROIs)×70 scales) by assigning significance statistics to the probability of size clusters formed by pooling adjacent pixels with original test statistics $p<0.05$. The significance of original clusters was defined against probably distribution of clusters obtained through 1000 permutations of the shuffled data labels. Identical parameters were used across the cluster-based permutations: threshold statistics of $p<0.05$, identical neighborhood, 1000 permutation using Monte Carlo approach with cluster test statistics computed as the maximum of the cluster-level summed values. Analysis of variance, and post-hoc paired t-test and independent sample t-test analyses were used to calculate the original test statistics. Spearman correlation coefficient was used to examine the association between change in complexity and symptom severity or cognitive score. Similarly, cluster-based non-parametric permutation test was applied to the behavioral scores to correct for the multiple comparisons in the correlation analyses.

In addition to correlation analysis, it was examines if change in complexity classified patients based on antidepressant and cognitive response. Subjects were grouped to have had cognitive decline if the percent change in MoCA was negative. For AMI-SF, median performance was used to divide the patients into two groups. The level of prediction was quantified by the receiver operating characteristics (ROC) curve, plotting the sensitivity and specificity of the predictor (change in complexity) across all possible threshold values. To determine the significance of the prediction, the area under the curve (AUC), standard error of the AUC and confidence intervals were quantified for each electrode and source.

Throughout the paper, except otherwise noted, reported statistics are corrected p values, and descriptive values indicate mean and standard deviation unless otherwise stated. Percent change (i.e., %Δ) in outcome variables is calculated as: (post treatment score−baseline score/baseline score)×100, except for HAMD which is calculated as (baseline score−post treatment/baseline score)×100.

RESULTS

The Impact of Seizure on Neural Oscillations

There was a significant (p<0.05) main effect of Intervention (df=72, mean F=14.7 (4.8 to 53.2)), Time (df=72, mean F=7.3 (4.8 to 19.9)) and Intervention×Time interaction effect (df=72, mean F=7.1 (4.3 to 18.4)) across several frequencies and electrodes. There was also a significant main effect of Antidepressant Response (mean F=5.10 (3.98 to 6.83)), Time (mean F=24.63 (4.07 to 80.16)), and Antidepressant Response×Time interaction effect (mean F=5.98 (4.01 to 61.86)) across multiple scales and ROIs, however the main effect of Intervention or Intervention×Time interaction effect were not significant. Finally, there was a main effect of Antidepressant Response (mean F=5.14 (3.61 to 9.58)), Time (mean F=27.42 (4.00 to 111.14)) and an interaction effect of Antidepressant Response×Time (mean F=6.00 (3.96 to 14.53)) across multiple scales and ROIs.

Post-hoc analyses replicated the findings of prior studies that ECT induces an increase in relative power of slow cortical oscillations (Nobler and Sackeim, 2008). This effect was spatially global and present regardless of the ECT therapeutic outcome. It was significant for frequencies less than 8 Hz in responders (FIG. S1 A) and was between 2 to 7 Hz in non-responders (FIG. S1 B). However, the slowing of oscillations was not significant in MST (FIG. S1 C-D). Consistently, we replicated the previous finding (Nobler and Sackeim, 2008) that the spatially global increase of slow oscillations (e.g., 1 Hz) is associated with decline in general cognition (FIG. S3 A). We found no association between change in slow oscillations and change in depressive symptoms (FIG. S2 A).

We discovered that common to ECT and MST responders there was a global reduction in relative power of oscillations above 18 Hz (FIG. 51 A, C). ECT non-responders also had a global decrease in oscillations between 10 to 35 Hz (FIG. S1 B). No changes were observed in MST non-responders (Figure St D). Comparing ECT with MST intervention group, we identified that ECT treatment led to higher increases in slow oscillations and higher decreases in high frequency oscillations (FIG. S4 A). This finding was also spatially global. Furthermore, comparing antidepressant responders with non-responders revealed that responders exhibited higher reduction in the power of 22 Hz oscillations and also higher frequency oscillations (FIG. S4 B). This finding was spatially global at ~22 Hz, but more local in higher frequencies (30-50 Hz). Specifically in 30-50 Hz, the reduction in power is observed in regions such as the inferior frontal sulcus, left orbital part of the frontal inferior gyrus, bilateral preoccipital notch, orbital gyri, lateral orbital sulcus, lateral occi-temporal sulcus, medial orbital sulcus, bilateral parieto-occipital sulcus, or bilateral superior parietal lobule.

The results of correlation analysis revealed that the reduction in high frequency oscillations (gamma, e.g., 45 Hz) was correlated with improvement in depressive symptoms (FIG. S2 A). This effect was localized to fronto-central (e.g., AF4, F1, FZ, F2, F4, FC2) and parieto-occipital (e.g., P7, P5, PO7, PO5, PO4, PO6, PO8, O1, OZ) brain regions in sensor space. In source space, there were significant negative clusters in brain areas including the orbital sulci and gyri, bilateral posterior-dorsal part of the cingulate gyrus (dPCC), ventral PCC (vPCC), precuneus, parieto-occipital sulcus, occipital pole, inferior temporal gyrus, and lateral occi-temporal sulcus in frequencies higher than 30 Hz (FIG. S5 A).

Finally, a spatially widespread decrease in low frequency oscillations (<9 Hz) was correlated with a change in cognition (FIG. S3 A). Source analysis also revealed that this effect was spatially global. Finally, reduction in high frequency oscillations (e.g., >40 Hz) in parieto-central regions (e.g., C1, C3, CZ, CP3, P1, PZ, P2, P4, POZ) was correlated to change in cognition. In source space, this effect was identified primarily I brain regions including the central sulcus, angular gyrus, and subparietal sulcus (FIG. S5 B).

The Impact of Seizure on Temporal Complexity

We then employed multi-scale entropy (MSE) (Costa et al., 2005) to quantify the change in complexity of dynamics across multiple time-scales. In sensor space, there was a significant (p<0.05) main effect of Intervention (df=72, mean F=10.5 (4.7 to 27.2)), Time (df=72, mean F=6.7 (4.6 to 14.4)) and Intervention×Time interaction effect (df=72, mean F=7.2 (4.5 to 18.6)) across multiple time-scales and electrodes. There was also significant main effect of Antidepressant Response (mean F=5.1 (4.5 to 6.8)), Time (mean F=13.7 (4.1 to 46.5)), and Antidepressant Response×Time interaction effect (mean F=6.3 (4.3 to 11.2)). Similarly, in source space, we found a significant main effect of Intervention (mean F=14.84 (4.33 to 46.52)), Time (mean F=6.74 (4.20 to 17.4)) and Intervention×Time interaction effect (mean F=5.76 (4.16 to 11.20)) across multiple scales and ROIs. Finally, there was a main effect of Antidepressant Response (mean F=5.59 (3.87 to 10.43)), Time (mean F=16.07 (4.02 to 61.19)), and interaction effect of Antidepressant Response×Time (mean F=5.92 (4.04 to 17.09)) across multiple scales and ROIs.

Figure 5A:
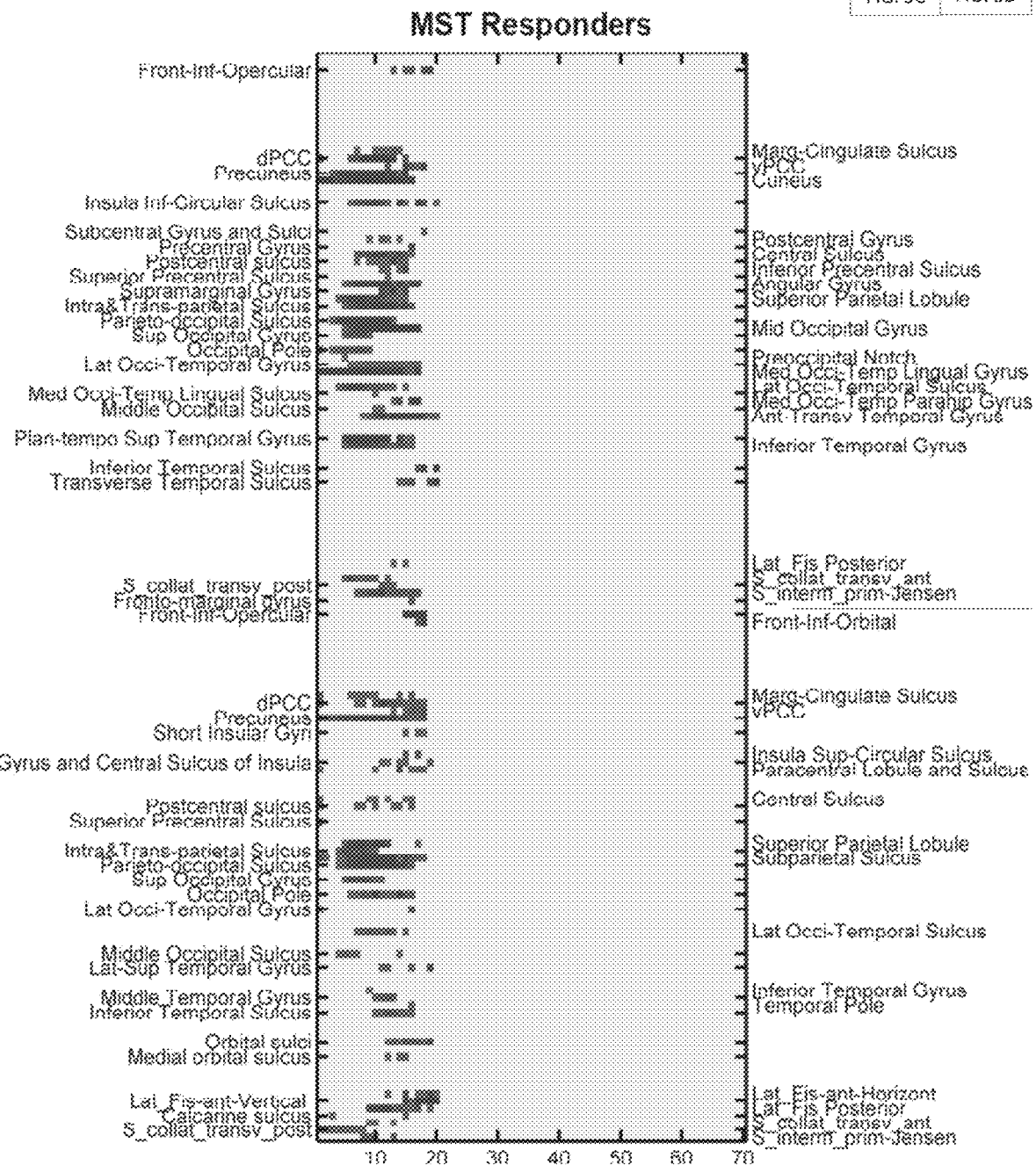
FIG. 5 shows a Seizure induced Modulation of Complexity and Its Association with Mood and Cognition in the Source Space.
Figure 5B:
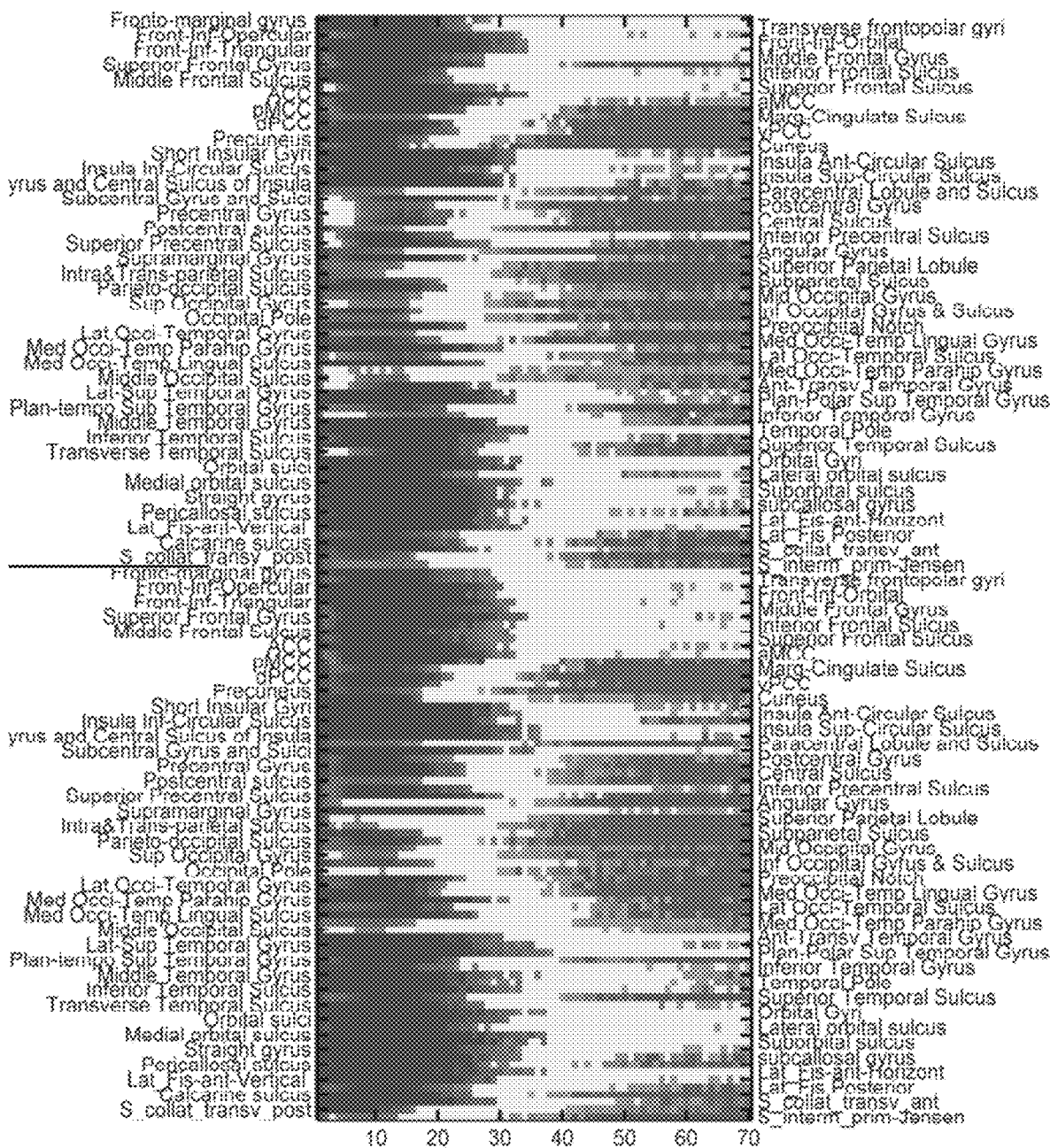

Post-hoc analysis revealed that, change in temporal complexity was only significantly modified in responders of both seizure therapies. Common to ECT and MST responders, there was a decrease in time-scales finer than 20 factors (FIG. 1A, C). ECT responders showed a significant (cluster p=0.003) global decrease in time-scales less than 30 and a significant (cluster p=0.002) global increase in coarser time-scales (spatially global changes are seen in time scales>50). Source-space analysis (FIG. 5B) confirmed the spatially global extent of this finding. By contrast, in MST responders, a wide spread reduction in time-scales less than 20 was observed (cluster p=0.033). In MST responders, the reduction of MSE in fine time-scales (e.g., scale factor 4) was found in the parieto-occipital (P1, P3, P2, P4, POZ, PO3, PO5, PO7, PO4, PO6, PO8, O1, OZ) and fronto-central regions (F4, FC1, FC2, FCZ, CZ, C1, CZ) in sensor space. Similarly, in source space, this change was observed across several tempro-parieto-occipital regions (e.g., cuneus, precuneus, posterior-dorsal part of the cingulate gyrus (dPCC), parieto-occipital sulcus, occipital pole, etc.) (FIG. 5A). No significant changes were observed in either ECT or MST non-responders (FIG. 1B, D).

Figure 2A:
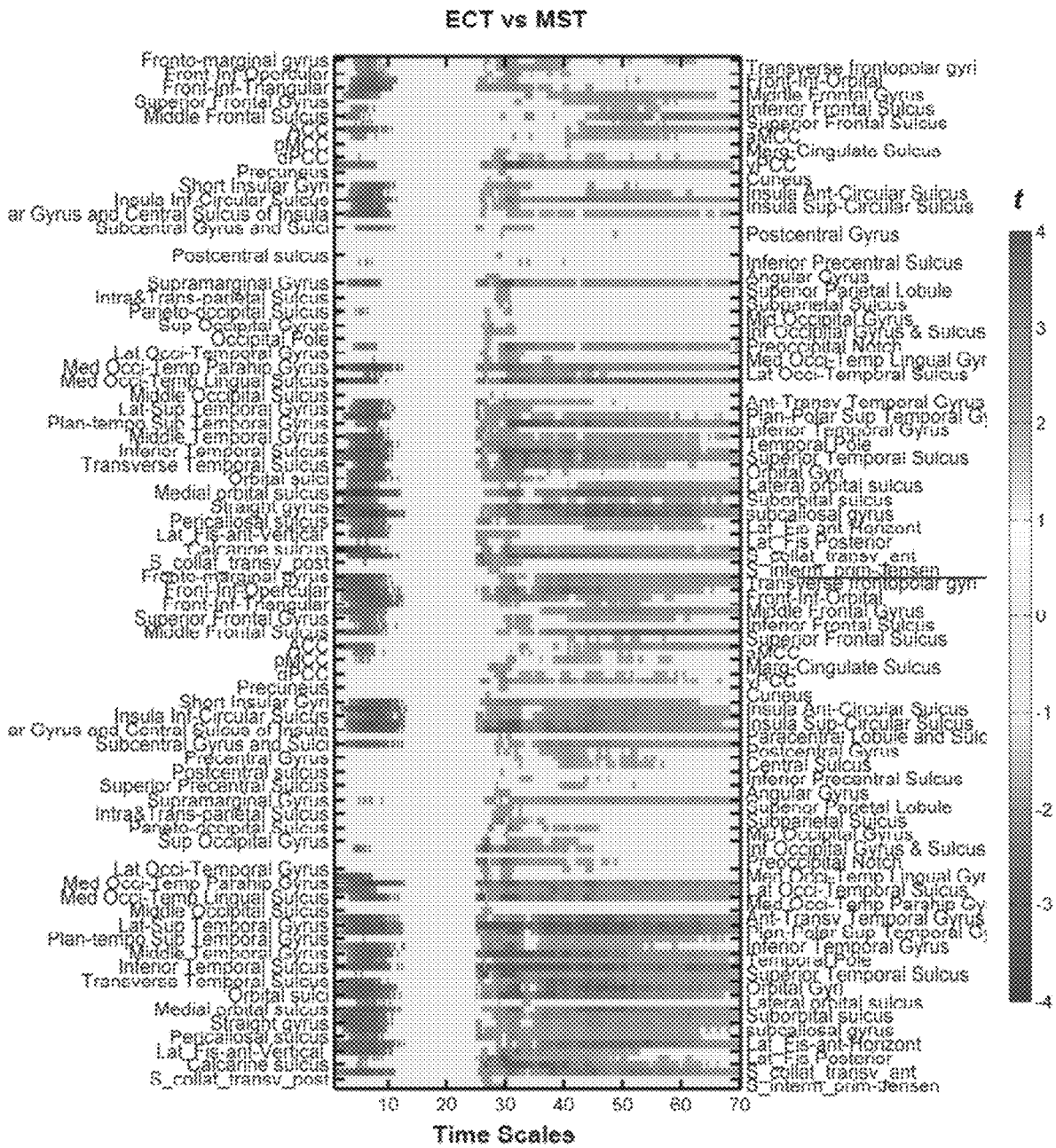
FIG. 2 depicts the Effect of Seizure Therapy on Complexity in the Source Space.

Finally, comparing ECT with MST intervention group, we identified MSE in fine time scales (e.g., <10) was significantly lower post treatment in ECT compared to MST group, and increases in coarse time scales (e.g., >2.8) were significantly higher in ECT compared to MST intervention group (FIG. 2A). This effect was spatially global. Comparing antidepressant responders with non-responders (FIG. 2B) identified significant differences between groups; however this finding did not survive the cluster-based correction for multiple comparisons. The comparison revealed that responders may have a larger reduction in MSE post treatment at finer time scales in brain regions such as the precuneus, bilateral cuneus, bilateral parieto-occipital sulcus, bilateral occipital pole, bilateral lateral occi-temporal gyrus, calcarine sulcus, and bilateral posterior transverse collateral sulcus. Responders also appeared to have increased MSE post treatment in coarser time scales (e.g., >40) mainly in the left inferior, middle and superior frontal sulcus, middle and superior frontal gyrus, and orbital part of inferior frontal gyrus. This latter observation is likely related to the higher number of ECT responders (compared to MST responders) who exhibited significant increases in complexity of those time scales (e.g., FIG. 1A).

The Impact of Change in Temporal Complexity on Mood and Cognition

Figure 5C:
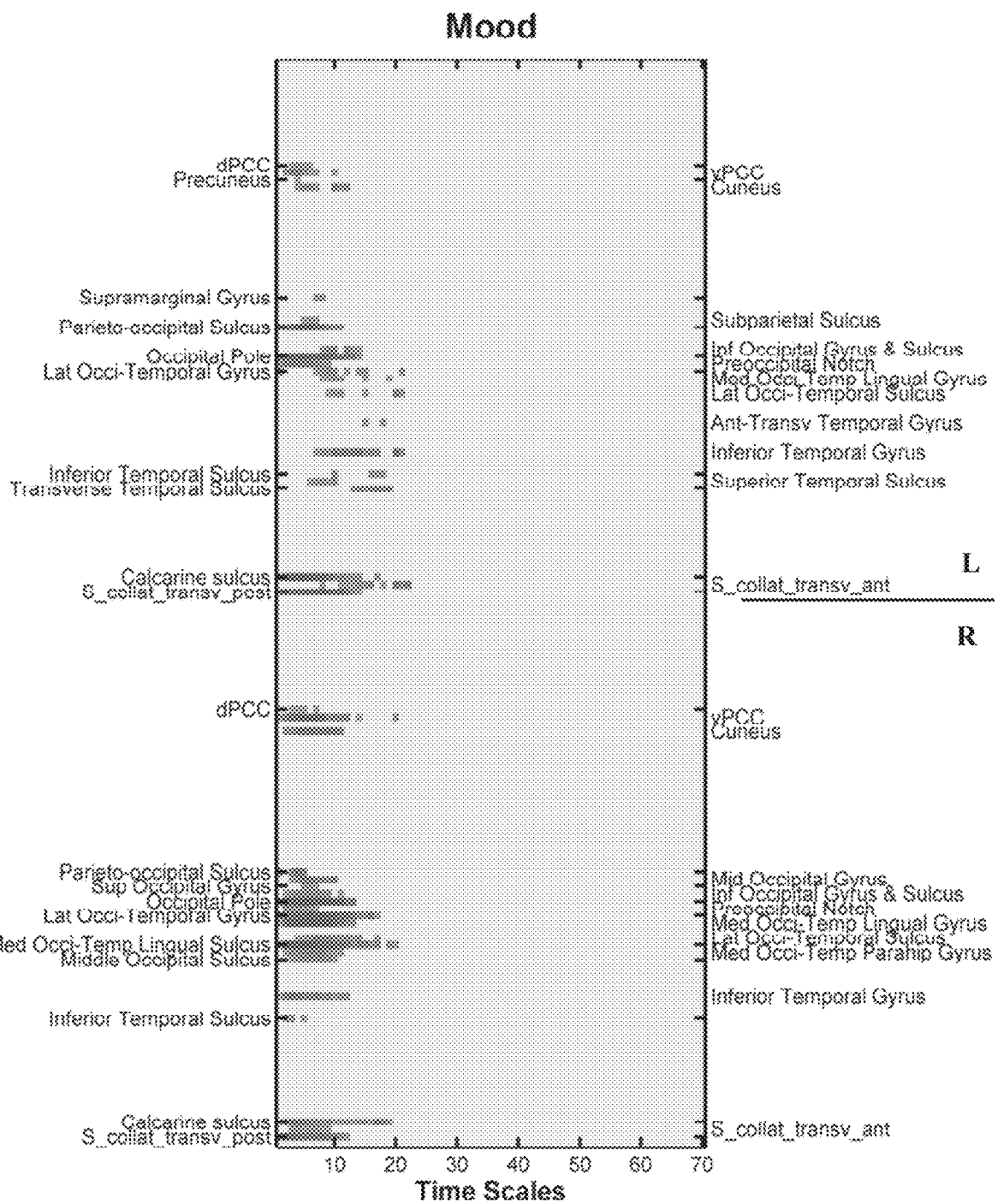

We then determined whether change in complexity was linked with the impact of seizure on mood and cognition. We found a negative association between percent changes in MSE (%ΔMSE) and percent change in HAMD (%ΔHAMD). This effect was selective to fine time-scales in parieto-occipital and fronto-central regions (FIG. 3A). Specifically, a negative association (p<0.01) was identified in tempro-parieto-occipital (TP7, P7, P5, P8, PO7, PO5, PO6, PO8, O1, O2, Oz) and fronto-central regions (AF4, F1, FZ, F2, F4, FC1, FC2, FC4, FCZ, C1, C4, CZ) in time-scales less than 30. Source space analysis localized this effect to several regions including the dPCC, cuneus, precuneus, parieto-occipital sulcus, occipital pole, temporal sulci, and lateral occi-temporal sulcus as depicted in FIG. 5C. This association illustrated that a spatially specific decrease in complexity of fine time-scales was linked with a greater improvement in depressive symptoms.

Moreover, we found a negative association between %ΔMSE and percent change in general cognition (%ΔMoCA). This effect was spatially global in coarse time-scales (e.g., >66) and included a wide range of time-scales in parieto-central regions (e.g., PZ, POZ, P1, P2) (FIG. 3B). Source-space analysis (FIG. 5D) confirmed that this effect was spatially global across coarse time scales and included brain regions such as intraparietal sulcus and transverse parietal sulci. This negative association was replicated for change in autobiographical memory (%ΔAMI) (FIG. S6A) and was prominent in bilateral fronto-parietal brain regions. Likewise, source space analysis revealed a spatially global effect in coarse time scales with many brain areas involved including the bilateral superior parietal sulcus, and superior temporal sulcus (FIG. S7A). Collectively, this negative association illustrated that an increase in MSE, in particular globally in coarser time-scales, was linked with a greater decline in cognition.

These findings were region- and time-scale specific. That is, change in complexity in occipital regions and fine time-scales was only associated with change in HAMD (e.g., O2 electrode, time-scale 4, r=−0.52, p=0.0017), and not change in MoCA (FIG. 3C), and change in complexity in parieto-central regions at coarser time-scale (e.g., PZ electrode, time-scale 70, r=−0.63, p=0.0038) was only associated with change in cognition, and not HAMD (FIG. 3D).

Classifying Antidepressant and Cognitive Response to Seizure Therapy

Figure 4:
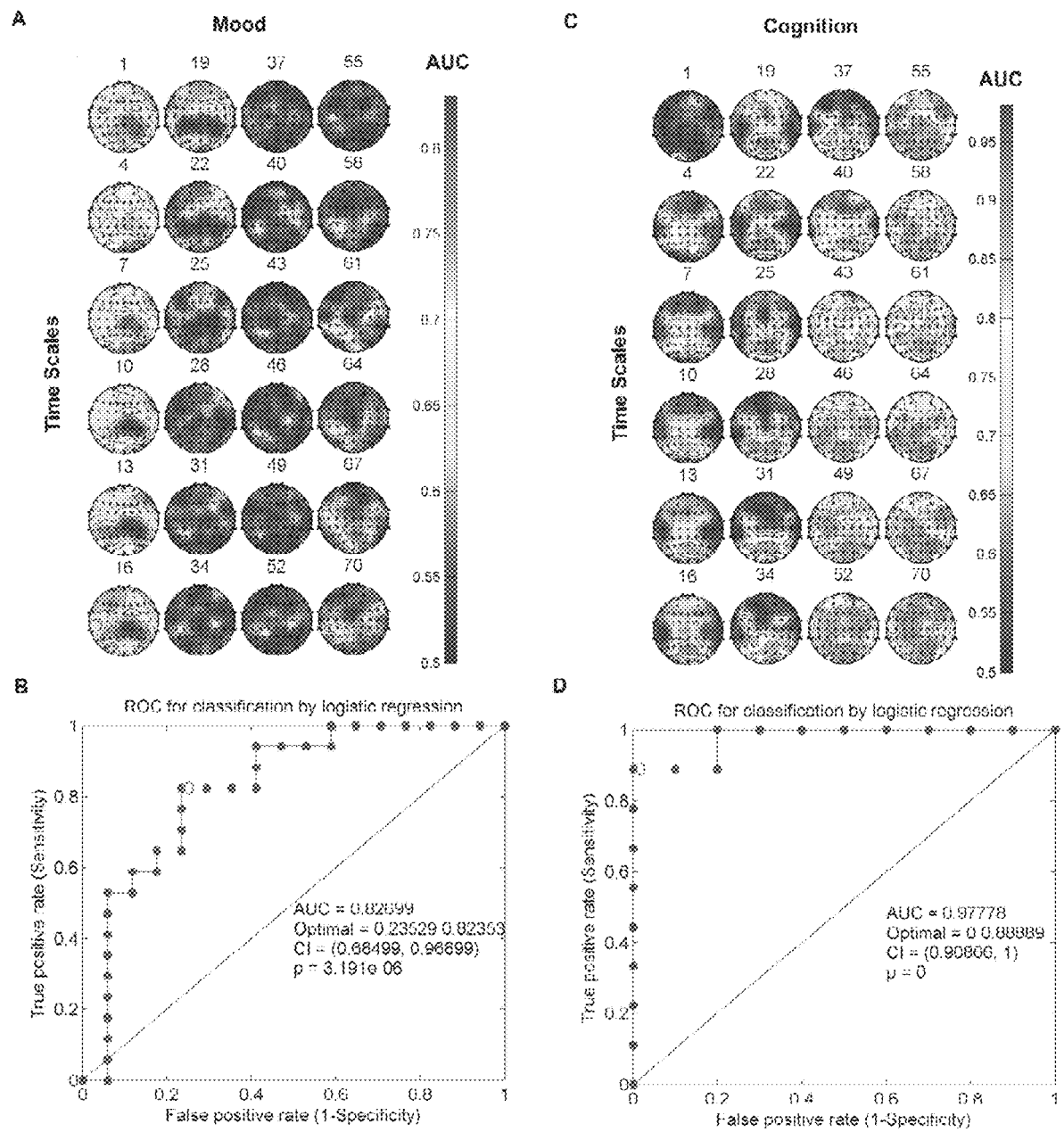
FIG. 4 shows a Region-Specific Change in Temporal Complexity Predicts Change in Mood and Cognition.
Figure 6A:
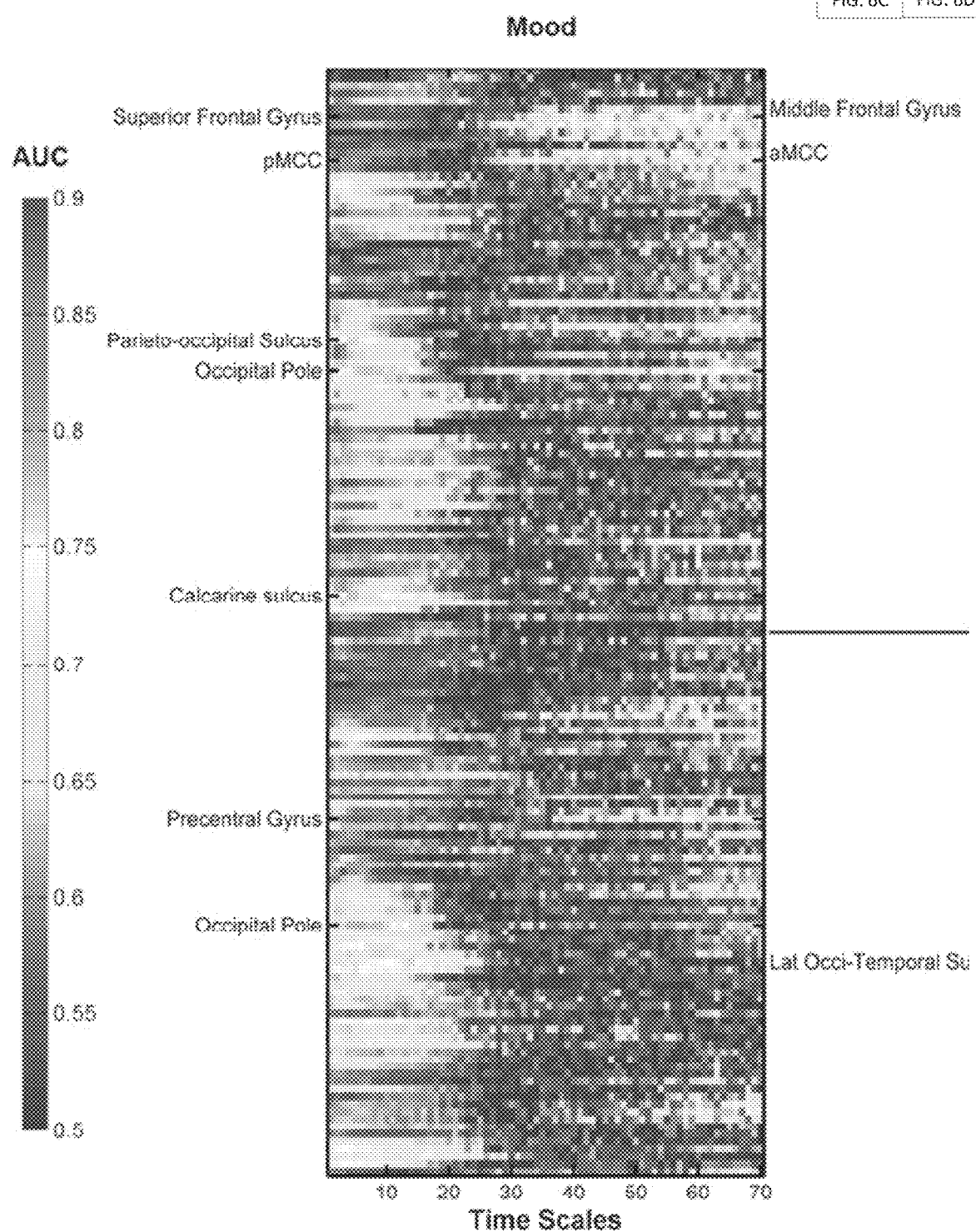
FIG. 6 shows a Prediction of Change in Mood and Cognition in the Source Space.

Finally, we examined whether change in temporal complexity could classify patients based on cognitive and antidepressant response to seizure therapy. We found that %ΔMSE classified the antidepressant response to seizure therapy with good performance and cognitive response with excellent performance as illustrated with the area under the curve (AUC) property of the receiver operating characteristic (ROC) curve (FIG. 4). Specifically, change in complexity of low time-scales (e.g., 4-6,8) in right parieto-occipital brain regions (OZ, O2, PO8) offered good (AUC≥0.8) prediction performance of antidepressant response ((e.g., AUC (OZ electrode, time-scale 5)=0.83, p<0.0001; FIG. 4A, B)) and a fair (0.7<AUC<0.8) prediction performance was observed across low time-scales (e.g., 1-22) in bilateral fronto-central (e.g., FC1, FC2, FCZ, F1) and bilateral parieto-occipital (e.g., O1, PO3, PO5, PO7, PO4, PO6, P7, P8) brain regions. In source space, similar prediction accuracy was identified for the right occipital pole at similar tune scale (AUC (right occipital pole, time-scale 5)=0.79, p<0.0001; FIG. 6A, B). Moreover, change in complexity of time-scales 14 and higher in parieto-central (e.g., PZ) and then globally in coarser time-scales provided excellent (e.g., AUC≥0.9) prediction performance for change in cognition (e.g., AUC (P2 electrode, time-scale 23)=0.98, p<0.0001; FIG. 4C, D). In source space, similar prediction accuracy was identified for the intraparietal sulcus and transverse parietal sulci at similar time scale (AUC (intraparietal sulcus transverse parietal sulci, time-scale 22)=0.97, p<0.00001; FIG. 6C, D).

These findings were region- and time-scale specific. That is, change in complexity in occipital regions and fine time-scales (e.g., OZ, time-scale 5; FIG. 4B) only classified antidepressant response, and did poorly in classifying cognitive response (AUC (OZ, time-scale 5)=0.55, p=0.35), and change in complexity in parieto-central regions at coarser time-scale (e.g., P2, scale 23; FIG. 4D) only classified cognitive response and did poorly in classifying antidepressant response (AUC(P2, time-scale 23)=0.47, p=0.63).

Moreover, the seizure therapy induced changes in autobiographical memory (%ΔAMI) could also be accurately (e.g., AUC range: 0.9 to 1.00; FIG. S6 B) classified by change in complexity in coarse time-scales (e.g., >47) in fronto-parietal regions (FIG. S6 B). Likewise, source space analysis revealed a spatially global effect in coarse time scales with many in frontal parietal brain regions (FIG. S7 B). Finally, our results showed that change in complexity had better accuracy than neural oscillations in predicting antidepressant or cognitive response to seizure therapy (FIG. S2 B, S3 B).

DISCUSSION

This study presented a novel biological target—i.e., complexity of the brain resting-state dynamics—whose modulation in specific brain regions explained the antidepressant efficacy and cognitive consequences of seizure therapy in depression. In contrast to neural oscillations, significant changes in the complexity of brain dynamics were only present in responders of seizure therapy. Specifically, complexity of fine time-scales was significantly reduced following successful ECT and MST. Across groups, the greater reduction in complexity of fine time-scales in fronto-central and parieto-occipital regions (e.g., right occipital pole) was associated with greater improvement of depressive symptoms. In ECT, the complexity of coarse time-scales was also significantly increased. Across groups, the greater global increase in complexity of coarse time-scales was linked with the greater decline in general cognition. Finally, region- and time-scale dependent changes in complexity classified patients based on antidepressant efficacy (e.g., in right occipital pole, scale 5) and cognitive consequences (e.g., intraparietal sulcus and transverse parietal sulci, scale>22), of seizure therapy with good (>80%) and excellent (>90%) accuracy, respectively.

ECT remains the most effective treatment in depression. Several hypotheses have attempted to explain the mechanism of action of ECT (reviewed in (Farzan et al., 2014)). We recently proposed a unifying connectivity-resettling hypothesis, stating that ECT resets aberrant neural connectivity by activating the brain's major oscillatory pacemaker, thalamus and subsequently multiple thalamic loops (Farzan et al., 2014). The significant impact of seizure therapy on neural oscillations has been quantified since early studies of ECT (reviewed in (Farzan et al., 2014)). The most replicated finding is the general slowing of oscillations in ECT (Small et al., 1978) linked with improvement in mood (Fink and Kahn, 1957; Sackeim et al., 1996). While we replicated previous findings demonstrating that ECT induces increase in power of slow oscillations, this effect was present in both ECT responders and non-responders. Moreover, we found no correlation between change in slow oscillations and improvement in symptoms. Most previous studies focused on limited and predefined frequency bands, using a few electrodes placed near the site of stimulation, or utilized statistical approaches that limited multidimensional analysis. The present study used non-parametric statistical approaches and two distinct modalities of seizure induction to comprehensively assess changes common to seizure therapy without a priori hypothesis or limiting analysis to regions and frequencies of interest. Our comprehensive analysis revealed that it is the reduction in relative power of frequencies 18 Hz and above, particularly higher than 35 Hz, rather than increase in slow oscillations, that is linked with response to seizure therapy across ECT and MST. The observation that successful MST modulated high frequencies without significantly impacting slow oscillations further confirms that successful seizure therapy may be achieved without impacting the slow oscillations that are linked with the adverse effects of ECT as reported previously (Sackeim et al., 2000; Nobler and Sackeim, 2008) and replicated in our study.

The pre-ietal characteristic of seizure reflects a rapid modification of the brain dynamicity. It seems intuitive that modulation of the brain dynamics would be a mechanism by which seizure exerts its therapeutic action. Yet this has been only minimally investigated. In an ECT case study in three patients with depression, reduction in MSE in fine time-scales was reported (Okazaki et al., 2013). Our results are also in line with a previous study that showed an abnormal enhancement in complexity of frontal brain regions in depression which was normalized by antidepressant medication (Mendez et al., 2012). Complexity, as indexed by Lempel-Ziv Complexity, was increased as a function of age in healthy subjects, a relationship not found in depression. Furthermore, six months of treatment with the antidepressant mirtazapine normalized the excess complexity in depression specifically in younger adults (Mendez et al., 2012). Such findings may suggest that both medications and seizure therapy act on reducing complexity in depression, while the higher efficacy of seizure therapy may be linked to direct stimulation of oscillatory pacemakers. We found that antidepressants efficacy of seizure therapy was linked with local changes in complexity. Our findings and these previous studies encourage design of non-seizure interventions that target the same biological targets as seizure therapy toward eliminating the risk and complications of seizure induction.

Complexity of time series in biological systems is suggested to reflect plasticity to an ever changing environment and adaptability to stressors (McIntosh et al., 2014). When examined across brain regions and time-scales, the complexity of brain dynamics can arise from transient increases and decreases in correlated activity across brain regions reflecting rate of information generation (McIntosh et al., 2014). Induction of seizure could reset integration and synchronization of information across brain regions, through activation of thalamus and multiple thalamic loops and interconnected brain regions, significantly impacting rate of information generation across distributed brain networks. The association between reduction in complexity and improvement in symptoms is in line with imaging findings that have shown that depression is associated with states of hyperconnectivity between frontoparietal and default mode network (Kaiser and Pizzagalli, 2015). The clinically relevant reduction of complexity in fronto-central and parieto-occipital regions adds to the resting-state functional connectivity findings in fMRI literature.

A recent study using fMRI data from Human Connectome Project showed differential association between functional connectivity of resting-state networks and complexity of fMRI time signals in fine versus coarse time-scales (Mc-Donough and Nashiro, 204). The time-scales in this fMRI study are coarse in comparison to the present high resolution EEG study, hindering direct interpretation. Yet, it provides evidence that there may be a link between seizure-induced changes in complexity and aberrant neural connectivity in depression. We suggest that a change in dynamics of functional connectivity between distributed brain regions may be a mechanism by which seizure therapy exerts its impact on behaviour. Design of non-invasive interventions that can selectively modify the complexity of the brain dynamics will enable careful examination of the consequence of region- and network-specific modification of MSE on human behaviour.

Moreover, the finding that seizure induced changes in the occipital lobe (e.g., occipital pole) were linked to mood improvement and predicted therapeutic response is also in line with several lines of emerging evidence that have linked depression with impairment in this brain region (reviewed in (Koch and Schultz, 2014)). For example, as reviewed by Koch et al, a recent meta-analysis reported the right occipital lobe, with the inferior fronto-occipital fibre tract, to be among the most consistently reported site of decreases white matter integrity in this population. Furthermore, in addition to the changes in white matter structure, changes in resting-state connectivity and gray matter volume have been previously shown in this brain region in depression (e.g., (Grieve et al., 2013; Meng el al., 2014)). Moreover, a recent study has reported that occipital bending is more common in depression (Mailer et al., 2015). Finally, a prior study in post-stroke depression have identified that post-stroke depression was closely linked with the right hemisphere lesion volume and its proximity to the occipital pole (Shimoda and Robinson, 1999). Therefore, our finding that seizure therapy may exert its antidepressant efficacy by impacting the dynamics of the occipital region, particularly source localized so the occipital pole, not only complements these prior findings, but also provides a direction for development of novel antidepressant treatments.

This study also adds new insight about the link between region- and time-scale dependent changes of complexity and human behavior. We illustrated a region-specific reduction of MSE in fine time-scales that was linked with improvement in mood, and a more spatially-distributed (e.g., bilateral fronto-parietal) increase of MSE in coarse time-scales that was linked with cognitive decline. Previous studies have reported both global and region-specific modulation in complexity, such as during development (Misic et al., 2010) and aging (McIntosh et al., 2014), respectively. Indeed, the observed link between increase in MSE in coarse time-scales and cognitive decline is consistent with findings in Alzheimer's disease (Mizuno et al., 2010). Our findings also extend previous studies that revealed significant modifications in this marker during adolescence (Vakorin et al., 2014), when the prevalence rate of depression peaks, and in disorders of cognition and affect with overlapping symptoms with depression including autism spectrum disorder (Bosl et al., 2011) or schizophrenia (Takahashi et al., 2010) in which seizure therapy is also indicated.

MST treatment frequency may be an important dimension involved in production of a seizure. The majority of prior MST trials have applied MST at 100 Hz frequency to achieve seizure induction. However, it was proposed that the optimal frequency for seizure induction may be in the vicinity of 22 Hz (Peterchev et al., 2010). In our sample, the most common MST frequency used was 100 Hz (in 12/15 subjects), while a few patients who also took part in the resting-state EEG assessments received lower frequency of stimulation to induce seizure. Nevertheless, the present EEG study was not designed to evaluate the impact of different frequency of stimulation on therapeutic outcome. We propose that the markers presented in this study have the potential to be used to protect against any potential cognitive adverse effects through neurophysiological monitoring that may predate any cognitive deterioration.

Finally, out finding support a focal antidepressant target for seizure therapy. First, the association between change in MSE and depressive symptoms was identified in fronto-central and parieto-occipital electrodes and source localized to several parieto-occipital brain regions including the occipital pole. Second, the reduction in MSE was observed more localized to these brain regions in fine time-scales in responders in MST which is a more focal method of seizure induction. Consistently, the association between change in neural oscillations and depressive symptoms was also localized to fronto-central and parieto-occipital brain regions and high frequency oscillations that correspond to fine time-scales. Fourth, the classification performance of the change in complexity was region- and time-scale specific. Brain regions at which change in complexity classified antidepressant response with good accuracy failed to classify cognitive response, and brain regions at which change in complexity classified cognitive response failed to classify antidepressant response. Recent evidence indicates the possibility of modulating the temporal complexity of brain signals by network guided rTMS (Farzan et al., 2016). Therefore, treatment of depression may benefit from design of more localized seizure induction strategies or non-seizure treatments (e.g., rTMS) that could focally modulate complexity.

Example 1: Escitalopram (Non-Seizure, Pharmacological Antidepressant) Brain Temporal Complexity Throughout 8 Weeks of Escitalopram Therapy Material and Methods 95 participants were included in this study. Data were collected as part of the CAN-BIND 1 project (Lam et al., 2016). Participants were outpatients aged 18-60 years of age, and met DSM-IV-TR (2000) criteria for major depressive episode (MDE) in MDD, confirmed by the Mini international Neuropsychiatric inventory (MINI) (Sheehan et al., 1998). Data were gathered across four study sites: University Health Network, Centre for Addiction and Mental Health in Toronto, Queen's University in Kingston, Ontario, Canada, and University of British Columbia in Vancouver, British Columbia, Canada. Study procedures were approved by research ethics institutional review boards at each site. All participants signed written informed consent prior to participation. At study enrollment, all participants were experiencing a MDE duration$\geq 3$ months with a Montgomery Asberg Depression Rating Scale (MAD RS) score$\geq 24$. All participants were free of psychotropic medications for at least 5 half-lives before baseline Visit 1. Participants were excluded if they had: 1) any Axis I diagnosis other than MDD, that was considered the primary diagnosis; 2) diagnosis of Bipolar Disorder Type I or II; 3) a significant Axis II diagnosis (borderline, antisocial); 4) high suicidal risk, 5) substance dependence/abuse in the past 6 months; 6) presence of significant neurological disorders, 7) head trauma, or 8) other unstable medical condition. Exclusionary criteria related to the medications included: having failed four or more adequate pharmacological interventions, having started psychological treatment within the past 3 months with the intent of continuing the treatment, previously having failed escitalopram treatment or showing intolerance to escitalopram, and being at risk for hypomanic switch (i.e. with a history of antidepressant induced hypomania). In addition, female participants who were pregnant or breastfeeding were excluded. Finally, participants were excluded from this study if they were lost to attrition before study baseline, discontinued in the middle of the treatment, or did not complete all EEG and clinical assessment visits.

Clinical Measures

The study period was eight weeks and participants were assessed with MADRS every 2 weeks starting from before administration of study medication (baseline). Response was defined as a>50% decrease in MADRS score from baseline to week 8.

Treatment Trial

Treatment was administered in an open-label manner. Escitalopram dosing was started at 10 mg daily and increased to 20 mg daily at week 2 or later if clinically necessary. The dose could be reduced to 10 mg at the discretion of the treating psychiatrist if patients were unable to tolerate the 20 mg dose.

EEG Recording

Subjects were instructed to sit quietly in a testing room, while 8 minute of resting-state eyes closed EEG were recorded. Subjects were instructed to remain still, reduce eye blinks or movement to a minimum, and refrain from falling asleep. Four EEG acquisition systems were used across study sites as described in details elsewhere (see Baskaran et al., 2017, and Farzan et al., 2017).

EEG Preprocessing. Data were imported into MATLAB (The Math Works. Inc. Natick, MA, USA) for preprocessing. The open source EEGLAB toolbox version 12.0 (Delorme and Makeig, 2004) were used for data import. The EEG signals were epoched into segments of two seconds duration. Then a standardized custom-made and stream-lined open source software develop by our team, EEGERP toolbox (http:www.tmseeg.com/multisiteprojects), was used to preprocess the data in 6 steps as described elsewhere (Farzan et al., 2017). All data were brought down to sampling rate of 512 Hz for consistency across all sites, and average re-referenced in the final preprocessing step.

Power. The EEGLAB function spectopo was used to obtain the power spectrum for each electrode. The relative power was obtained for 1 to 50 Hz frequencies. Relative power was calculated as the ratio in the power of each frequency relative to the sum of power across all frequencies.

Multi-Scale Entropy. MSE was examined identical to a prior publication (Farzan et al., Brain 2016). Identical to this prior publication: "MSE was obtained across all electrodes using two steps (Costa et al., 2005): The coarse-graining process and the calculation of the sample entropy (SampEn) for each coarse-grained time series. First, for a given time series $\{x_1, x_2, \ldots x_N\}$, the multiple coarse-grained time series $\{y_1^{(\tau)}, y_2^{(\tau)}, \ldots, y_N^{(\tau)}\}$ at scale factor $\tau$ were calculated by averaging the data points within non-overlapping windows of increasing length $\tau$. Each element of the coarse-grained time series $y_j^{(\tau)}$, was calculated according to the equation:

$$y_1^{(\tau)} = \frac{1}{\tau} \sum_{i=(j-1)\tau-1}^{j\tau} x_i \qquad (1)$$

where $\tau$ represents the scale factor and $$j\left(1 \leq j \leq \frac{N}{r}\right)$$

represents the time index of the element.

The length of each coarse-grained time series was M, where $$M = \text{floor}\left(\frac{N}{r}\right).$$

At scale factor $\tau=1$, the coarse-grained time series was the original time series. Second, the degree of predictability was measured for each of the multiple coarse-grained time series $\{y_1^{(\tau)}, y_2^{(\tau)}, \ldots, y_N^{(\tau)}\}$ using SampleEn. SampleEn was calculated according to the equation:

$$\text{SampleEn}(r,m,M) = -ln(C(m+1)/C(m)) \qquad (2)$$

where C(m) is the total number of pairs of in consecutive similar data points, C(m+1) is the total number of pairs of m+1 consecutive similar data points in the multiple coarse-grained time series. SampleEn quantifies the variability of time series by estimating the predictability of amplitude patterns across a time series. In our experiments, two consecutive data points were used for data matching (i.e. m=2) and data points were considered to match if their absolute amplitude difference was less than 15% (i.e., r=0.15) of standard deviation of time series. MSE was calculated for a 30 second continuous epoch."

EEG Source Localization. We used the Destrieux Atlas available as a part of an open-source application, Brainstorm (Destrieux et al., 2010; Tadel et al., 2011), to localize the dynamics of neural activity. The Destrieux atlas provides 148 Region of Interests (ROIs) in the MNI co-ordinate space. Source estimation was performed using sLORETA (Pascual-Marqui, 2002) as implemented in Brainstorm. Source reconstruction was constrained to the cortex surface of the OpenMEEG BEM head model (Gramfort et al., 2010). After the data was mapped to 148 ROIs in the source space, MSE and power spectrum measures were calculated for all subjects at these sources.

Statistics

Subjects were grouped into two groups of antidepressant responders and non-responders according to previous literature: subjects were grouped as responders if there was a 50% or higher change in MADRS at week 8 relative to baseline, and non-responders otherwise. Analysis of variance was used to 1) examine the effect of medication on MSE (1-70 time-scales) and relative power (1-50 Hz frequencies) for the main effect of Time (Baseline, week 2, week 8), as well as 2) Antidepressant Response (Responder, Non-Responder) and Time (Baseline, week 2, week 8) across 58 electrodes in sensor space and 148 ROIs in source space. Cluster-based non-parametric permutation test (Maris and Oostenveld, 2007) was used to correct for the multiple comparisons in this multidimensional dataset (58 channels (or 148 ROIs)× 50 frequencies, 58 channels×70 scales) by assigning significance statistics to the probability of size of clusters formed by pooling adjacent pixels with original test statistics $p<0.05$. Identical parameters were used in the cluster-based permutations: threshold statistics of $p<0.05$, identical neighborhood matrix, 1000 permutation using Monte Carlo approach with cluster test statistics computed as the maximum of the cluster-level summed values. Analysis of variance and post-hoc paired t-test and independent sample t-test analyses were used to calculate the original test statistics. The significance of original clusters was defined against probably distribution of clusters obtained through 1000 permutations of the shuffled data labels. Spearman correlation coefficient was used to examine the association between change in complexity and symptom severity. Similarly, cluster-based non-parametric permutation test was applied to MADRS scores to correct for the multiple comparisons in the correlation analyses.

In addition to correlation analysis, it was examined if change in complexity classified patients based on antidepressant response. The level of prediction was quantified by the receiver operating characteristic (ROC) curve, plotting the sensitivity and specificity of the predictor (change in complexity) across all possible threshold values. To determine the significance of the prediction, the area under the curve (AUC), standard error of the AUC and confidence intervals were quantified for each electrode.

Throughout the paper, except otherwise noted, reported statistics are corrected p values, and descriptive values indicate mean and standard deviation unless otherwise stated. Percent change (i.e., %Δ) in outcome variables is calculated as: (post treatment score−baseline score/baseline score)×100, except for MADRS which is calculated as (baseline score−post treatment)×100.

RESULTS

TABLE 2

| | All Groups (n = 95) | Responders (n = 45) | Non-responders (n = 50) |
|---|---|---|---|
| Age (mean +/− std) | 36 +/− 12.4 | 36.2 +/− 12.7 | 35.8 +/− 12.2 |
| Gender (F/M) (n) | 63/32 | 30/15 | 33/17 |
| MADRS Baseline (mean +/− std) | 30.0 +/− 6.09 | 29.9 +/− 6.15 | 30.2 +/− 6.10 |
| MADRS Post Week8 (mean +/− std) | 15.4 +/− 9.7 | 7.62 +/− 5.24 | 22.3 +/− 7.18 |

Figure 14:
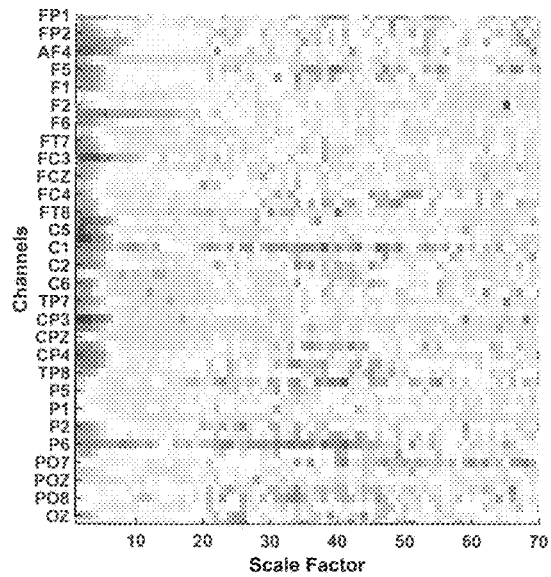
FIG. 14 shows the Effect of Escitalopram on Complexity of Temporal Dynamics.
Figure 14:
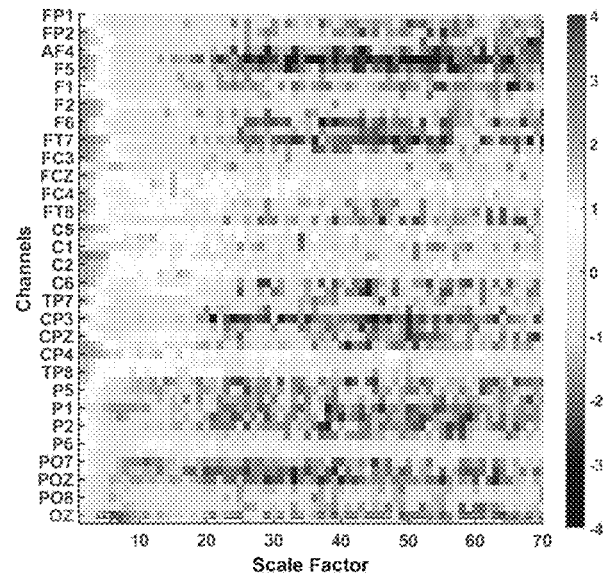
Figure 14:
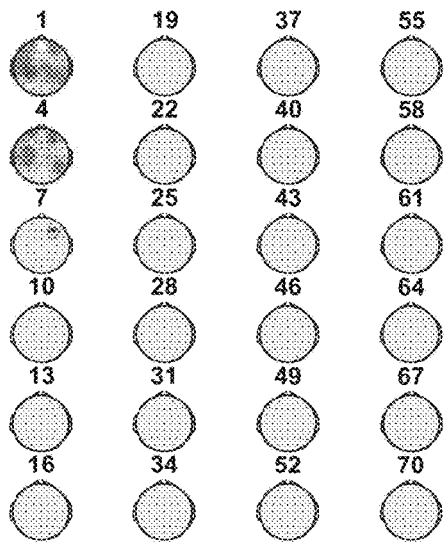
Figure 14:
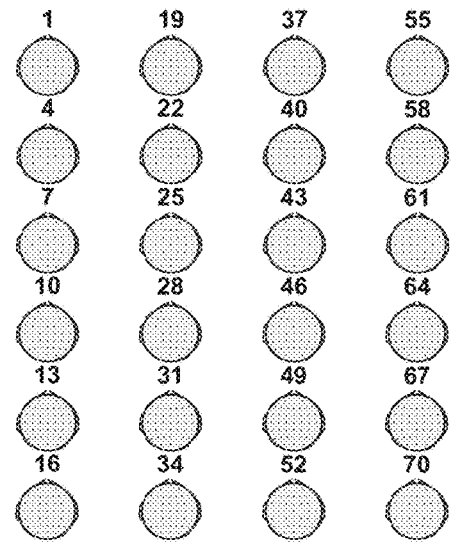

FIG. 14 shows effect of Escitalopram on Complexity of Temporal Dynamics. Top: Images show the original post-hoc test statistics comparing MSE pre (baseline) to post treatment (week 8) across all electrodes (1 to 58) and all time-scales (1 to 70) (blue: increases; red: decreases following treatment) for responders (left) and non-responders to escitalopram (right). Bottom. Each topography reflects the significant t-maps following correction for multiple comparison, using cluster-based non-parametric permutation test for p=0.05, depicting only the clusters p<0.09 and setting to 0 other pixels. Topographies highlight the spatial characteristics of the reduction of MSE in fine time-scales in responders to escitalopram in fronto-parietal brain regions (cluster p=0.09). No significant changes were observed in non-responders.

Figure 15:
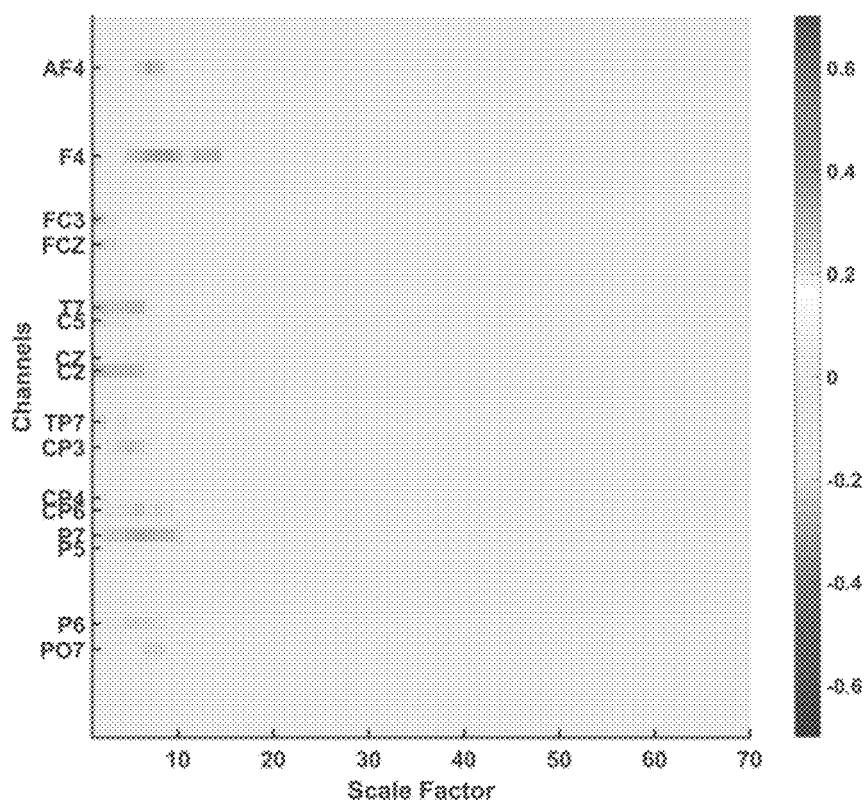
FIG. 15 shows an Association between Modulation of Temporal Complexity and Mood.
Figure 15:
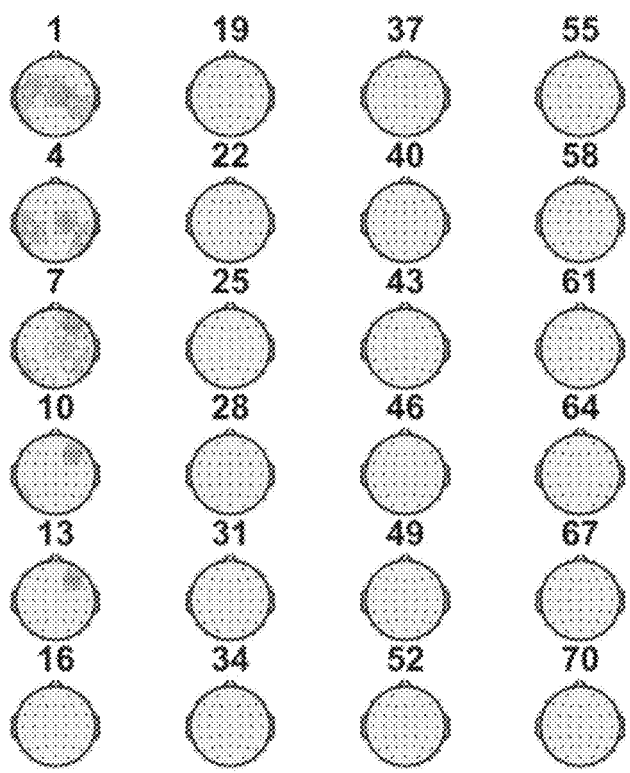

FIG. 15 shows association between Modulation of Temporal Complexity and Mood. Top: Image illustrate all the significant (original p<0.05) spearman correlation coefficients (rho) between percent change in MADRS and change in MSE (pre-post) in 95 patients receiving escitalopram therapy. Cluster-based correction for multiple comparison resulted in significant clusters (p<0.05) in parieto-occipital and frontocentral regions in time-scale less than 10 factors. Bottom: Topographies illustrate spatial distribution of this association.

Figure 16:
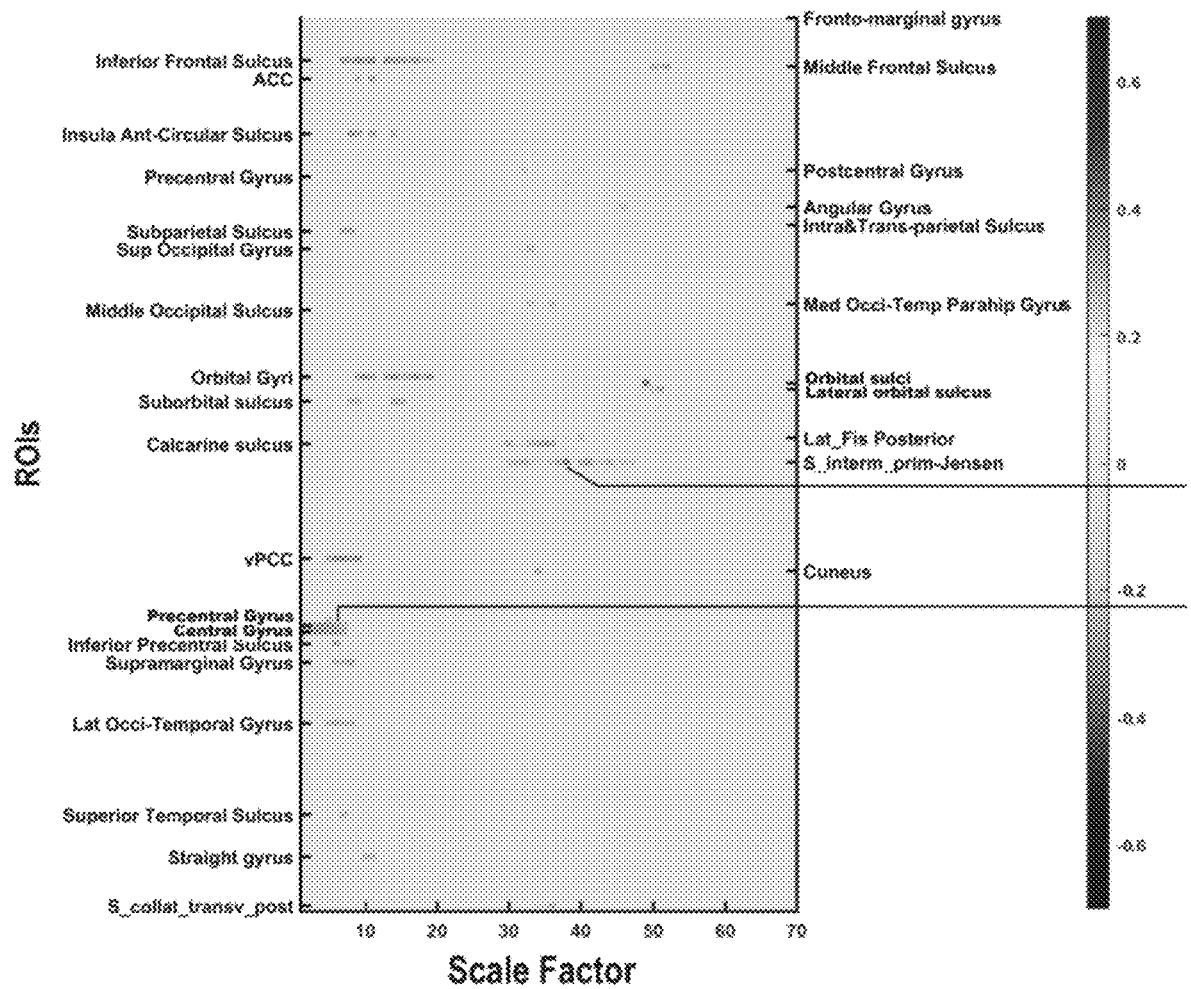
FIG. 16 shows Escitalopram Induced Modulation of Complexity and Its Association with Mood in Source Space.
Figure 16:
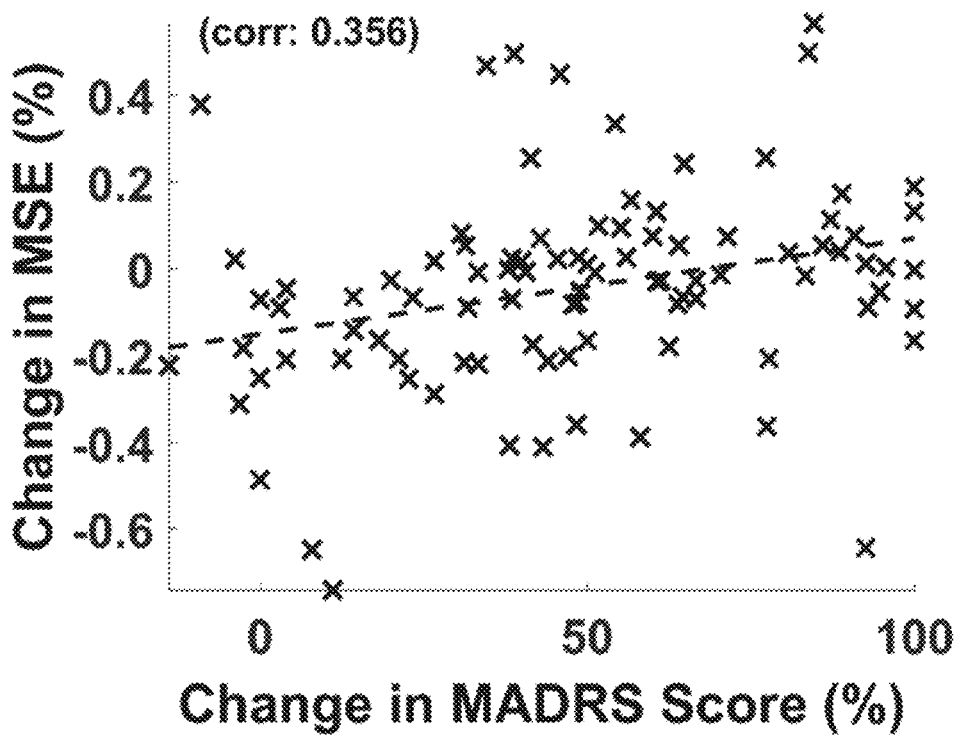
Figure 16:
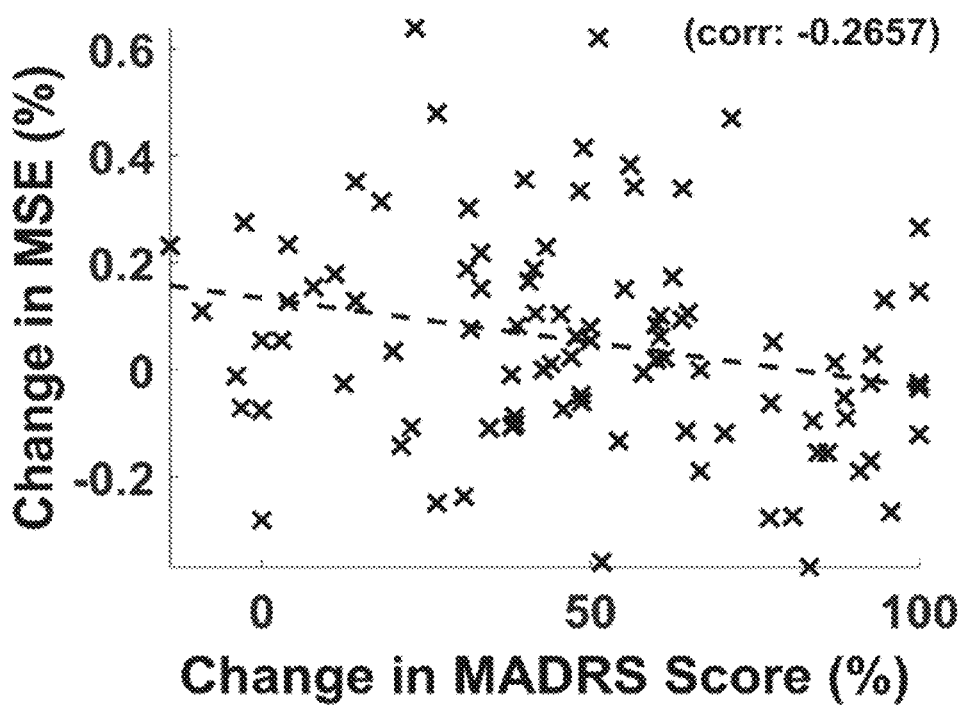

FIG. 16 shows Escitalopram Induced Modulation of Complexity and Its Association with Mood in Source Space. In left image, x-axis represents the time scales (1 to 70) and y-axis represents Regions of Interest (ROIs) of the Destrieux Atlas (1 to 148). Images show the post-hoc test statistics following cluster-based permutation test correction for multiple comparison, depicting only the significant clusters p<0.05, labeling only the significant corresponding ROL and setting to 0 non-significant pixels. Scatter plots show that only region-specific reduction in MSE in fine time-scales (less than 20 time scales) was significantly associated with enhancement of MADRS.

Figure 17:
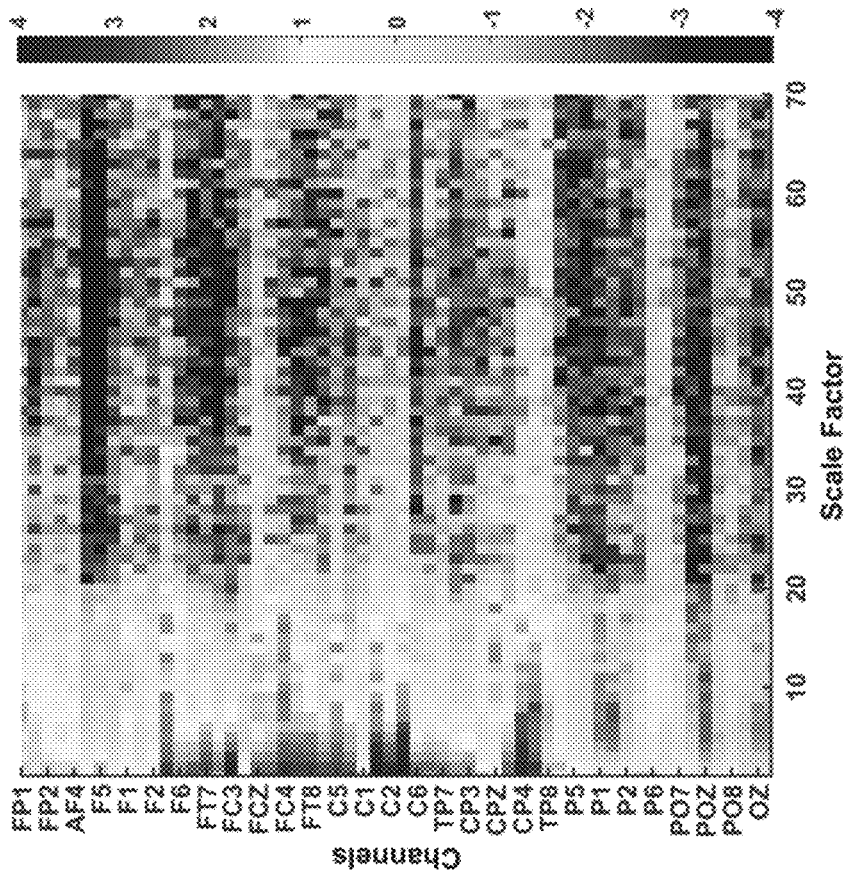
FIG. 17 shows a Differential Early Changes in Complexity of Temporal Dynamics during Escitalopram Treatment in Responders and Non-Responders.
Figure 17:
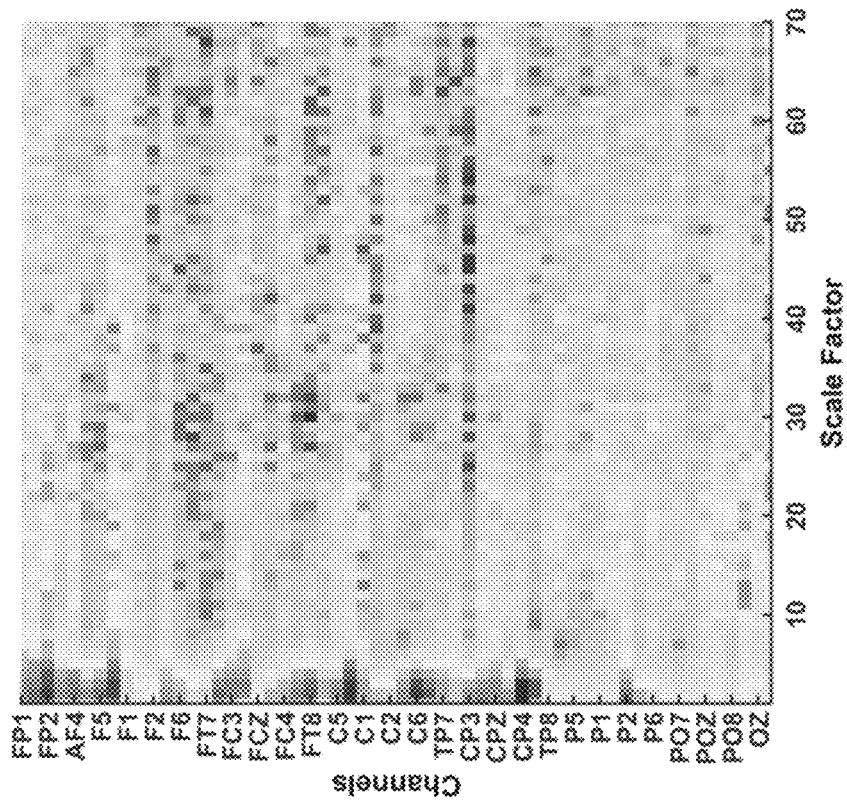
Figure 17:
Figure 17:
Figure 17:
Figure 17:
Figure 17:
Figure 17:
Figure 17:
Figure 17:
Figure 17:
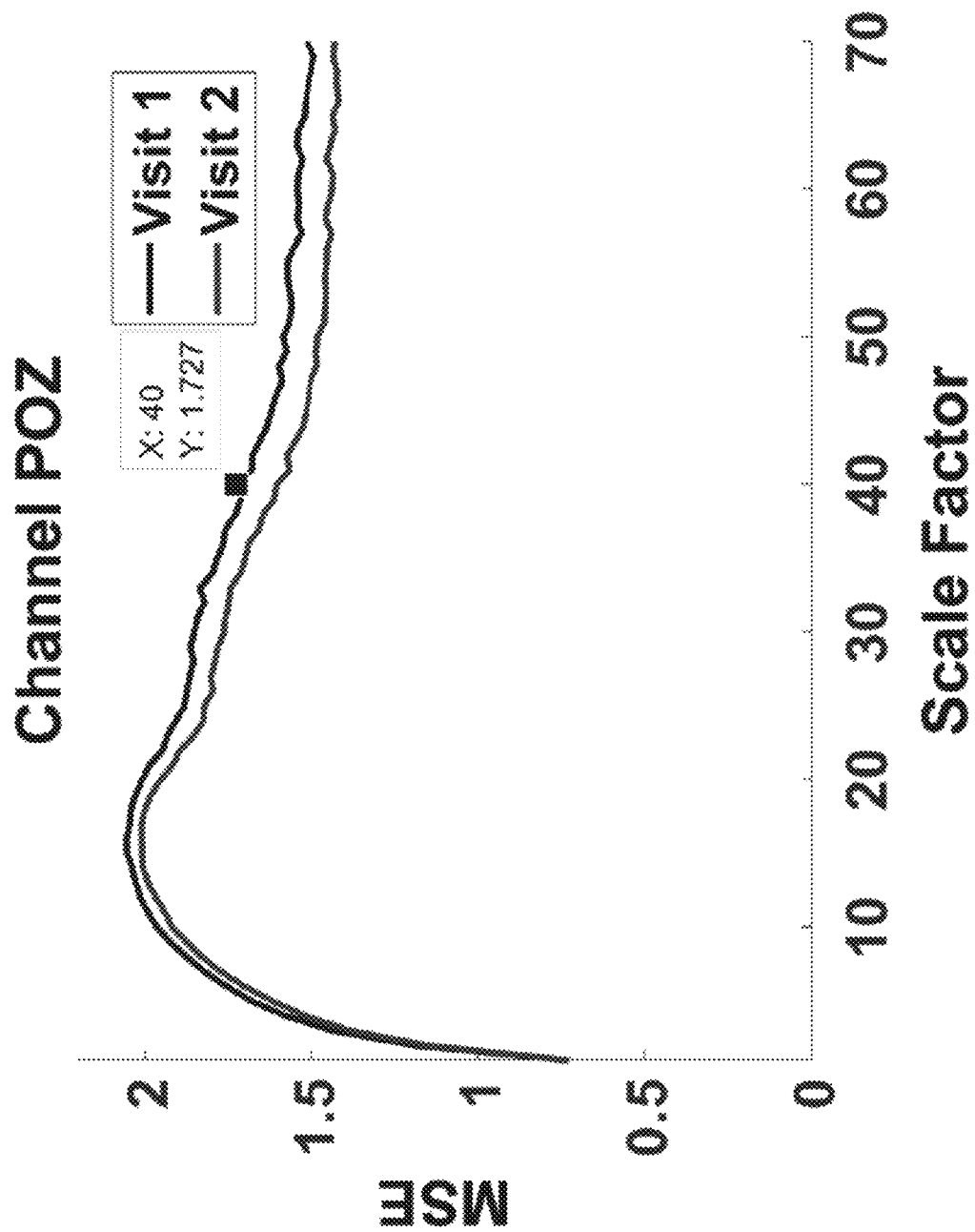

FIG. 17 shows differential Early Changes in Complexity of Temporal Dynamics during Escitalopram Treatment in Responders and Non-Responders. Top: Images show the original post-hoc test statistics comparing MSE at week 2 relative to pre treatment (baseline) across all electrodes (1 to 58) and all timescales (1 to 70) (blue: decreases; red: increases following treatment) for responders (Left column) and non-responders (Right column) from baseline to week 2. Bottom: Each topography reflects the significant t-maps following correction for multiple comparison, using cluster-based non-parametric permutation test, depicting only the significant clusters p<0.05 and setting to 0 non-significant pixels. Topographies highlight the spatial characteristics of the reduction of MSE in coarse time-scales in non-responders. The reduction of MSE in coarse time-scales (e.g., scale factor>18) was localized to lateral frontal, fronto-temporal, and parieto-occipital brain regions. No significant changes were observed in non-responders.

Figure 18:
FIG. 18 shows a Source Localization of Early Changes in Temporal Complexity in Non-Responders to Escitalopram.

FIG. 18 shows source Localization of Early Changes in Temporal Complexity in Non-Responders to Escitalopram. X-axis represents the time scales (1 to 70) and y-axis represents Regions of Interest (ROIs) of the Destrieux Atlas (1 to 148). Images show the post-hoc test statistics following cluster-based permutation test correction for multiple comparison, depicting only the significant clusters p<0.05, labeling only the significant corresponding ROIs and setting to 0 non-significant pixels.

Figure 19:
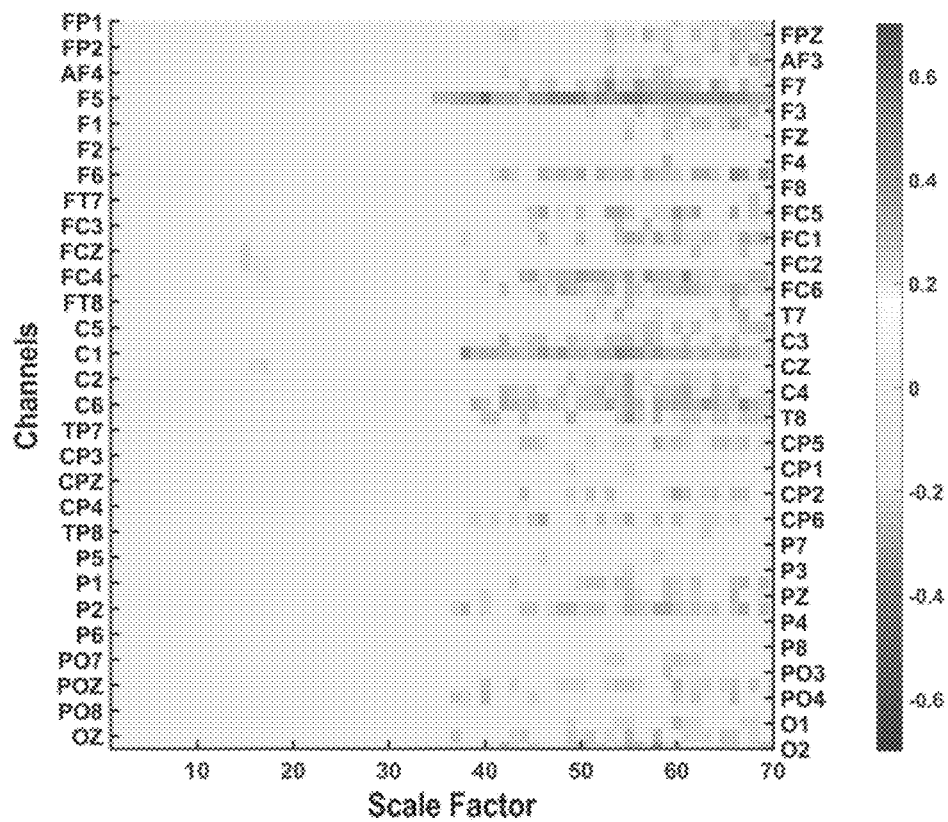
FIG. 19 shows the Link Between Baseline Complexity and Change in Mood by Escitalopram.
Figure 19:
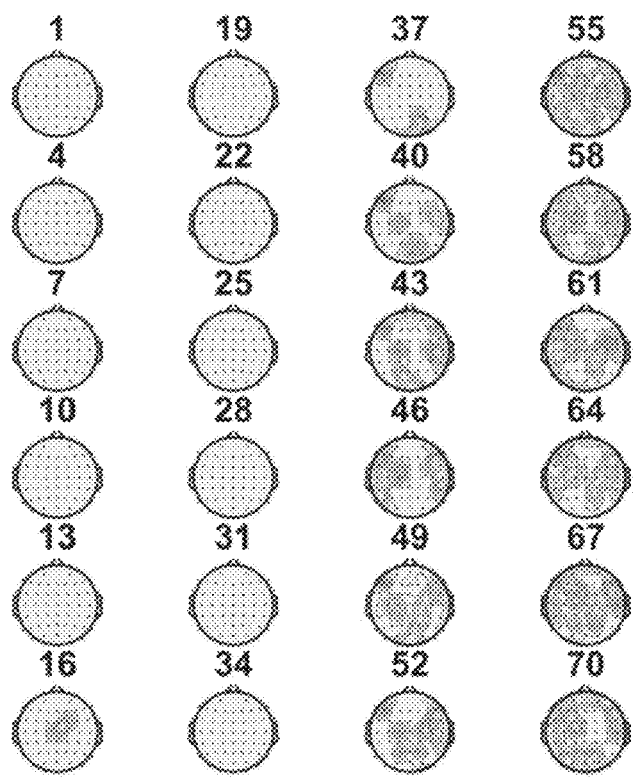

FIG. 19 shows link Between Baseline Complexity and Change in Mood by Escitalopram. Top: Image illustrate all the significant (p<0.05) spearman correlation coefficients (rho) between percent change in MADRS (week 8 to baseline) and baseline MSE (pre-post) in 95 patients receiving escitalopram therapy. Cluster-based correction for multiple comparison resulted in significant clusters (p<0.05) across multiple brain regions (global) such as in parieto-occipital and fronto-central regions in time-scale higher than 37. Bottom: Topographies illustrate spatial distribution of this association.

Figure 20:
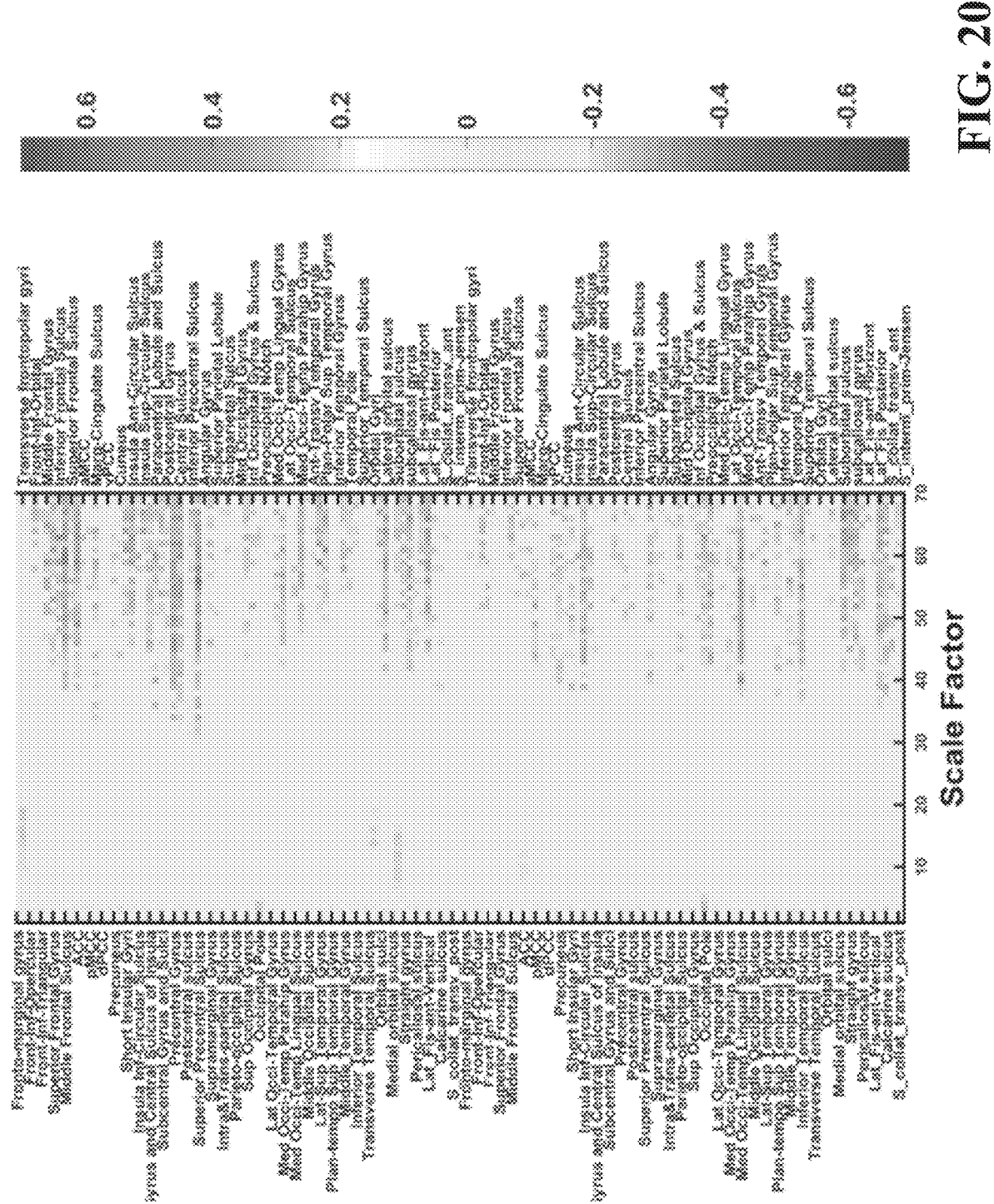
FIG. 20 shows the Link between Baseline Complexity and Change in Mood by Escitalopram Source Space.

FIG. 20 shows link between Baseline Complexity and Change in Mood by Escitalopram in Source Space. Source analysis of data from prior figure reflects all brain region whose baseline complexity is associated with change in depressive symptoms following Escitalopram therapy.

Figure 21:
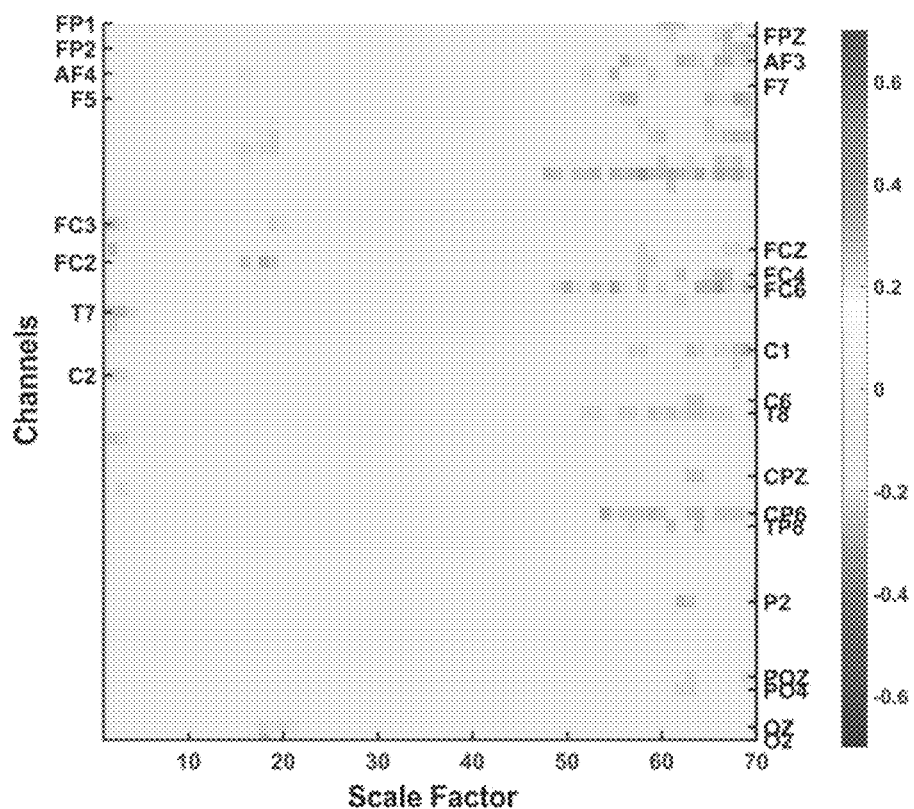
FIG. 21 shows a Link between Baseline Complexity and Change in Mood by Escitalopram.
Figure 21:
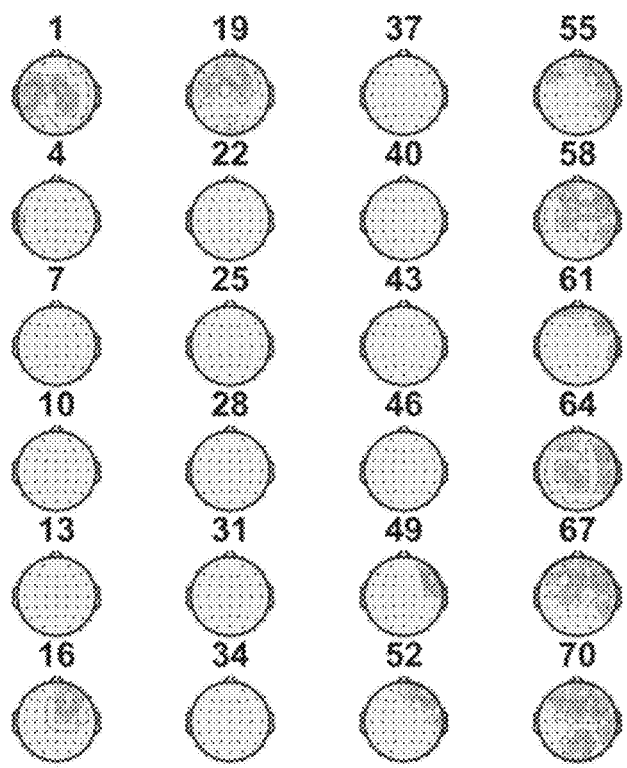

FIG. 21 shows link between Week 2 Complexity and Change in Mood by Escitalopram. Image illustrate all the significant (p<0.05) spearman correlation coefficients (rho) between percent change in MADRS (week 8 to baseline) and week 2 MSE in 95 patients receiving escitalopram therapy. Cluster-based correction for multiple comparison resulted in significant clusters (p<0.05) across multiple brain regions. Bottom: Topographies illustrate spatial distribution of this association.

Figure 22:
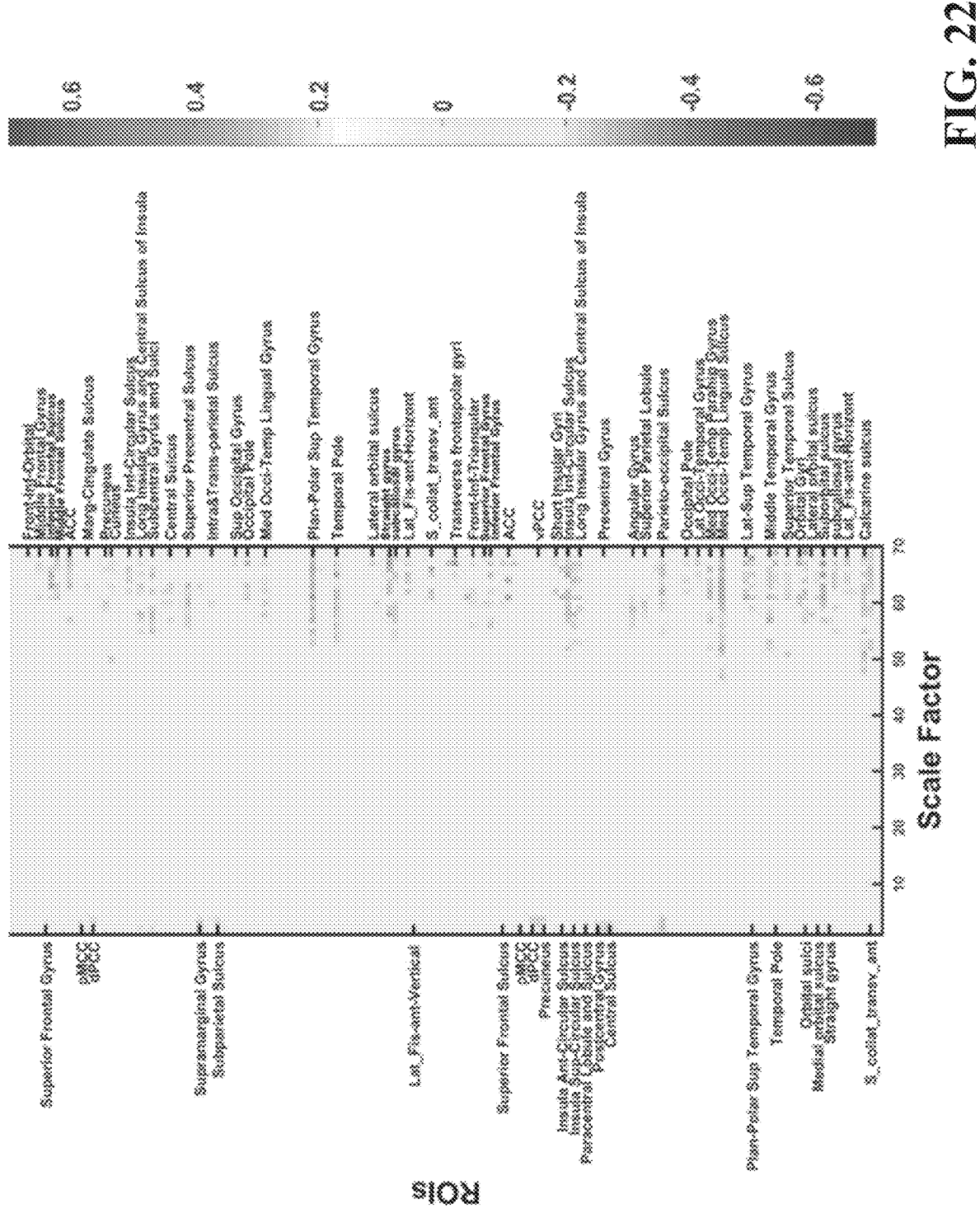
FIG. 22 shows a Link between Week 2 Complexity and Change in Mood by Escitalopram in Source Space.

FIG. 22 shows link between Week 2 Complexity and Change in Mood by Escitalopram in Source Space. Source analysis of data from prior figure reflects all brain region whose complexity at week 2 of treatment is associated with change in depressive symptoms following Escitalopram 8 weeks of therapy.

FIG. 1 shows the Effect of Seizure Therapy on Complexity of Temporal Dynamics. Top. Waveforms depict multi-scale entropy (MSE) pre (black line) and post (red line) electroconvulsive therapy (ECT) and magnetic seizure therapy (MST) in responders (A, C) and non-responders (B, D). The lines represent the average MSE (y-axes) across electrodes (dots) for time-scales 1 to 70 (s-axes). Middle. Images show the original post-hoc test statistics comparing MSE post to pre-treatment across all electrodes (1 to 60) and all time-scales (1 to 70) (blue: decreases; red: increases following treatment) for responders and non-responders to ECT (A, B) and MST (C, D). Bottom. Each topography reflects the significant t-maps following correction for multiple comparison, using cluster-based non-parametric permutation test, depicting only the significant clusters p<0.05 and setting to 0 non-significant pixels. Topographies highlight the spatial characteristics of the reduction of MSE in fine time-scales common to both ECT and MST responders (A, C) and the increase in MSE in coarse time-scales following ECT alone (A). In ECT responders, there was a significant (cluster p=0.003) global decrease in time-scales less than 30 and a significant (cluster p=0.002) global increase in coarser time-scales. By contrast, in MST responders, only a wide spread reduction in time-scales less than 20 was observed (cluster p=0.033). In MST responders, the reduction of MSE in fine time-scales (e.g., scale factor 4) was localized to parieto-occipital (P1, P3, P2, P4, POZ, PO3, PO5, PO7, PO4, PO6, PO8, O1, OZ) and fronto-central regions (F4, FC1, FC2, FCZ, CZ, C1, CZ). No significant changes were observed in either ECT or MST non-responders.

Figure 2B:
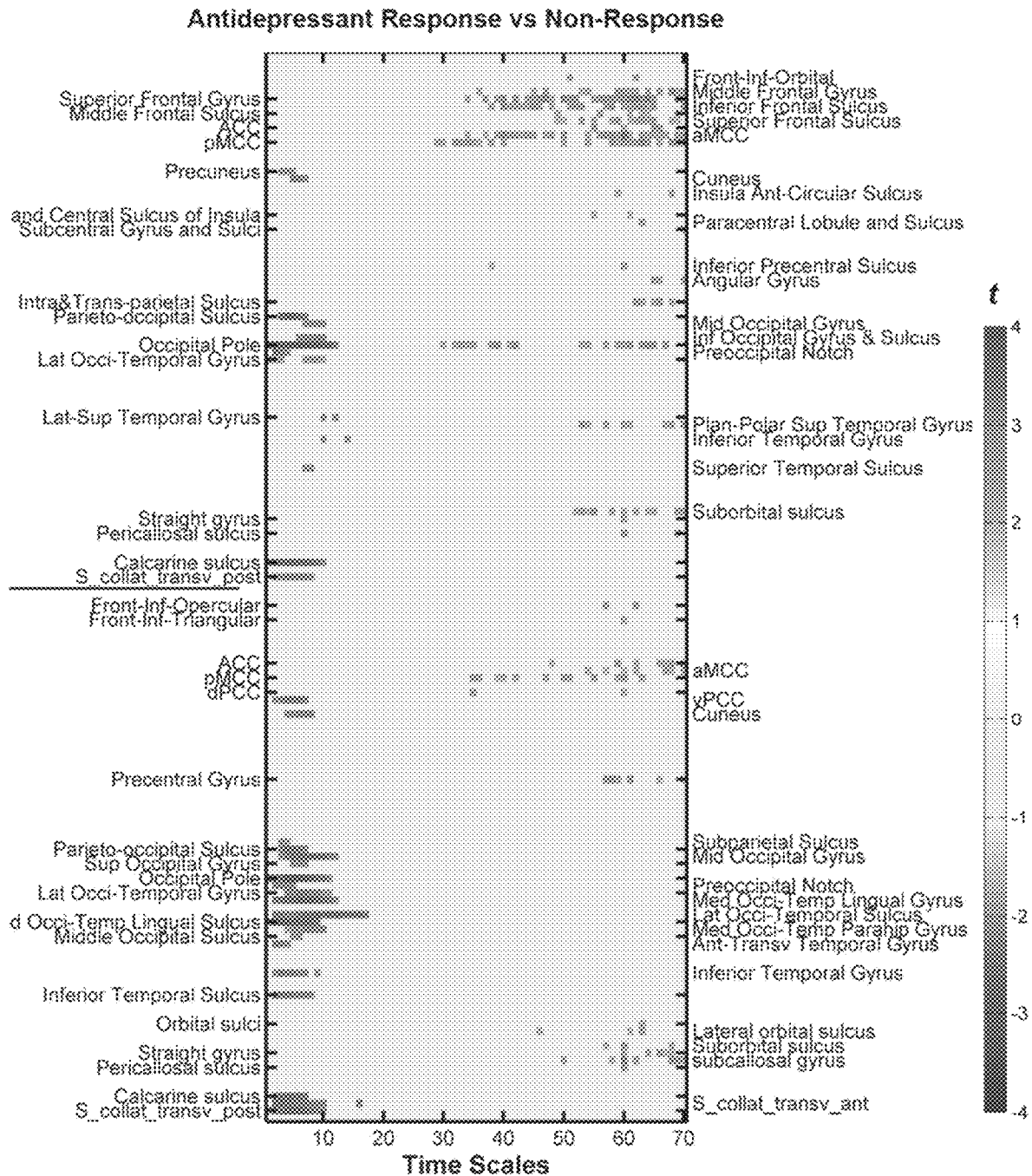

FIG. 2, collectively through FIGS. 2A-2B, depicts the Effect of Seizure Therapy on Complexity in the Source Space. In all images, X-axis represents the time scale (1 to 70) and y-axis represents Regions of Interest (ROIs) of the Destrieux Atlas (1 to 148). The ROIs are grouped into brain regions in the left (L: the upper half of the images) and right (R: the lower half of the images) hemisphere separated by the horizontal black line. FIG. 2A. shows an image of the post-hoc independent sample t-test statistics following cluster-based permutation test correction for multiple comparison, depicting only the significant clusters p<0.05, labeling only the significant corresponding ROIs, and setting to 0 non-significant pixels. Image shows the t-test statistics comparing the changes in MSE (Post-Pre/Pre) between participants who received ECT and MST interventions (red: higher increases in ECT; blue: higher decreases in ECT). This image depict that MSE in fine time scales (e.g., <10) was significantly lower post treatment in ECT compared to MST group, and increases in coarse time scales (e.g., >28) were significantly higher in ECT compared to MST intervention group. FIG. 2B shows an image of the independent sample t-test statistics comparing the change in MSE (Post-Pre/Pre) between participants who were considered responders to seizure therapy (>=50% reduction in HAMD from baseline) and non-responders (red: higher increases in responders; blue: higher decreases in responders). The regions of significance did not survive the cluster-based correction for multiple comparisons at cluster p<0.05, thereby, this image depicts the outcome of bootstrapping statistics only. Responders may have more reduction is MSE post treatment in fine time scales in brain regions such as precuneus, bilateral cuneus, bilateral parieto-occipital sulcus, bilateral occipital pole, bilateral lateral occi-temporal gyrus, calcarine sulcus, and bilateral posterior transverse collateral sulcus. Responders may also have more increases post treatment in coarser time scales (e.g., >40) mainly in the left inferior, middle and superior frontal sulcus, middle and superior frontal gyrus, and orbital part of inferior frontal gyms.

Figure 3:
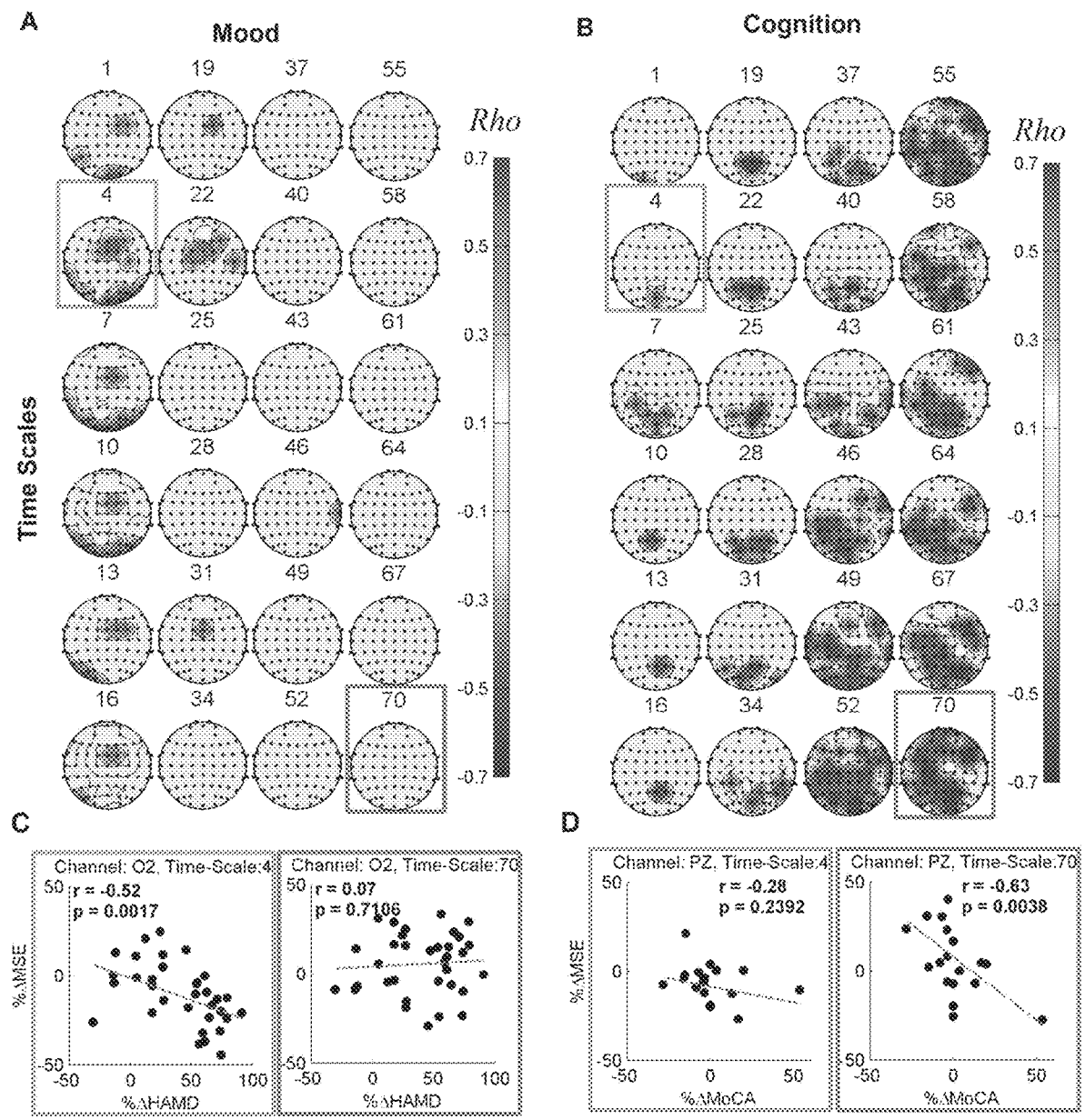
FIG. 3 shows the Association between Modulation of Temporal Complexity and Mood and Cognition.

FIG. 3 shows the Association between Modulation of Temporal Complexity and Mood and Cognition. A. Topographies illustrate all the significant (original p<0.05) spearman correlation coefficients (rho) between percent change in HAMD and MSE in 34 patients receiving seizure therapy. Cluster-based correction for multiple comparison resulted in significant negative clusters (p<0.01) in parieto-occipital (TP7, P7, P5, P8, PO7, PO5, PO6, PO8, O1, O2, Oz) and fronto-central regions (AF4, F1, FZ, F2, F4, FC1, FC2, FC4, FCZ, C1, C4, CZ) in time-scale less than 30 factors. B. Topographies illustrate all the significant (original p<0.05) spearman correlation coefficients (rho) between the percentage change in MoCA and MSE across time-scales in 19 patients receiving seizure therapy. Custer-based correction for multiple comparison revealed a significant negative cluster (p<0.01) in parieto-central region (e.g., PZ, POZ, P1, P2) across time-scales and globally in courser (higher) time-scales. C, D. Scatter plots highlight the time-scale and region-specific association between percent change in MSE (y-axes) and percent change in HAMD (x-axis in C), and percent change in MoCA (x-axis in D). C. Scatter plots show that change in MSE was significantly associated with change in HAMD in the occipital region in fine time-scale (O2, time-scale 4, r=−0.52, p=0.0017) but not course times-scale (O2, time-scale 70, r=0.07, p=0.71). D. Scatter plots show that change in MSE was significantly associated with change in MoCA in the parieto-central region in course tune-scale (PZ, time-scale 70, r−0.63, p=0.0038) but not fine time-scales (PZ, time-scale 4, r=−0.28, p=0.24).

FIG. 4. shows the Region-Specific Change in Temporal Complexity Predicts Change in Mood and Cognition. A, C. Topographies depict area under the curve (AUC) of the receiver operating characteristic (ROC) curve of change in multiscale entropy (MSE) in predicting antidepressant (A), and cognitive change (C) in response to seizure therapy at every electrode and time-scale. The hot colors illustrate higher AUC and better prediction. Change in complexity of low time-scales (e.g. 4-6,8) in right parieto-occipital brain regions (OZ, O2, PO8) offered good (AUC≥0.8) prediction performance of antidepressant response and a fair (0.7<AUC<0.8) prediction performance was observed across low time-scales (e.g., 1-22) in bilateral fronto-central (e.g., FC1, FC2, FCZ, F1) and bilateral parieto-occipital (e.g., O1, PO3, PO5, PO7, PO4, PO6, P7, P8) brain regions (A). Change in complexity of time-scales 14 and higher in parieto-central (e.g., PZ and then globally in coarser time-scales provided excellent (e.g., AUC≥0.9) prediction performance for change in cognition. B, D. Figures depict the ROC curve across all possible threshold values of the predictor for an electrode and time-scale with best prediction performance for antidepressant response (OZ, scale 5) (B) and change in cognition (e.g., AUC (P2 electrode, time-scale 23)=0.98 p<0.0004 (D) X-axes represent false positive rates (I-specificity), y-axes the true positive values (sensitivity). The red circle shows the optimum operating point of the ROC curve. B. At optimum point, this electrode and scale has 82% sensitivity and 77% specificity (good classification). D. At optimum point, this electrode and scale has 89% sensitivity and 100% specificity (excellent classification).

Figure 5D:
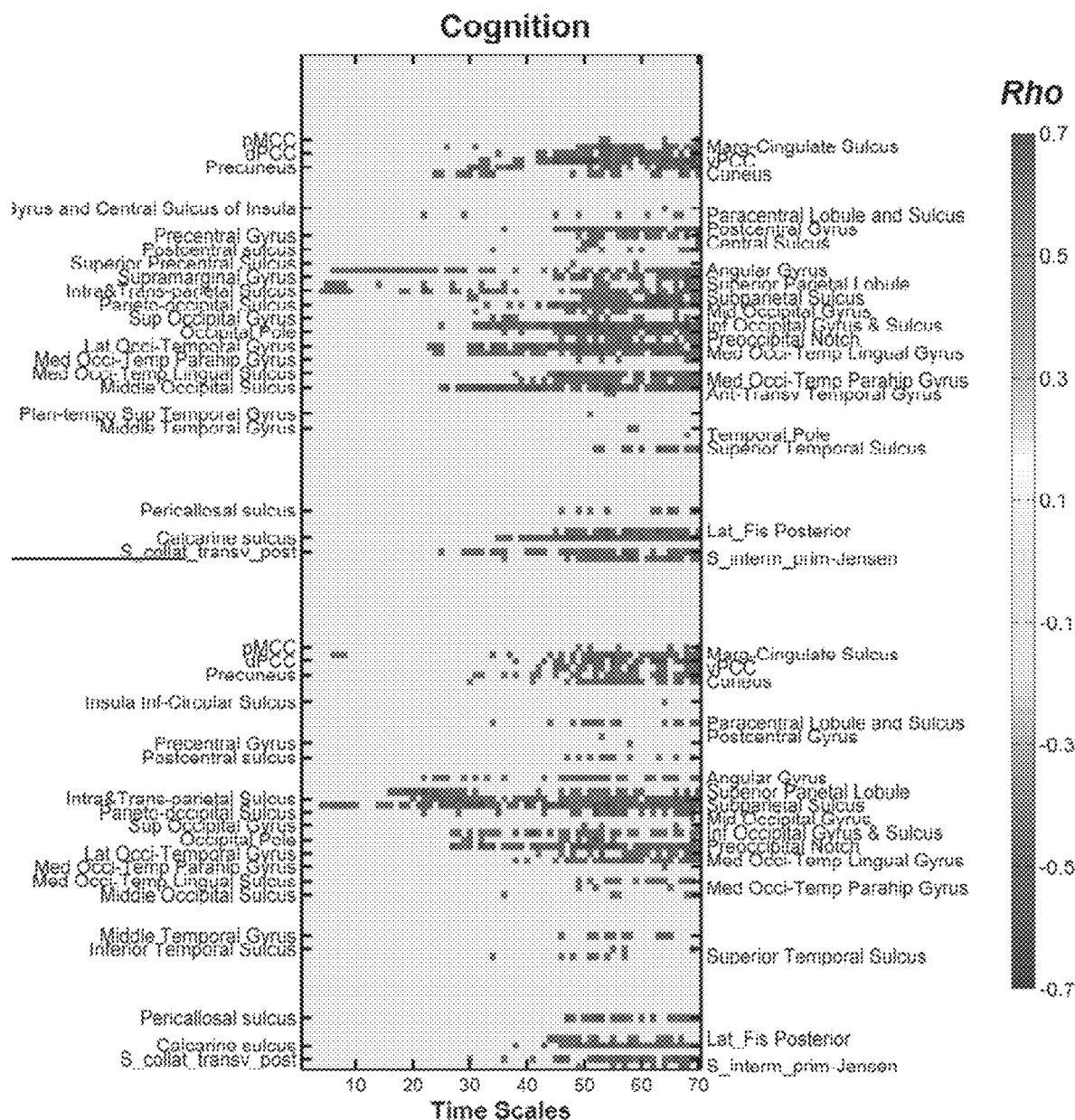

FIG. 5, collectively through FIGS. 5A-5D, shows a Seizure induced Modulation of Complexity and Its Association with Mood and Cognition in the Source Space. In all images, X-axis represents the time scales (1 to 70) and y-axis represents Regions of Interest (ROIs) of the Destrieux Atlas (1 to 148). The ROIs are grouped into left (L: the upper half of the images) and right (R: the lower half of the images) hemisphere brain regions separated by the horizontal red line in each figure. Images show the post-hoc test statistics following cluster-based permutation test correction for multiple comparison, depicting on the significant cluster p0.05, labeling only the significant corresponding ROIs and setting to 0 non-significant pixels. Top: Images show the t-test statistics comparing MSE post to pre-treatment (blue: decreases; red: increased following treatment). In the plot provided at FIG. 5A with regard to "MST Responders", a wide spread reduction in time-scales less than 20 was observed (cluster p<0.05). By contrast, in the plot provided at FIG. 5B with regard to "ECT responders", there was significant (cluster p 0.01) global decrease in time-scales less than 30 and significant (cluster p<0.01) global increase in coarser time-scales. In MST responders, the reduction of MSE in fine time-scales was found in several tempro-parieto-occipital (e.g., cuneous, precuneus, posterior-dorsal part of the cingulate gyrus (dPCC), parieto-occipital sulcus, occipital pole, etc.) and fronto-central brain regions (e.g., opercular part of the inferior frontal gyrus, central sulcus, pre and post central gyrus, etc.). No significant changes were observed in either ECT or MST non-responders. Bottom: The image in FIG. 5C illustrates the significance (p<0.05) spearman correlation coefficients (rho) between percent change in HAMD and MSE in 34 patients receiving seizure therapy. There was significant negative clusters (p<0.01) in time-scale less than 20 factors in tempro-parieto-occipital regions including the bilateral dPCC, bilateral vPCC, bilateral cuneus, precuneus, parieto-occipital sulcus, occipital pole, temporal sulci, bilateral inferior temporal sulcus, bilateral lateral occi-temporal sulcus, bilateral calcarine sulcus, bilateral anterior and posterior transverse collateral sulcus. The image in FIG. 5D illustrates spearman correlation coefficients (rho) between percent change to MoCA and MSE across time-scales in 19 patients receiving seizure therapy. There was significant clusters (p<0.005) in several central, parieto-centra, parieto-occipital, occi-temporal, and temporal brain regions (as labeled on the image) across primarily coarser (>30) time-scales.

Figure 6B:
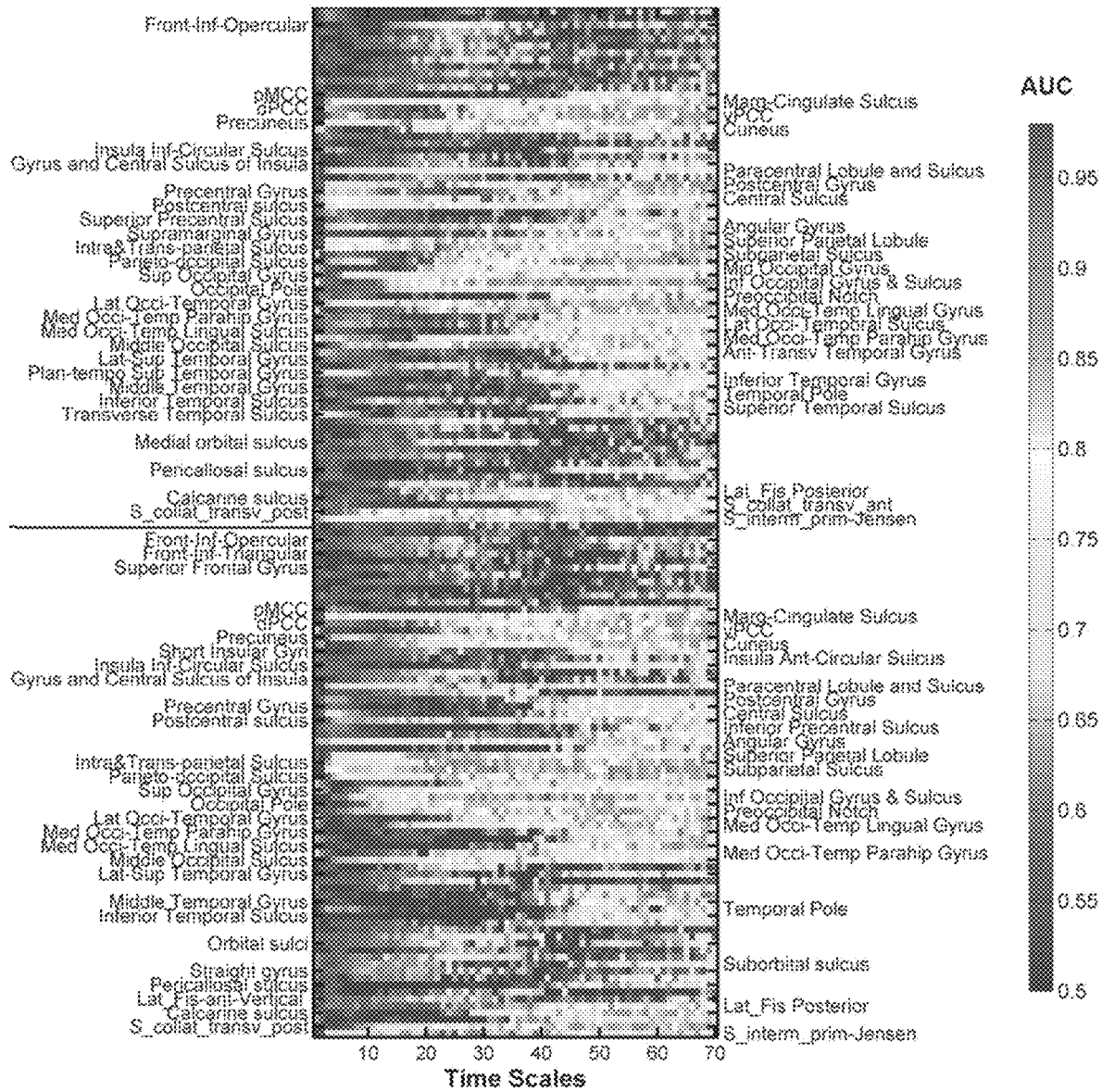
Figure 6C:
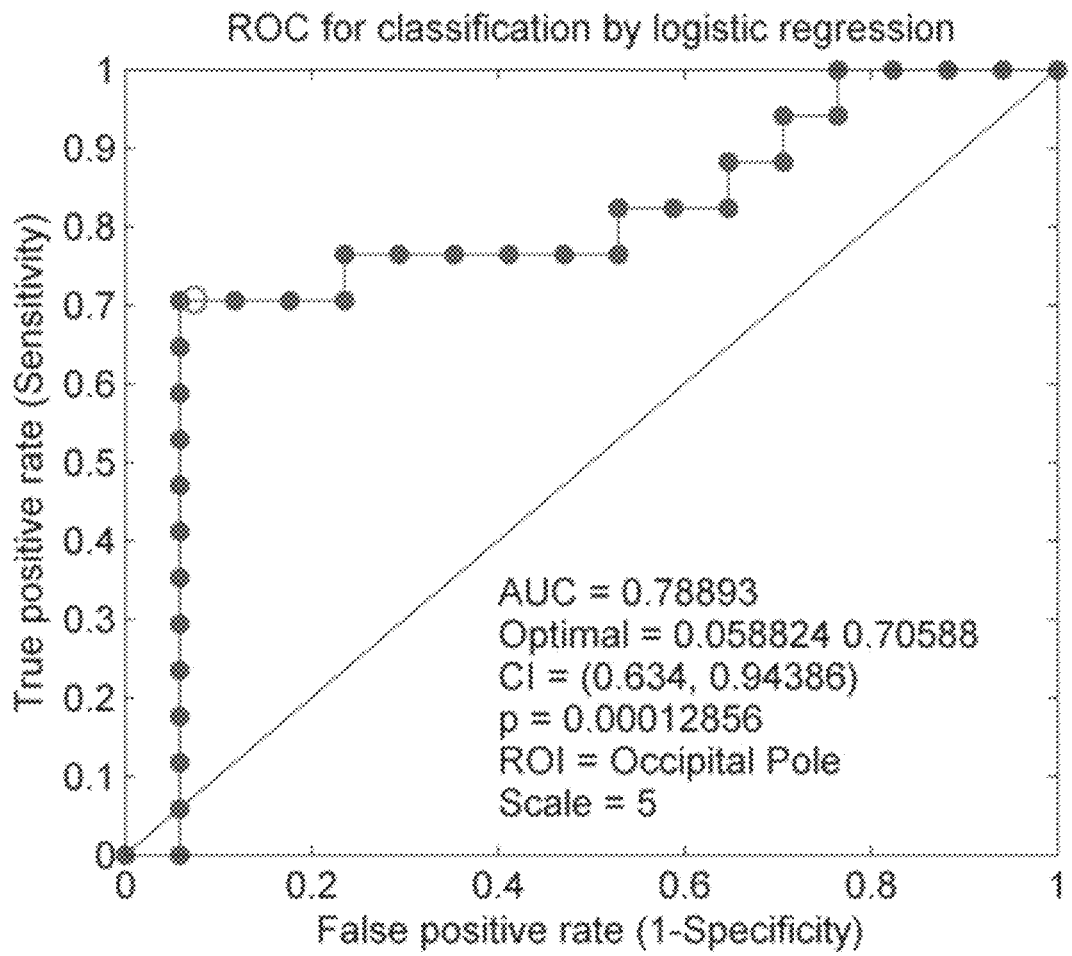
Figure 6D:
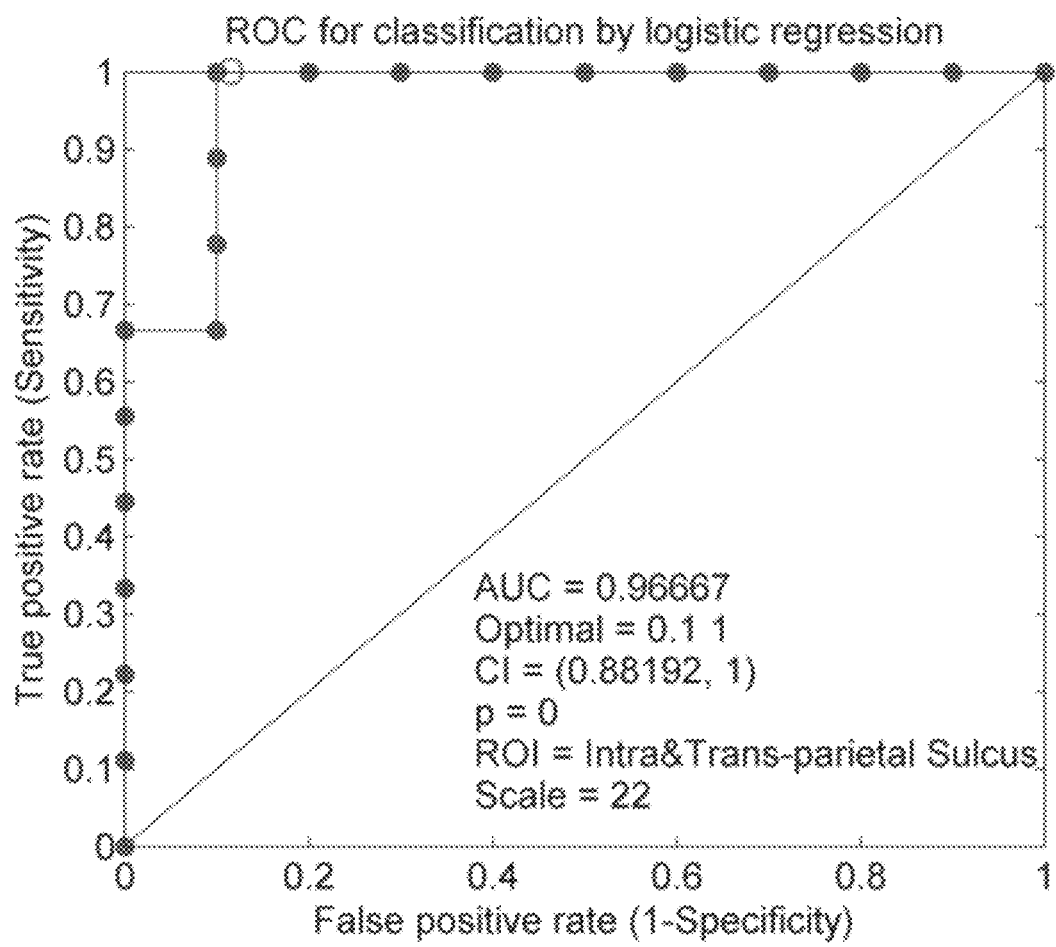

FIG. 6, collectively through FIGS. 6A-6D, shows the Prediction of Change in Mood and Cognition in the Source Space. FIGS. 6A and 6B depict area under the curve (AUC) of the receiver operating characteristic (ROC) curve of change in multiscale entropy (MSE) in predicting antidepressant (A), and cognitive change (C) in response to seizure therapy at every region of interest (ROI) of the Destrieux Atlas (1 to 148) and each time-scale (1 to 70). Hot colors illustrate higher AUC and better prediction. Change in complexity of low time-scales (1 to 20) in parieto-occipital regions (e.g., parieto-occipital sulcus, occipital pole, calcarine sulcus) offered moderate to good (e.g., AUC of 0.75 to 0.80) prediction performance for change in antidepressant response (A). Change in complexity of higher time-scales in parietal brain regions and then spatially globally across time-scales provided excellent (e.g., AUC>0.9) prediction performance for change in cognition. B, D. Figures depict the ROC curve across all possible threshold values of the predicator for an ROI and time-scale for antidepressant response (AUC (right occipital pole, time scale 5)=0.79, p<0.0001) (B) and change in cognition (e.g., AUC (intra and trans-parietal sulcus, time-scale 22)–0.97, p<0.0001). (D). X-axes represent false positive rates (1-specificy), y-axes the true positive values (sensitivity). The red circle shows the optimum operating point of the ROC curve. B. At optimum point, this brain region and scale has 70% sensitivity and 94% specificity. D. At optimum point, this ROI and scale has 100% sensitivity and 90% specificity.

Figure 7:
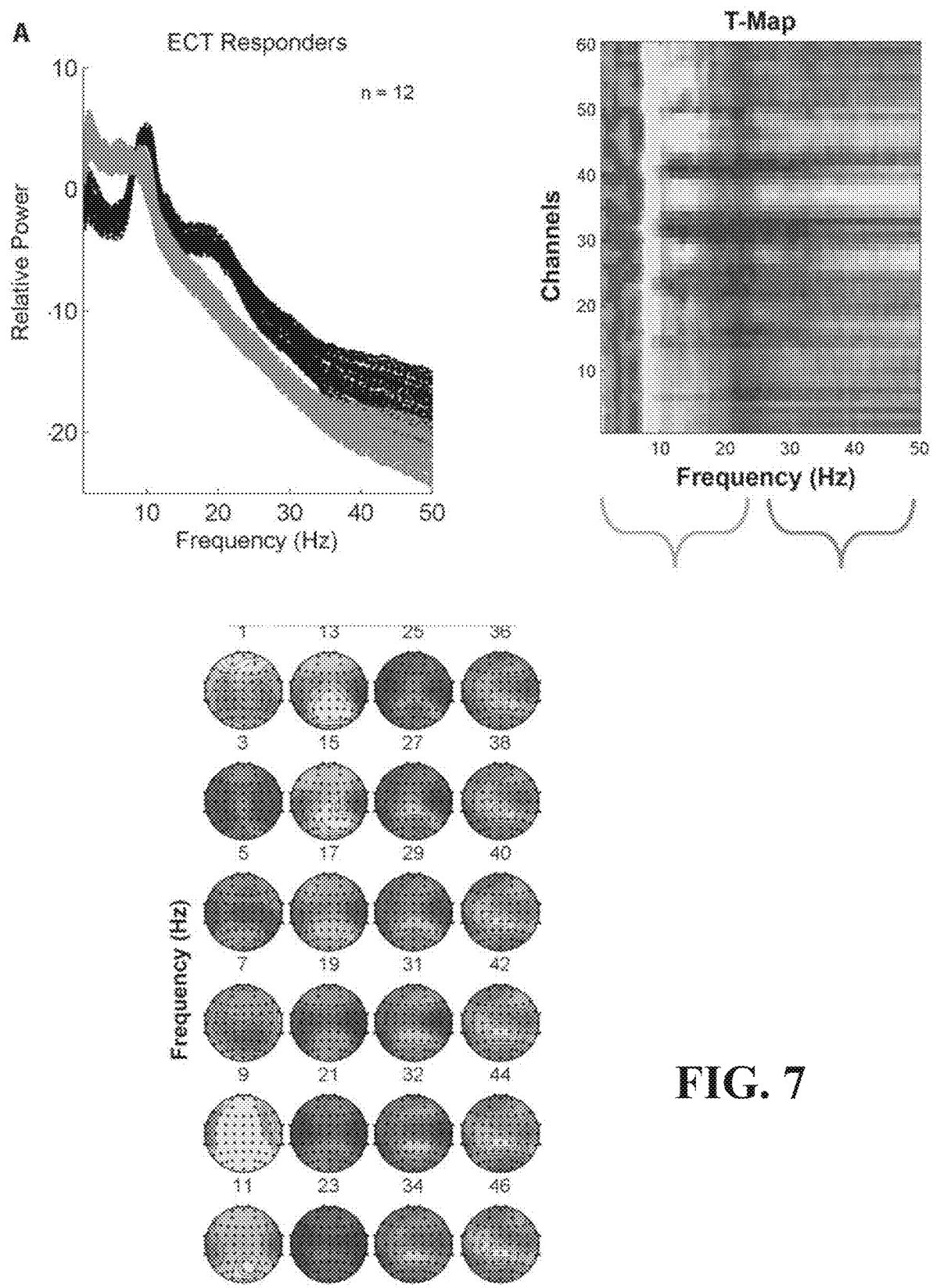
FIG. 7 (also referred to as FIG. S1) shows the Effect of Seizure Therapy on Cortical Oscillations.
Figure 7:
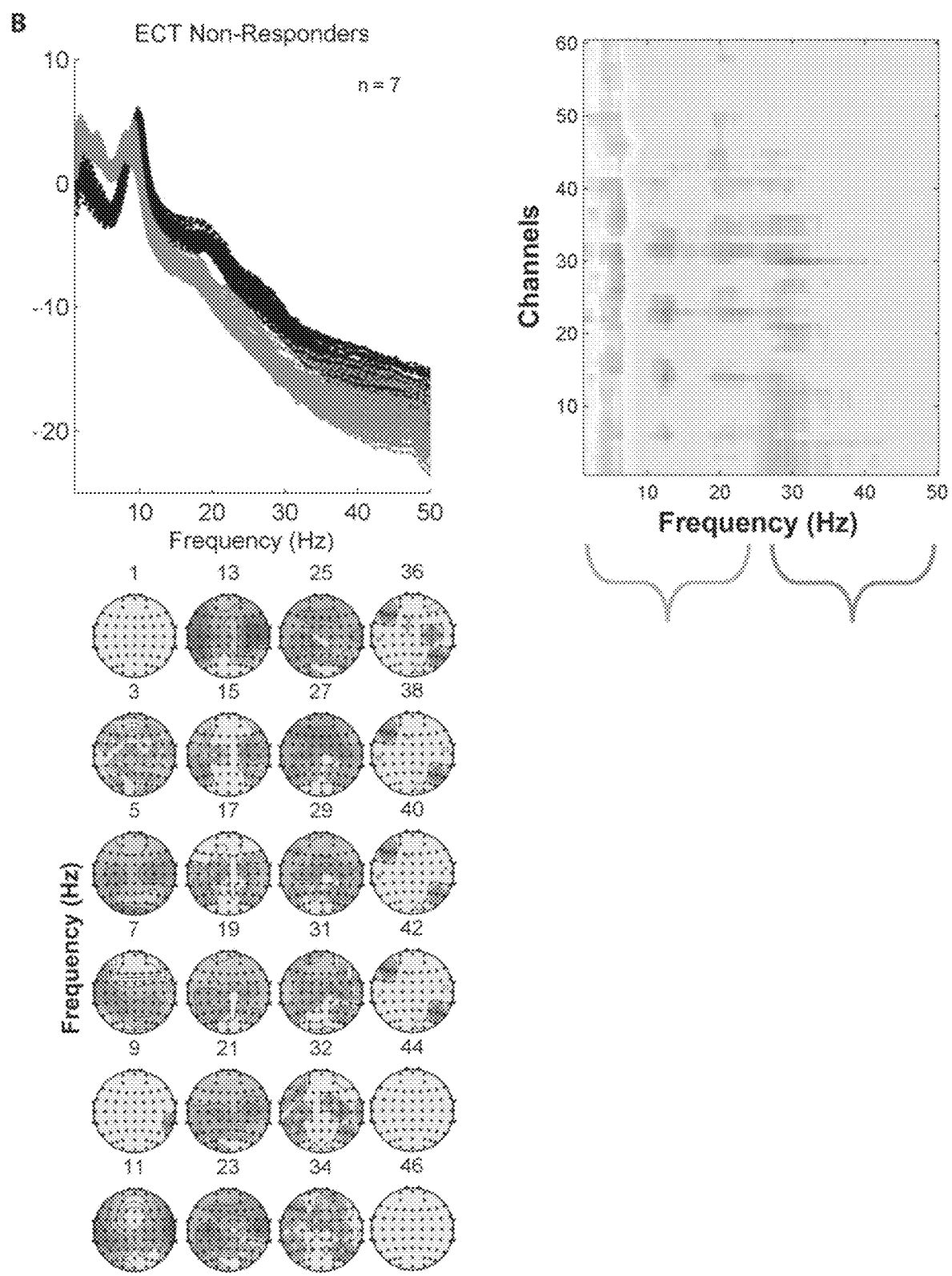
Figure 7:
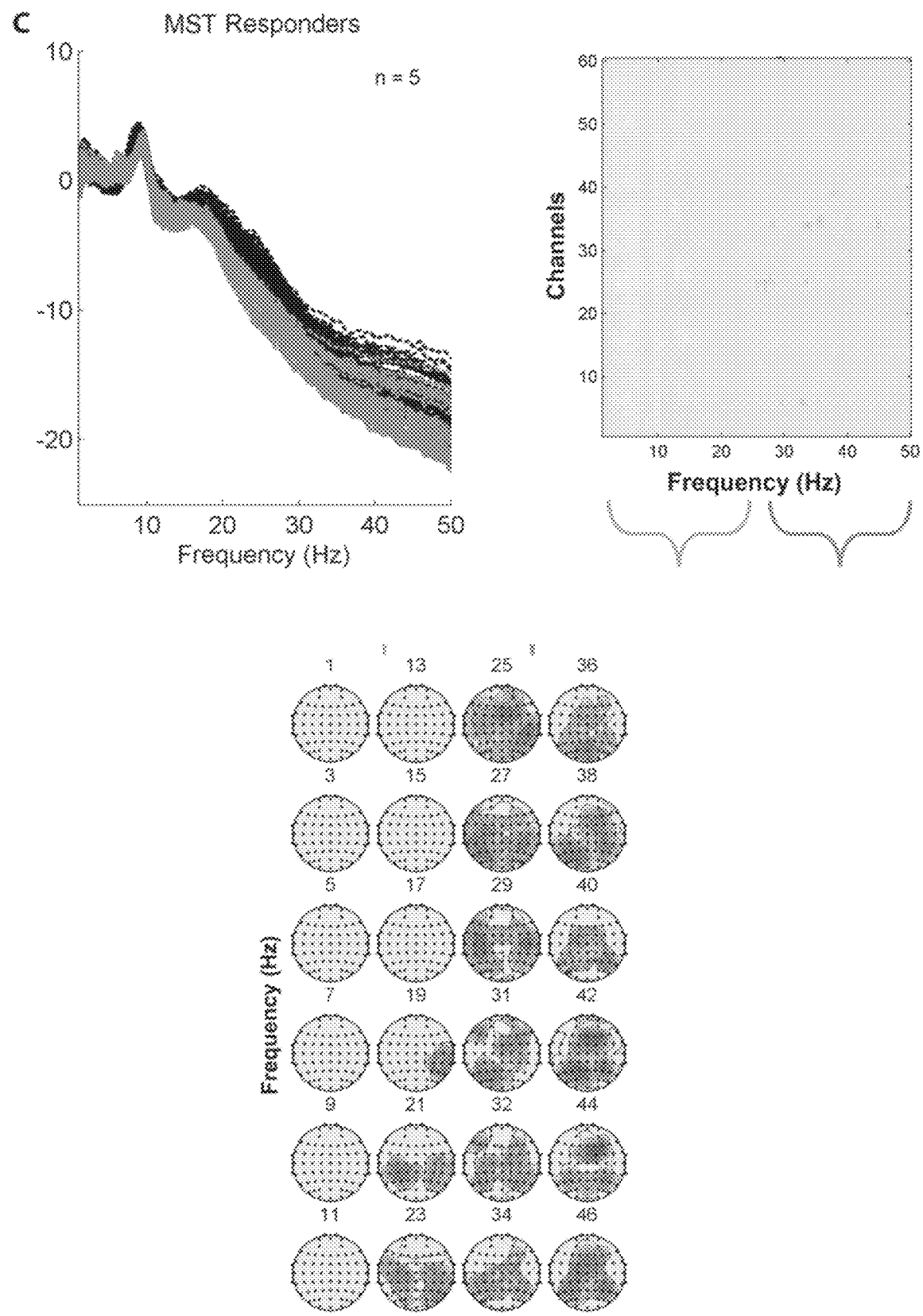
Figure 7:
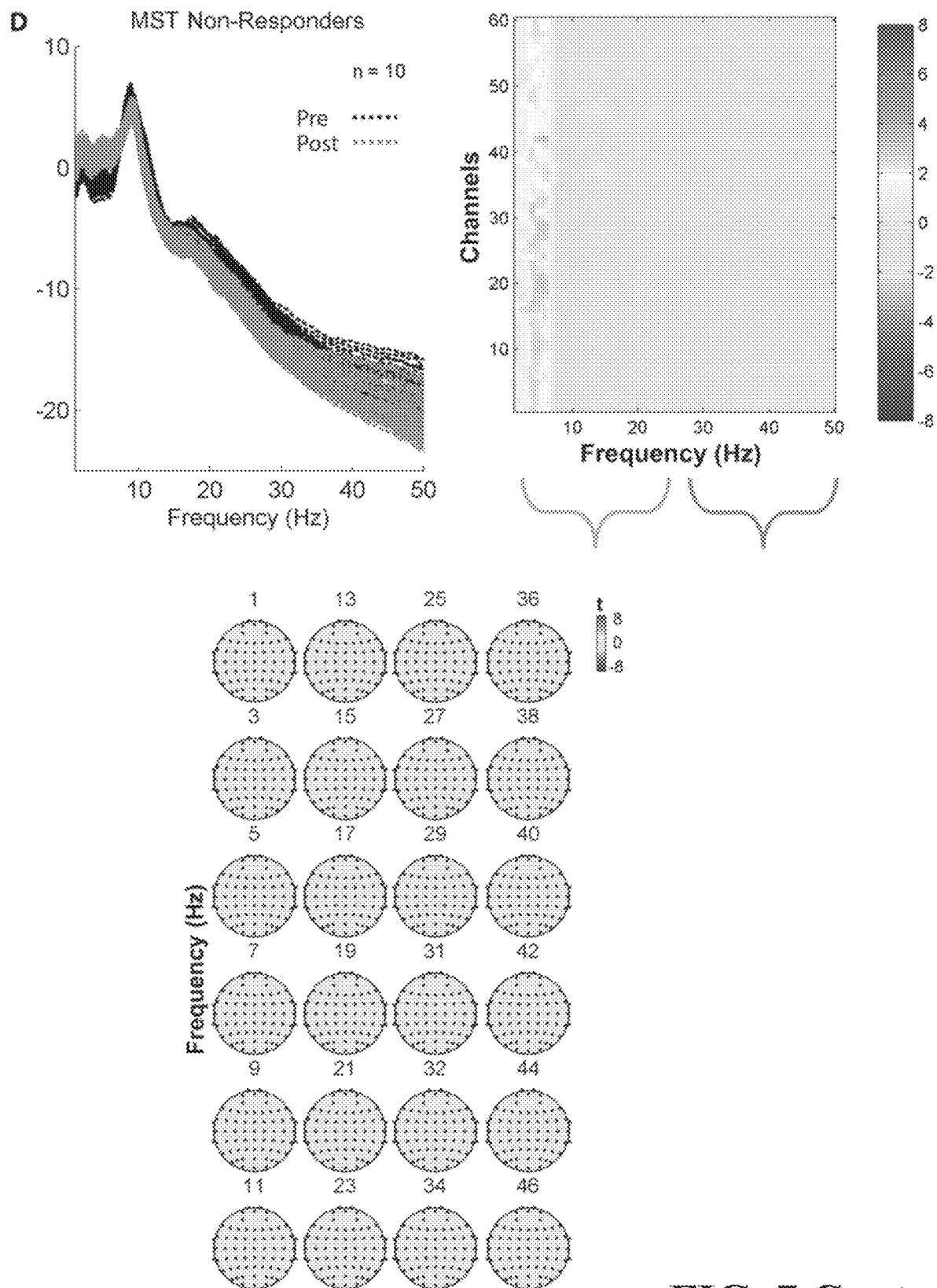

FIG. 7. Effect of Seizure Therapy on Cortical Oscillations. Top. Waveforms depict the relative power spectrum of resting-state eyes-closed EEG pre (black waveforms) and post (red waveforms) electroconvulsive therapy (ECT) and magnetic seizure therapy (MST) in responders (A, C) and non-responders (B, D). The x-axes are frequency in Hz and the y-axes the relative power in dB. Middle. Images show the original post-hoc test statistics maps comparing the relative power across frequency bands (x-axes) and channels (y-axes) post compared to pre-treatment (blue: decreases; red: increases following treatment) for responders and non-responders. Bottom. Each topography reflects the significant t-map depicting only the significant clusters p<0.05, setting to 0 non-significant pixels. Topographies highlight the spatial characteristics of a global increase in relative power of frequencies<8 Hz (cluster p=0.018) and a significant (cluster p<0.001) global decrease in frequencies>9 Hz in ECT responders, but a wide spread reduction in relative power of frequencies>18 Hz (cluster p<0.001) in MST Responders. Significant (cluster p=0.042) but less pronounced wide spread increase of 2 to 7 Hz and decrease (cluster p=0.017) of 10 to 35 Hz were observed in ECT non-responders. No significant changes were observed in MST non-responders.

Figure 8:
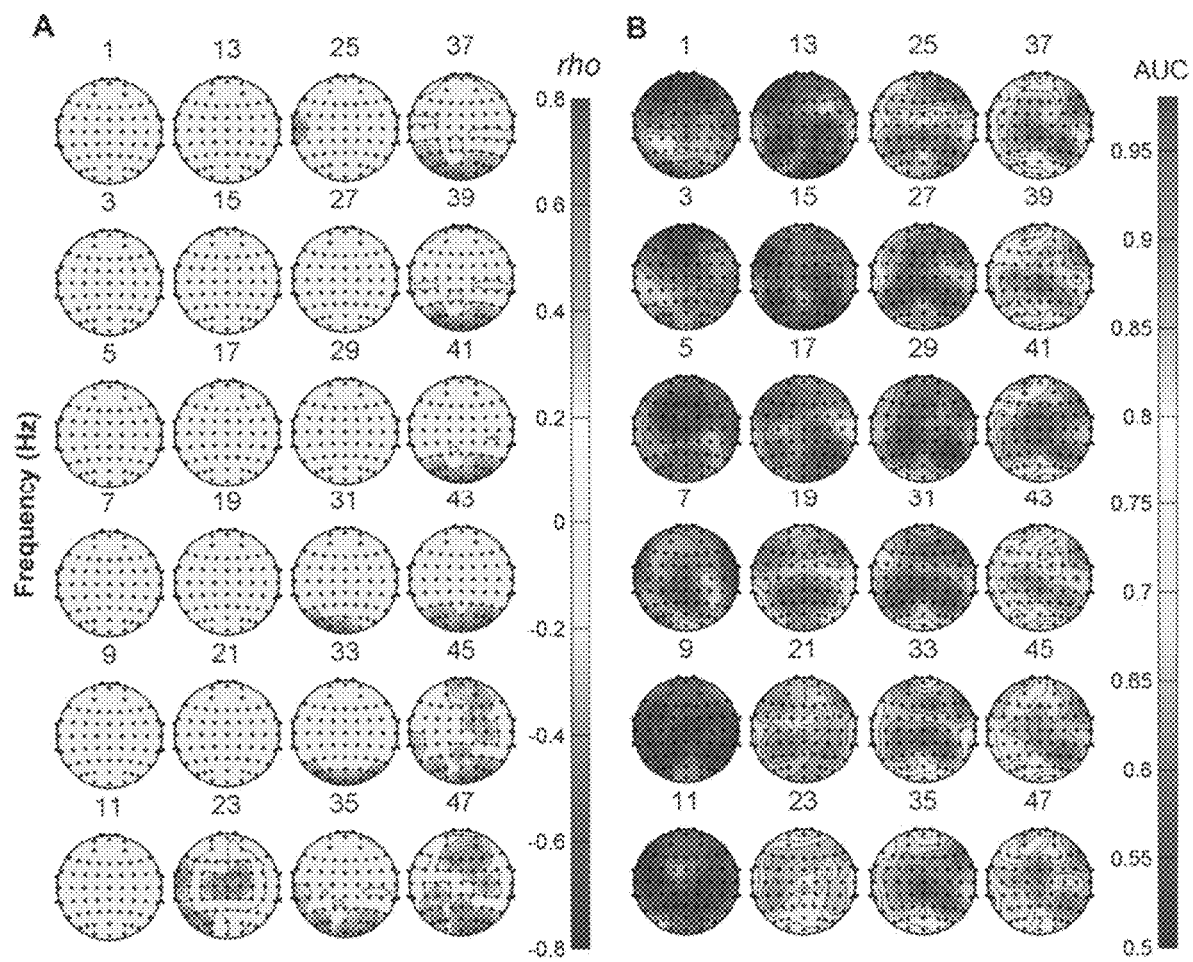
FIG. 8 (also referred to as FIG. S2) shows The Association between Cortical Oscillations and Mood.

FIG. 8 (also referred to as FIG. S2) shows The Association between Cortical Oscillations and Mood. A. Topographies illustrate all the significant (original p<0.05) spearman correlation coefficients (rho) between percent change in HAMD and change in power. All electrodes and frequencies that did not survive the correction for multiple comparisons were set to 0 (green colors). Cluster-based permutation test correction for multiple comparison revealed significant negative clusters (p<0.01) in high frequencies (e.g., >30 Hz) in parieto-occipital regions (e.g., P7, P5, PO7, PO5, PO4, PO6, PO8, OI, OZ) and fronto-central regions (e.g., AF4, F1, FZ, F2, F4, FC2) B. Topographies depict area under the curve (AUC) of the receiver operating characteristic (ROC) curve of change in relative power of cortical oscillations in predicting change in depressive symptoms in response to seizure therapy at every electrode and frequency. The hot colors illustrate higher AUC and better prediction. Change in cortical oscillations did not provide good accuracy (i.e., AUC>0.8) in predicting change in depressive symptoms.

Figure 9:
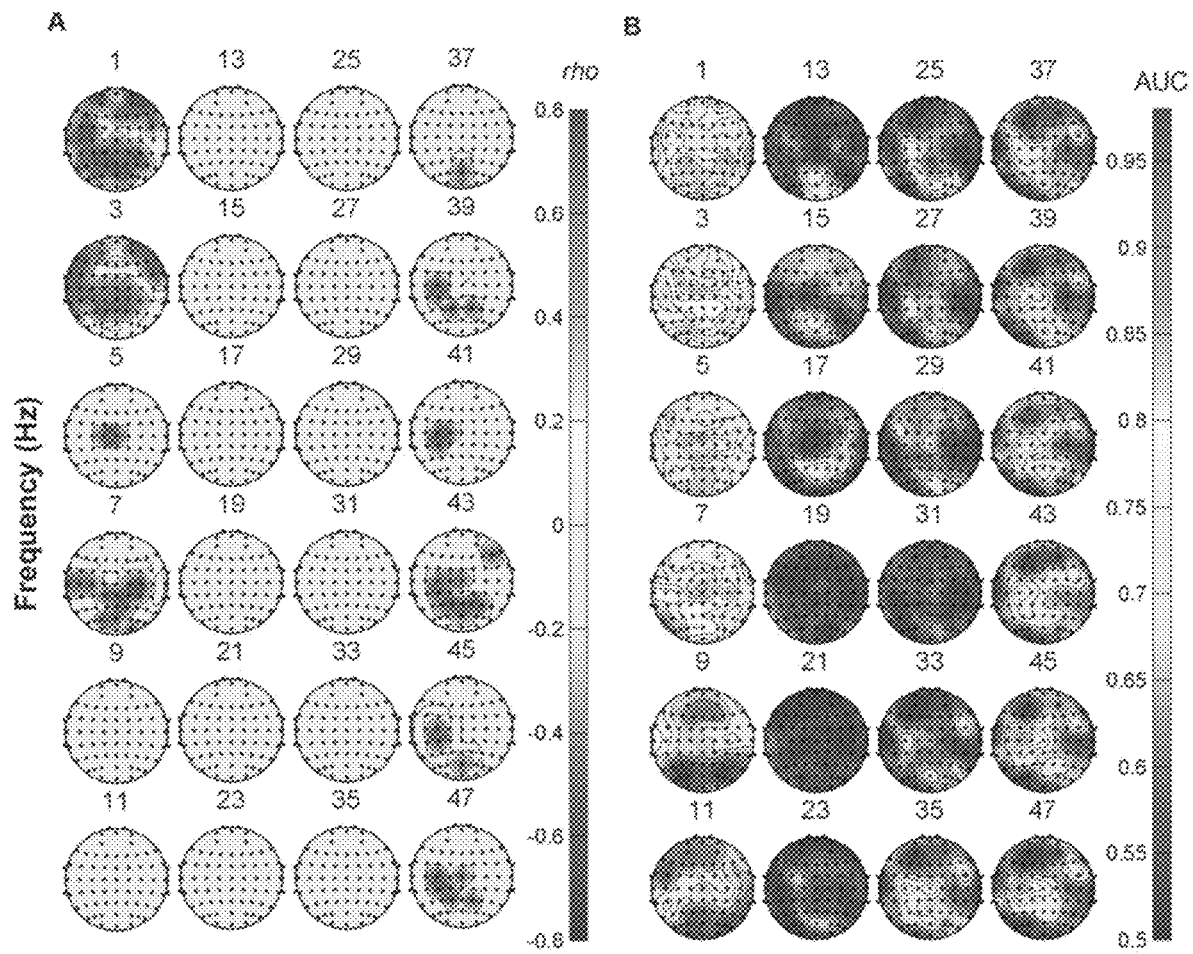
FIG. 9 (also referred to as FIG. S3) depicts The Association between Cortical Oscillations and Cognition.

FIG. 9 (also referred to as FIG. S3) shows The Association between Cortical Oscillations and Cognition. A. Topographies illustrate all the significant (original p<0.05) spearman correlation coefficients (rho) between percent change in MoCA and change in power. All electrodes and frequencies that did not survive the correction for multiple comparisons were set to 0 (green colors). Cluster-based non-parametric correction for multiple comparison revealed a significant global negative cluster (p<0.01) in slow oscillations (e.g., 1 and 3 Hz) and in parieto-central regions (e.g., C1, C3, CZ, CP3, P1, PZ, P2, P4, POZ) in high frequencies (e.g., >40 Hz). B. Topographies depict area under the curve (AUC) of the receiver operating characteristic (ROC) curve of change in relative power of cortical oscillations in predicting cognitive change in response to seizure therapy at every electrode and frequency. The hot colors illustrate higher AUC and better prediction. Change in power of low frequency oscillations (e.g., 1-3 Hz) a provided good prediction value (0.8<AUC<0.9) such as in parieto-central retions (e.g., PZ, P2). Power of high frequency oscillations in the left motor cortex (i.e., C3 electrode, 47 Hz) provided the best prediction value (AUC=0.9).

Figure 10:
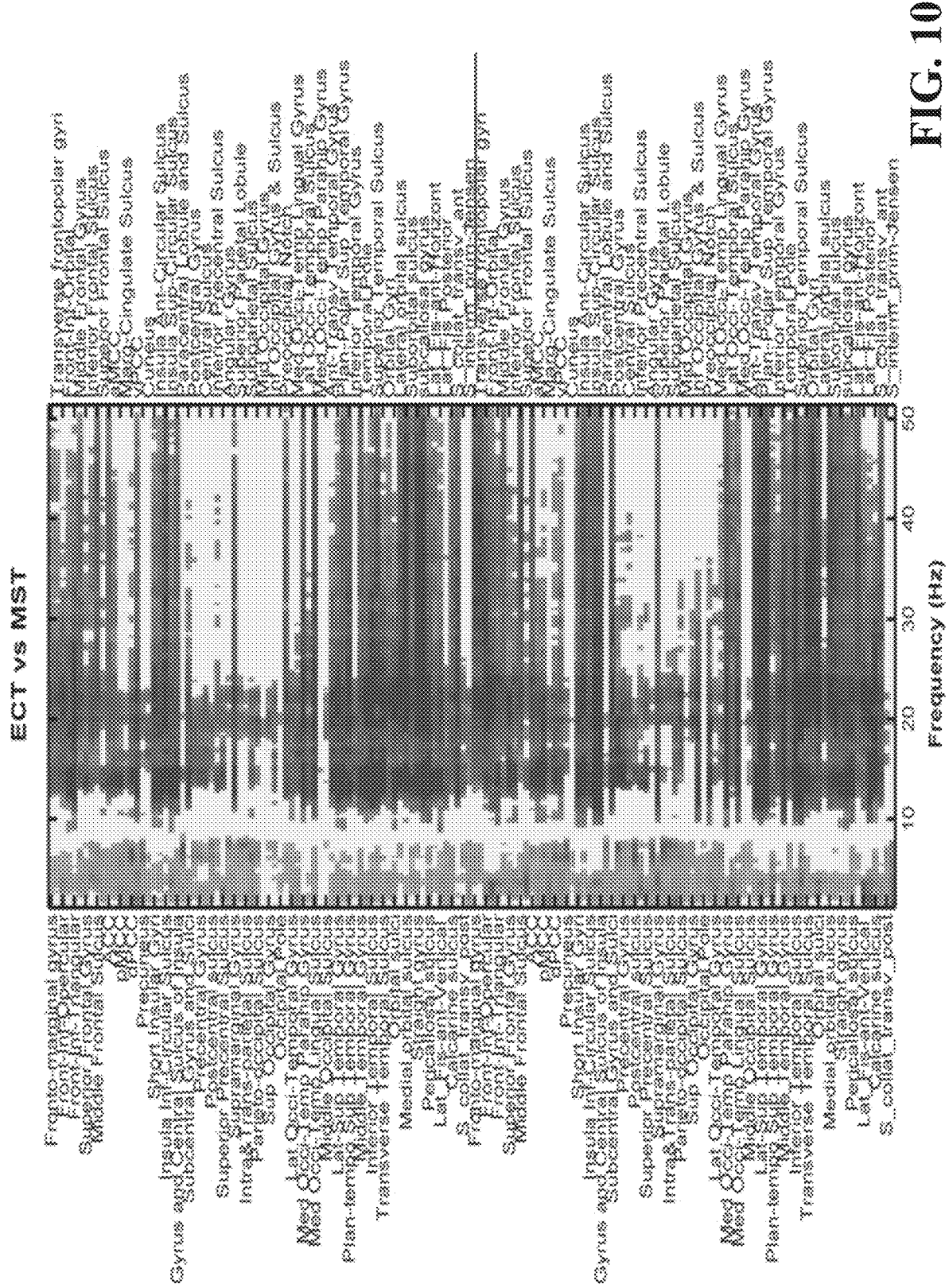
FIG. 10 (also referred to as FIG. S4) shows the Effect of Seizure Therapy on Cortical Oscillations in Source Space.
Figure 10:
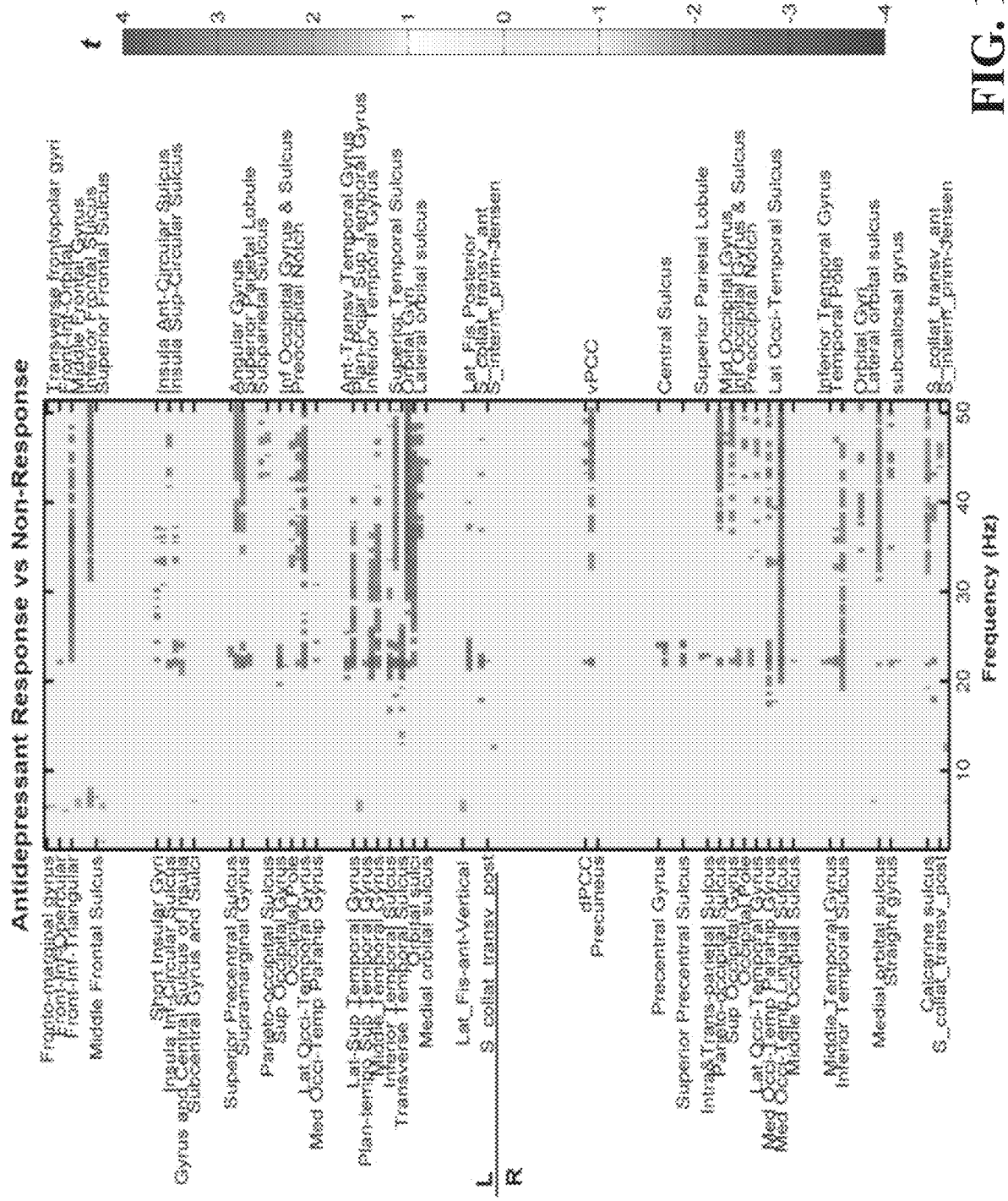

FIG. 10 (also referred to as FIG. S4) shows the Effect of Seizure Therapy on Cortical Oscillations in Source Space. In all images, x-axis represents the frequency (1 to 50) in Hertz and y-axis represents Regions of interest (ROIs) of the Destrieux Atlas (1 to 148). The ROIs are grouped into brain regions in the left (L: the upper half [of] the images) and right (R: the lower half of the images) hemisphere separated by the horizontal black line. Images show the post-hoc independent sample t-test statistics following cluster-based permutation test correction for multiple comparison, depicting only the significant clusters p<0.05, labeling only the significant corresponding ROIs, and setting to 0 non-significant pixels. A. Image shows the t-test statistics comparing the change in power between participants who received ECT and MST interventions (red: more increase in ECT; blue: more reductions in ECT). This image depicts a significantly greater increase in slow oscillations (<10 Hz) and greater decrease in power of frequencies 20-50 Hz in the ECT group. This effect is spatially global. B. Image shows the independent sample t-test statistics comparing the change in power between participants who were considered responders to seizure therapy (>=50% reduction in HAMD from baseline) and non-responders. This image depicts a greater reduction in power of frequencies 20-50 Hz in responders. This finding is spatially global at –22 Hz, but more local in higher frequencies (30-50 Hz). Specifically in 30-50 Hz, the reduction in power is observed in regions such as the inferior frontal sulcus, left orbital part of the frontal inferior gyrus, bilateral preocciptial [preoccipital] notch, orbital gyri, lateral orbital sulcus, lateral occi-temporal sulcus, medial orbital sulcus, bilateral parieto-occiptial[parieto-occipital] sulcus, or bilateral superior parietal lobule.

Figure 11:
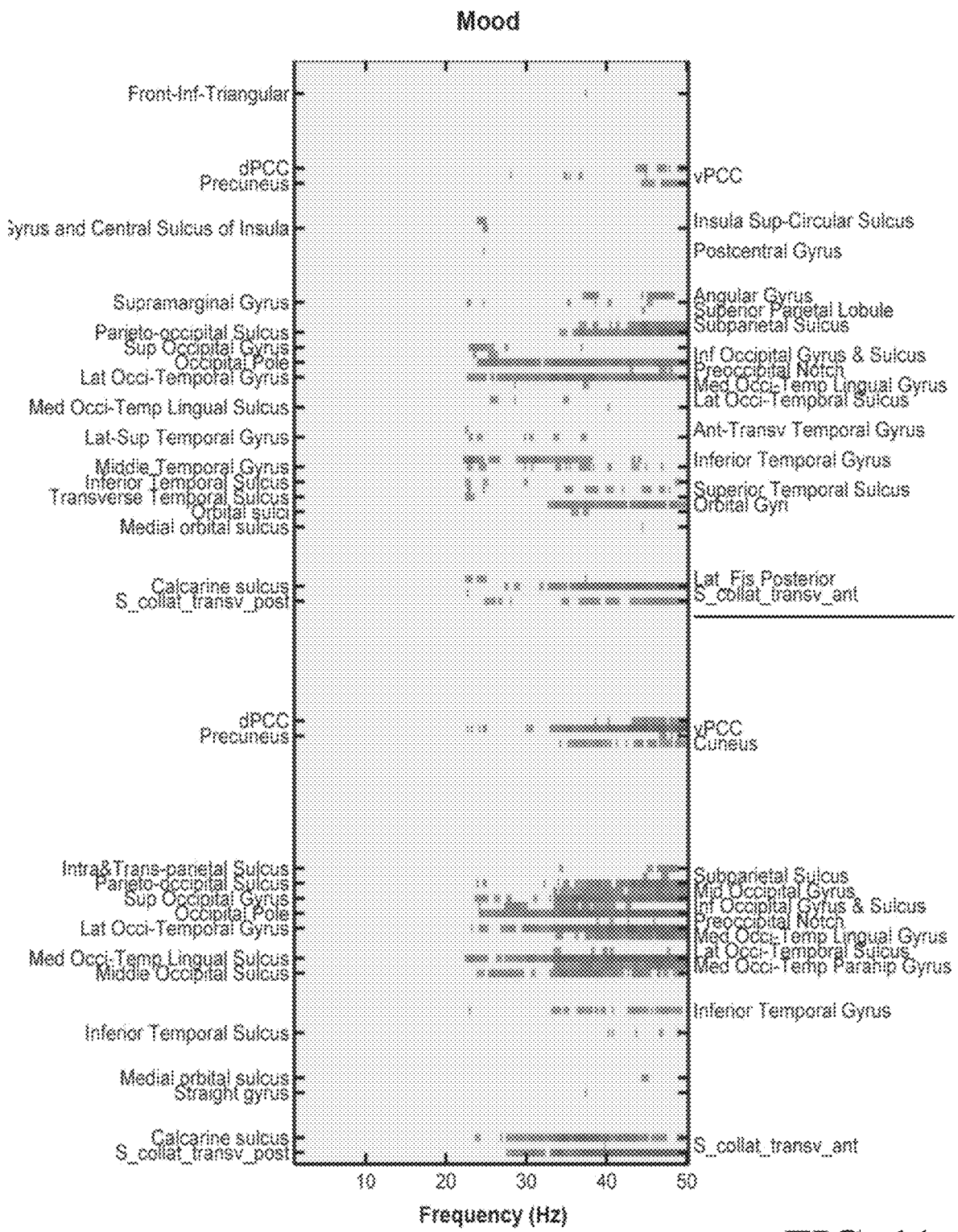
FIG. 11 (also referred to as FIG. S5) shows The Association between Cortical Oscillations and Mood and Cognition in Source Space.
Figure 11:
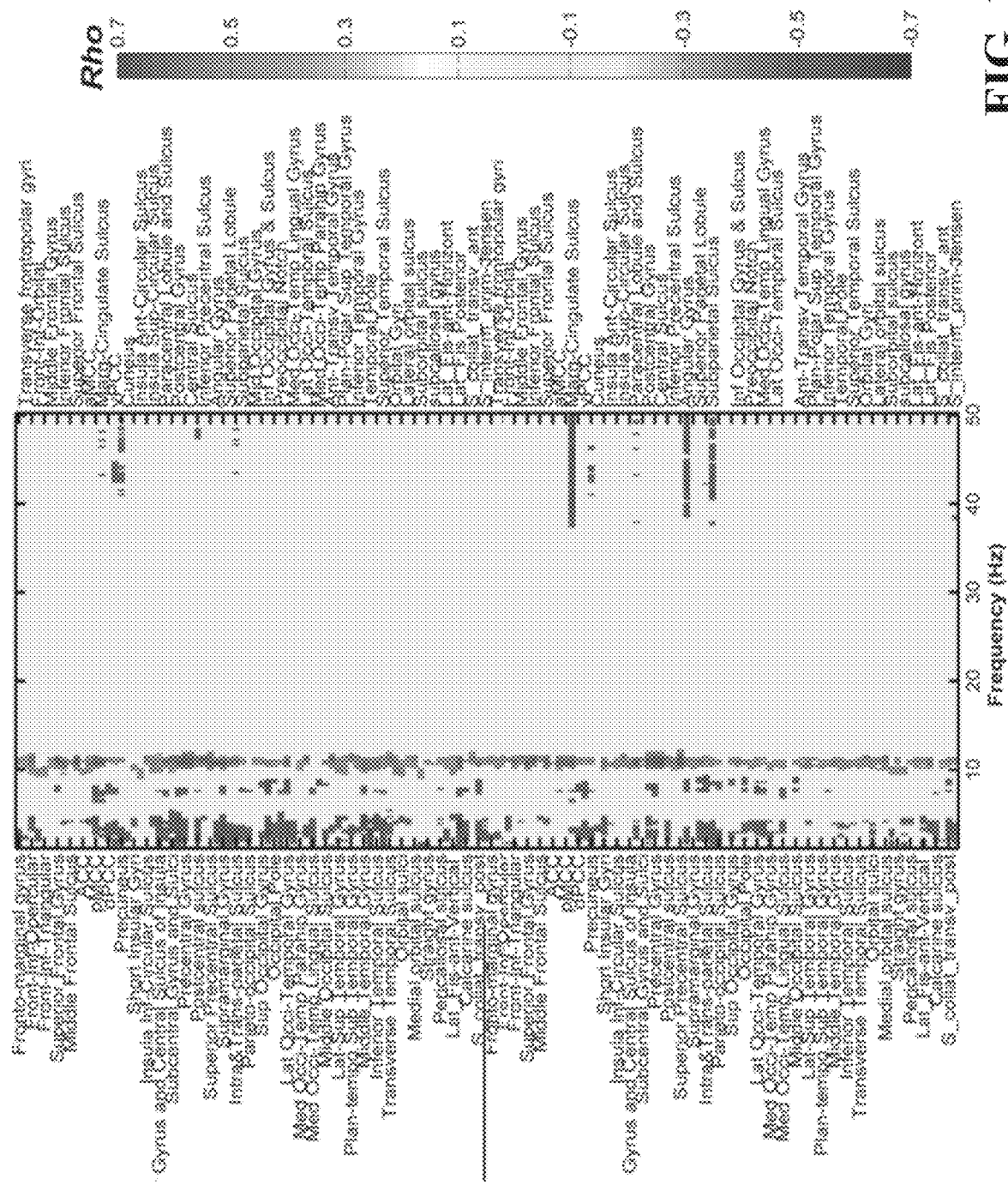

FIG. 11 (also referred to as FIG. S5). The Association between Cortical Oscillations and Mood and Cognition in Source Space. A. Image illustrate the significant (p<0.05) spearman correlation coefficients (rho) between percent change in HAMD and power in 34 patients receiving seizure therapy. All sources and frequencies that did not survive the correction for multiple comparisons were set to 0 (green colors). Only sources that are significant have been listed. There were significant negative clusters in tempro-parieto-occipital regions (e.g., orbital sulci and gyri, bilateral dPCC, vPCC, precuneus, parieto-occipital sulcus, occipital pole, inferior temporal gyrus, lateral occi-temporal sulcus, etc.) in frequencies higher than 30 Hz. B. Image illustrates spearman correlation coefficients (rho) between percent change in MoCA and power across time-scales in 19 patients receiving seizure therapy. There was a global negative cluster in slow oscillations and a global positive association at 10 Hz frequency.

Figure 12:
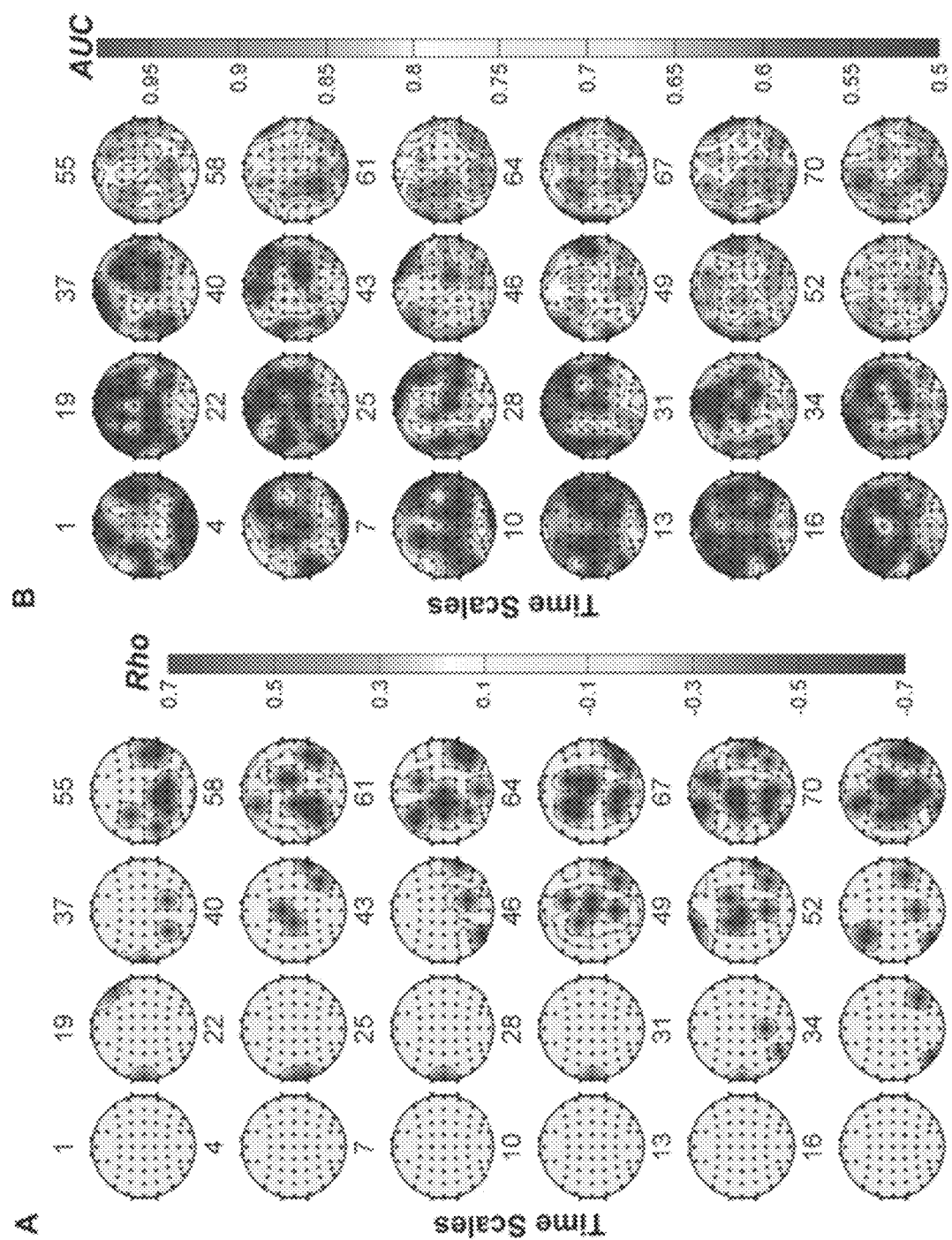
FIG. 12 (also referred to as FIG. S6) shows The Association between Change in Complexity and Autobiographical Memory.

FIG. 12 (also referred to as FIG. S6) shows The Association between Change in Complexity and Autobiographical Memory. A. Topographies illustrate all the significant (original p<0.05) spearman correlation coefficients (rho) between percent change in autobiographical memory interview (AMI) and multiscale entropy (MSE) across all time-scales for each electrode. Cluster-based permutation test correction for multiple comparison revealed a significant negative cluster in time-scales higher than 40 across brain regions including the fronto-parietal regions. B. Topographies depict area under the curve (AUC) of the receiver operating characteristic (ROC) curve of change in MSE in predicting change in AMI in response to seizure therapy at every electrode and time-scale. The hot colors illustrate higher AUC and better prediction. Change in complexity of coarse time-scales (e.g., >47) in fronto-parietal regions had excellent (AUC range: 0.9 to 1.00) prediction performance.

Figure 13:
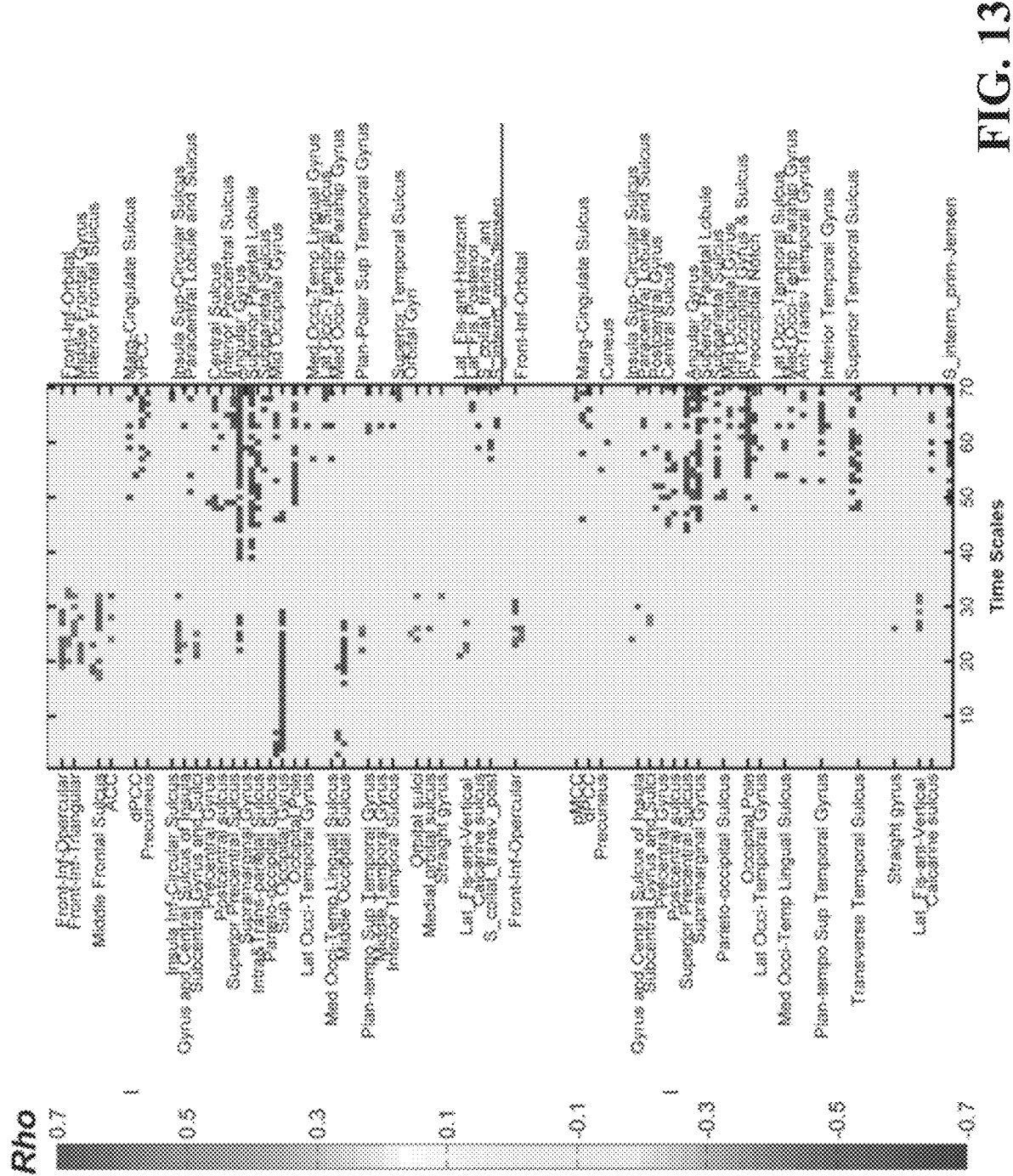
FIG. 13 (also referred to as FIG. S7) shows The Association between Change Complexity and Autobiographical Memory in Source Space.
Figure 13:
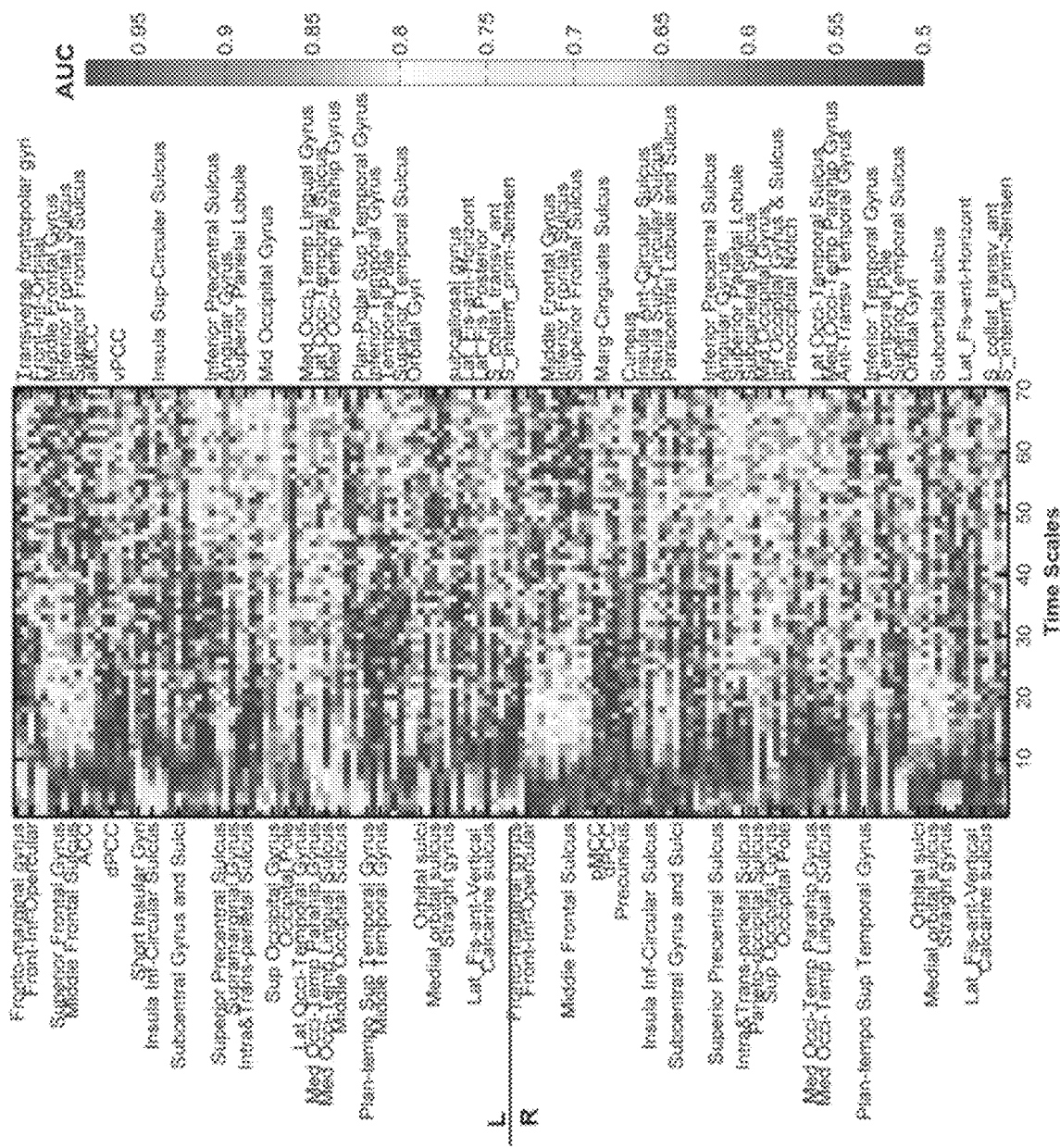

FIG. 13 (also referred to as FIG. S7) shows The Association between Change in Complexity and Autobiographical Memory in Source Space. A. Image illustrates the significant (p<0.05) spearman correlation coefficients (rho) between percent change in autobiographical memory interview (AMI) and multiscale entropy (MSE) at every Region of Interest (ROI) of the Destrieux Atlas (1 to 148) and each time-scale (1 to 70). All sources and scales that did not survive the correction for multiple comparisons were set to 0 (green colors). Only sources that are significant have been listed. B. Image depicts the area under the curve (AUC) of the receiver operating characteristic (ROC) curve of change in MSE in predicting change in AMI in response to seizure therapy at every ROI and each time-scale (1 to 70). Hot colors illustrate higher AUC and better prediction. Change in complexity of higher time-scales in several bilateral frontal and parietal regions provided excellent (AUC range: 0.9 to 1.00) prediction performance for change in AMI.

FIG. 14 shows the Effect of Escitalopram on Complexity of Temporal Dynamics. Top: Images show the original post-hoc test statistics comparing MSE pre (baseline) to post treatment (week 8) across all electrodes (1 to 58) and all time-scales (1 to 70) (blue: increases; red: decreases following treatment) for responders (left) and non-responders to escitalopram (right). Bottom. Each topography reflects the significant t-maps following correction for multiple comparison, using cluster-based non-parametric permutation test for p=0.05, depicting only the clusters p<0.09 and setting to 0 other pixels. Topographies highlight the spatial characteristics of the reduction of MSE in fine time-scales in responders to escitalopram in fronto-parietal brain regions (cluster p=0.09). No significant changes were observed in non-responders.

FIG. 15 shows the Association between Modulation of Temporal Complexity and Mood. Top. Image illustrate all the significant (original p<0.05) spearman correlation coefficients (rho) between percent change in MADRS and change in MSE (pre-post) in 95 patients receiving escitalopram therapy. Cluster-based correction for multiple comparison resulted in significant clusters (p<0.05) in parieto-occipital and fronto-central regions in time-scale less than 10 factors. Bottom. Topographies illustrate spatial distribution of this association.

FIG. 16 shows the Escitalopram Induced Modulation of Complexity and Its Association with Mood in Source Space. In the left image, the x-axis represents the time scales (1 to 70) and y-axis represents Regions of Interest (ROIs) of the Destrieux Atlas (1 to 148). Images show the post-hoc test statistics following cluster-based permutation test correction for multiple comparison, depicting only the significant clusters p<0.05, labeling only the significant corresponding ROIs and setting to 0 non-significant pixels. Scatter plots show that only region-specific reduction in MSE in fine time-scales (less than 20 time scales) was significantly associated with enhancement of MADRS.

FIG. 17 show Differential Early Changes in Complexity of Temporal Dynamics during Escitalopram Treatment in Responders and Non-Responders. Top. Images show the original post-hoc test statistics comparing MSE at week 2 relative to pre treatment (baseline) across all electrodes (1 to 58) and all time-scales (1 to 70) (blue: decreases; red: increases following treatment) for responders (Left column) and non-responders (Right column) from baseline to week 2. Bottom. Each topography reflects the significant t-maps following correction for multiple comparison, using cluster-based non-parametric permutation test, depicting only the significant clusters p<0.05 and setting to 0 non-significant pixels. Topographies highlight the spatial characteristics of the reduction of MSE in coarse time-scales in non-responders. The reduction of MSE in coarse time-scales (e.g., scale factor>18) was localized to lateral frontal, fronto-temporal, and parieto-occipital brain regions. No significant changes were observed in non-responders.

FIG. 18 shows Source Localization of Early Changes in Temporal Complexity in Non-Responders to Escitalopram. X-axis represents the time scales (1 to 70) and y-axis represents Regions of Interest (ROIs) of the Destrieux Atlas (1 to 148). Images show the post-hoc test statistics following cluster-based permutation test correction for multiple comparison, depicting only the significant clusters p<0.05, labeling only the significant corresponding ROIs and setting to 0 non-significant pixels.

FIG. 19 show the Link Between Baseline Complexity and Change in Mood by Escitalopram. Top. Image illustrate all the significant (p<0.05) spearman correlation coefficients (rho) between percent change in MADRS (week 8 to baseline) and baseline MSE (pre-post) in 95 patients receiving escitalopram therapy. Cluster-based correction for multiple comparison resulted in significant clusters (p<0.05) across multiple brain regions (global') such as in parieto-occipital and fronto-central regions in time-scale higher than 37. Bottom. Topographies illustrate spatial distribution of this association.

FIG. 20 shows the Link between Baseline Complexity and Change in Mood by Escitalopram in Source Space. Source analysis of data from prior figure reflects all brain region whose baseline complexity is associated with change in depressive symptoms following Escitalopram therapy.

FIG. 21 shows the Link between Week 2 Complexity and Change in Mood by Escitalopram. Image illustrate all the significant (p<0.05) spearman correlation coefficients (rho) between percent change in MADRS (week 8 to baseline) and week 2 MSE in 95 patients receiving escitalopram therapy. Cluster-based correction for multiple comparison resulted in significant clusters (p<0.05) across multiple brain regions. Bottom. Topographies illustrate spatial distribution of this association.

FIG. 22 shows the Link between Week 2 Complexity and Change in Mood by Escitalopram in Source Space. Source analysis of data from prior figure reflects all brain region whose complexity at week 2 of treatment is associated with change in depressive symptoms following Escitalopram 8 weeks of therapy.

What is claimed is:

1. A method of assessing the efficacy of an anti-depression treatment in a subject having depression, said method comprising:
    obtaining a baseline measurement of the subject by assessing first neuroimaging data sensed from a brain of the subject to determine at least one measure of baseline complexity of temporal dynamics in the brain of the subject;
    treating the subject with the anti-depression treatment, where the anti-depression treatment comprises at least one of: treatment using electrical stimulation, treatment using transcranial magnetic stimulation, and pharmacological treatment;
    obtaining a post-treatment measurement of the subject by assessing second neuroimaging data sensed from the brain of the subject to determine at least one measure of post-treatment complexity of temporal dynamics in the brain of the subject; and
    evaluating a change in complexity of temporal dynamics in the brain of the subject following the anti-depression treatment by comparing the at least one measure of post-treatment complexity to the at least one measure of baseline complexity to identify whether complexity of fine time scale temporal dynamics in one or both of a fronto-central region and a parieto-occipital region of the brain of the subject is reduced following the anti-depression treatment;
    detecting reduced complexity of fine time scale temporal dynamics in one or both of the fronto-central region and the parieto-occipital region of the brain of the subject following the anti-depression treatment;
    classifying the subject as a responder to the anti-depression treatment and identifying the anti-depression treatment as efficacious;
    wherein the step of evaluating further comprises identifying a change in complexity of coarse scale temporal dynamics in a parieto-central region of the brain of the subject following the anti-depression treatment, and wherein reduced or maintained complexity of coarse scale temporal dynamics is detected in the parieto-central region of the brain of the subject following the anti-depression treatment identifies that deleterious cognitive side-effects of the anti-depression treatment in the subject are limited; and
    generating a further treatment plan for the subject, wherein the further treatment plan comprises providing additional unmodified treatment to the subject.

2. The method of claim 1, wherein the complexity of the fine time scale temporal dynamics and the complexity of the coarse scale temporal dynamics in the brain of the subject is evaluated using electroencephalography (EEG).

3. The method of claim 1, wherein the fine time scale temporal dynamics comprises less than 30 factors in the parieto-occipital region of the brain of the subject.

4. The method of claim 1, wherein the parieto-occipital region of the brain of the subject comprises at least a right occipital pole of the brain of the subject.

5. The method of claim 1, wherein the coarse scale temporal dynamics comprise greater than 50 factors, and less than 70 factors, in the parieto-central region of the brain.

* * * * *